(12) United States Patent
Cornea et al.

(10) Patent No.: US 10,281,476 B2
(45) Date of Patent: May 7, 2019

(54) METHODS TO IDENTIFY MODULATORS OF RYR CALCIUM CHANNELS

(71) Applicants: REGENTS OF THE UNIVERSITY OF MINNESOTA, Minneapolis, MN (US); THE REGENTS OF THE UNIVERSITY OF CALIFORNIA, Oakland, CA (US)

(72) Inventors: Razvan L. Cornea, Minneapolis, MN (US); Donald M. Bers, Davis, CA (US); David D. Thomas, Minneapolis, MN (US); Gregory D. Gillispie, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 797 days.

(21) Appl. No.: 14/565,811

(22) Filed: Dec. 10, 2014

(65) Prior Publication Data

US 2015/0160216 A1 Jun. 11, 2015

Related U.S. Application Data

(60) Provisional application No. 61/914,048, filed on Dec. 10, 2013.

(51) Int. Cl.
*G01N 31/00* (2006.01)
*G01N 33/53* (2006.01)
*G01N 33/68* (2006.01)

(52) U.S. Cl.
CPC ... *G01N 33/6893* (2013.01); *G01N 2800/326* (2013.01)

(58) Field of Classification Search
CPC .......... A61B 5/14556; C07K 14/43595; G01N 33/542; G01N 33/56966; G01N 33/582; G01N 33/84; A61K 31/554
See application file for complete search history.

(56) References Cited

U.S. PATENT DOCUMENTS

| | | | |
|---|---|---|---|
| 6,816,102 | B2 | 11/2004 | Pavicic |
| 7,413,862 | B2 | 8/2008 | Van Dongen et al. |
| 2006/0134644 | A1 | 6/2006 | Hartel et al. |
| 2012/0021926 | A1 | 1/2012 | Thomas et al. |
| 2013/0231262 | A1 | 9/2013 | Robia |
| 2015/0204847 | A1 | 7/2015 | Thomas et al. |

FOREIGN PATENT DOCUMENTS

WO  WO 2010/085514 A1  7/2010

OTHER PUBLICATIONS

Lanner et al. (Cold Spring Harb Perspectives in Biology, 2010, vol. 2 pp. 1-21).*
Petegem (The Journal of Biological Chemistry, vol. 287, No. 38, pp. 31624-3'632, Sep. 14, 2012).*
Petegem (The Journal of Bioogical Chemistry, vol. 287, No. 38, pp. 31624-31632, Sep. 14, 2012).*
George et al. (Molecular Biology of the Cell, vol. 15, 2627-2638, Jun. 2004, pp. 2627-2638).*
Lanner et al. (Cold Spring harb Perspectives in Biology, 2010, pp. 1-21).*
Petegem (The Journal of Biological Chemistry, vol. 287, No. 38, pp. 31624-31632, Sep. 14, 2012).*
George et al (Molecular Biology of the Cell, vol. 15, pp. 2627-2638, Jun. 2004).*
Cornea et al. (PNAS, vol. 106, No. 15, Apr. 14, 2009, pp. 6128-6133).*
Acker et al., "Considerations for the design and reporting of enzyme assays in high-throughput screening applications," *Perspect Sci*, May 2014;1(1-6):56-73.
Ai et al., "Ca2+/calmodulin-dependent protein kinase modulates cardiac ryanodine receptor phosphorylation and sarcoplasmic reticulum Ca2+ leak in heart failure," *CircRes*, 2005;97:1314-1322.
Andersson et al., Leaky ryanodine receptors in beta-sarcoglycan deficient mice: A potential common defect in muscular dystrophy, *Skelet Muscle*, 2012;2:9.
Aracena et al., "Effects of S-Glutathionylation and S-Nitrosylation on Calmodulin Binding to Triads and FKBP12 Binding to Type 1 Calcium Release Channels," *Antioxid Redox Signal*, 2005;7:870-881.
Arbabian et al., "Endoplasmic reticulum calcium pumps and cancer," *Biofactors*, 2011;37:139-149.
Ariazi et al., "Estrogen-related receptors as emerging targets in cancer and metabolic disorders" *Curr Top Med Chem*, 2006;6:203-215.
Arnou et al., "The Plasmodium falciparum Ca(2+)-ATPase PfATP6: insensitive to artemisinin, but a potential drug target," *Biochem Soc Trans*, 2011;39:823-831.
Ausubel, R.M., *Current Protocols in Molecular Biology*, 1994.
Bagshaw et al., "ATP analogues at a glance," *J Cell Science*, Feb. 1, 2001;114(3):459-460.
Balog et al., *AmJPhysiolHeartCircPhysiol.*, 2006;290:H794-H799.
Balshaw et al., "Modulation of intracellular calcium-release channels by calmodulin," *J Membr Biol.*, 2002;185:1-8.
Balshaw et al., "Calmodulin Binding and Inhibition of Cardiac Muscle Calcium Release Channel (Ryanodine Receptor)," *JBiolChem*, 2001;276;20144-20153.

(Continued)

*Primary Examiner* — Lisa V Cook
(74) *Attorney, Agent, or Firm* — Mueting, Raasch & Gebhardt, PA

(57) ABSTRACT

Provided herein are methods for identifying a compound that modulates a Ryanodine receptor (Ryr). Fluorescence resonance energy transfer between an FKBP bound to an RyR and fluorescent derivatives of RyR binding partners (e.g., calmodulin) or domain-peptide biosensors is used to provide a readout dependent on the RyR functional state. The methods permit measurement of RyR present in a permeabilized cell or in a purified membrane.

15 Claims, 30 Drawing Sheets

Specification includes a Sequence Listing.

(56) References Cited

OTHER PUBLICATIONS

Banerjee et al., "Proteoliposome as the model for the study of membrane-bound enzymes and transport proteins," *Molecular and Cellular Biochemistry*, 1983;50:3-15.
Beechem et al., *Numer Comput Methods*, 1992;210;37.
Bers DM, "Cardiac excitation-contraction coupling," *Nature*, 2002;415:198-205.
Bers, "Macromolecular complexes regulating cardiac ryanodine receptor function," *JMolCellCardiol*, 2004;37:417-429.
Bers, "Ryanodine receptor S2808 phosphorylation in heart failure: smoking gun or red herring," *CircRes*, 2012;110:796-799.
Bers DM, "Cardiac Sarcoplasmic Reticulum Calcium Leak: Basis and Roles in Cardiac Dysfunction," *AnnuRevPhysiol*, Feb. 2014;76:107-127.
Bers et al., "Ratio of ryanodine to dihydropyridine receptors in cardiac and skeletal muscle implications for E-C coupling," *Am J Physiol*, 1993;264:C1587-C1593.
Boraso et al., *AmJPhysiol.*, 1994;267:H1010-1016.
Bossuyt et al., "Spatiotemporally Distinct Protein Kinase D Activation in Adult Cardiomyocytes in Response to Phenylephrine and Endothelin," *J Biol Chem*, Sep. 23, 2011;286(38):33390-33400.
Comley, "Fluorescence Lifetime-finally picking up momentum!" Drug Discovery World Summer 2010; pp. 71-82.
Cornea et al., "High-throughput FRET assay yields allosteric SERCA activators," *J Biomol Screen*, Jan. 2013;18(1):97-107.
Cornea et al., "Mapping the ryanodine receptor FK506-binding protein subunit using fluorescence resonance energy transfer," *J BiolChem*, 2010;285:19219-19226.
Cornea et al., "FRET-based mapping of calmodulin bound to the RyR1 Ca2+ release channel," *PNAS USA*, 2009;106:6128-6133.
Degorce et al., "HTRF: A Technology Tailored for Drug Discovery—A Review of Theoretical Aspects and Recent Applications," *Curr Chem Genomics*, Mar. 2009;3 :22-32.
Diaz-Sylvester et al., "Halothane modulation of skeletal muscle ryanodine receptors: dependence on $Ca^{2+}$, $Mg^{2+}$, and ATP," *AmJPhysiolCellPhysiol.*, Apr. 1, 2008;294(4):C1103-C1112.
Dong et al., "Time-resolved FRET reveals the structural mechanism of SERCA—PLB regulation," *Biochem Biophys Res Commun*, Jun. 27, 2014;449(2):196-201.
Donoso et al., "Stimulation of NOX2 in isolated hearts reversibly sensitizes RyR2 channels to activation by cytoplasmic calcium,"*JMolCellCardiol*, Mar. 2014;68:38-46.
Erickson et al., "A Dynamic Pathway for Calcium-Independent Activation of CaMKII by Methionine Oxidation,"*Cell*, May 2, 2008;133:462-474.
Erickson et al., "Diabetic hyperglycaemia activates CaMKII and arrhythmias by O-linked glycosylation," *Nature*, Oct. 17, 2013; 502:372-376.
Feher et al., "Determinants of calcium loading at steady state in sarcoplasmic reticulum," *Biochem Biophys Acta*, 1983;727:389-402.
Fruen et al., "Differential $Ca^{2+}$ sensitivity of skeletal and cardiac muscle ryanodine receptors in the presence of calmodulin," *Am J Physiol-Cell Phys*, Sep. 1, 2000;279:C724-C733.
Fu et al., "Aberrant lipid metabolism disrupts calcium homeostasis causing liver endoplasmic reticulum stress in obesity," *Nature*, 2011;473:528-531.
Fukuda et al., "Enhanced binding of calmodulin to RyR2 corrects arrhythmogenic channel disorder in CPVT-associated myocytes," *BiochemBiophysResComm*, 2014;448:1-7.
Gakamsky et al., "Use of fluorescence lifetime technology to provide efficient protection from false hits in screening applications," *Anal. Biochem*, Feb. 1, 2011;409(1):89-97.
Gehrig et al., "Hsp72 preserves muscle function and slows progression of sever muscular dystrophy," *Nature*, 2012;484:394-398.
Goonasekera et al., "Mitigation of muscular dystrophy in mice by SERCA overexpression in skeletal muscle," *J Clin Invest*, 2011;121:1044-1052.
Grashoff et al., *Nature*(London), 2010;466:263.
Greensmith et al., "The effects of hydrogen peroxide on intracellular calcium handling and contractility in the rat ventricular myocyte," *CellCalcium*, 2010;48:341-351.
Gribbon et al., "Fluorescence readouts in HTS: no gain without pain?" *Drug Discov Today*, Nov. 15, 2003;8(22):1035-1043.
Gruber et al., "Phospholamban mutants compete with wild tye for SERCA binding in living cells," *Biochem Biophys Res Commun*, 2012;420:236-240.
Gruber et al., "Discovery of Enzyme Modulators via High-Throughput Time-Resolved FRET in Living Cells," *J Biomolecular Screening*, 2014;19(2):215-222.
Gruber-Presentation—"In-cell FRET as a Tool to Develop SERCA Activators for Drug or Gene Therapy," Poster presented at $57^{th}$ Biophysical Society Annual Meeting, Feb. 2-6, 2013; Philadelphia, PA.
Guo et al., "FRET detection of calmodulin binding to the RyR2 calcium release channel," *BiophysJ*, 2011;101:2170-2177.
Guo et al., "Ca2+/Calmodulin-dependent protein kinase II phosphorylation of ryanodine receptor does affect calcium sparks in mouse ventricular myocytes," *CircRes*, Aug. 18, 2006;99(4):398-406.
Guo et al., "Kinetics of FKBP12.6 binding to ryanodine receptors in permeabilized cardiac myocytes and effects on Ca sparks," *CircRes*, Jun. 11, 2010;106(11):1743-1752.
Hamilton, SL., "Ryanodine receptor structure: Progress and challenges," *J Biol Chem*, Feb. 13, 2009; 284(7):4047-4051.
Hartigan et al., "Tracking HTS Assay Development Time: opportunity for improving drug discovery," Drug Discovery World Summer 2010; pp. 51-58.
Hermanson et al., "Dual mechanisms of sHA 14-1 in inducing cell death through endoplasmic reticulum and mitochondria," *Mol Pharmacol*, 200+9;76:667-678.
Ho et al., *JPhysiol.*, 2011;19:4697-4708.
Hou et al., "2-Color calcium pump reveals closure of the cytoplasmic headpiece with calcium binding," *PLoSONE*, Jul. 11, 2012;7(7):e40369: 10 pgs.
Houser et al., "Protein Kinase A—Mediated Hyperphosphorylation of the Ryanodine Receptor at Serine 2808 Does Not Alter Cardiac Contractility or Cause Heart Failure and Arrhythmias," *CircRes*, Apr. 11, 2014;114(8):1320-1327.
Huang et al., "Two potential calmodulin-binding sequences in the ryanodine receptor contribute to a mobile, intra-subunit calmodulin-binding domain," *J Cell Sci*, Oct. 1, 2013;126(19):4527-4535.
Hwang et al., "Divergent Regulation of Ryanodine Receptor 2 Calcium Release Channels by Arrhythmogenic Human Calmodulin Missense Mutants," *CircRes*, Mar. 28, 2014;114(7):1114-1124.
Ikemoto, "Regulation of calcium release by interdomain interaction within ryanodine receptors," *FrontBiosci*, 2002;7:d671-d683.
Ikemoto, "Ryanodine Receptors: Structure, Function and Dysfunction in Clinical Diseases," New York, NY; Springer, 2004;53-65.
Inesi et al., "The Ca2+ ATPase of ccardiac sarcoplasmic reticulum: Physiological role and relevance to diseases," *Biochem Biophys Res Commun*, 2008;369:182-187.
Inesi et al., "Concerted conformational effects of Ca2+ and ATP are required for activation of sequential reactions in the Ca2+ ATPase (SERCA) catalytic cycle," *Biochemistry*, 2006;45:13769-13778.
Inglese et al., *Nat Chem Biol*, 2007;3:466.
Isenberg et al., *Biophys J*, 1969;9:1337.
Jameson et al., "Investigations of protein—protein interactions using time-resolved fluorescence and phasors," *Methods*, Mar. 1, 2013;59(3):278-286.
Jessup et al., "Calcium Upregulation by percutaneous Administration of Gene Therapy in Cardiac Disease (CUPID): a phase 2 trial of intracoronary gene therapy of sarcoplasmic reticulum Ca2+-ATPase in patients with advanced heart failure," *Circulation*, 2011;124:304-313.
Johnson et al., "Cardiac sarcoplasimic reticulum function and regulation of contractility-Introduction,"*Ann NY Acad Sci*, 1998;853:xi-xvi.
Johnson et al., "Pharmacology of the cardiac sarcoplasmic reticulum calcium ATPase phospholamban interaction," *Ann NY Acad Sci*, 1998;853:380-392.
Jung et al., *EMBOMolMed*, 2012;4:180-191.

(56) References Cited

OTHER PUBLICATIONS

Kast et al., *Proc Natl Acad Sci USA*, 2010;107:8207.
Kleinfelder, *Proc SPIE*, 2003;4858:316.
Kimura et al., "Alternative splicing of ryr1 alters the efficacy of skeletal ec coupling," *CellCalcium*, 2009;45:264-274.
Knutson et al., *Chem Phys Lett*, 1983;102:501.
Kobayashi et al., "Dantrolene Stabilzes Domain Interactions within the Ryanodine Receptor," *JBiolChem*, Feb. 25, 2005; 280(8):6580-6587.
Kobayashi et al., "Dantrolene, a therapeutic agent for malignant hyperthermia, markedly improves the function of failing cardiomyocytes by stabilizing interdomain interactions within the ryanodine receptor," *JAmCollCardiol*, 2009;53:1993-2005.
Kobayashi et al., *CircJ.*, 2010;74:2579-2584.
Krause et al., *Anaesthesia*, 2004;59:364-373.
Lagalwar and Orr, *Methods Mol Biol*, 2013;1010:201-209.
Lakowicz et al. *Principles of Fluorescence Spectroscopy*, 3$^{rd}$ ed. Springer, New York, 2006; Table of Contents and Index.
Lebakken et al., "A Fluorescence Lifetime—Based Binding Assay to Characterize Kinase Inhibitors," *J Biomol Screening*, 2007;12:828.
Li et al., *Electrophoresis*, 2014;35(12-13):1846.
Li et al., "A phosphorylation of the ryanodine does not affect calcium sparks in mouse ventricular myocytes," *CircRes*, 2002;90:309-316.
Liu et al., "Dynamic, inter-subunit interactions between the N-terminal and central mutation regions of cardiac ryanodine receptors," *J Cell Sci*, 2010;123:1775-1784.
MacLennan et al., "Phospholamban: a crucial regulator of cardiac contractility," *Nature Reviews*, 2003;4:666-678.
Maltman et al., *Chem Commun*, 2010;46:6929.
Marks, "Calcium cycling proteins and heart failure: Mechanisms and therapeutics," *J Clin Invest*, 2013;123:46-52.
Marquez et al., *Curr Drug Targets*, 2011;12:600-620.
Maruyama et al., "Mutation of aspartic acid-351, lysine-352, and lysine-515 alters the Ca2+ transport activity of the Ca2+-ATPase expressed in COS-1 cells," *PNAS USA*, 1988;85:3314-3318.
Marx et al., *CircRes*, 2001;88:1151-1158.
Maxwell et al., *AmJPhysiolHeartCircPhysiol.*, 2012;302:H953-63.
McMurray et al., *EurHeartJ*, 1993;14:1493-1498.
Meng et al., "Orientation-based FRET sensor for real-time imaging of cellular forces," *J Cell Sci*, 2012;125:743.
Michelangeli et al., "A diversity of SERCA Ca2+ pump inhibitors," *Biochem Soc Trans*, 2011;39:789-797.
Moger et al., *Screening*, 2006;11:765.
Morine et al., "Overexpression of SERCA1a in the mdx diaphragm reduces susceptibility to contraction-induced damage," *Hum Gene Ther*, 2010; 21:1735-1739.
Mueller et al., "SERCA structural dynamics induced by ATP and calcium," *Biochemistry*, 2004;43:12846-12854.
Mueller et al., "Direct detection of phospholamban and sarcoplasmic reticulum Ca-ATPase interaction in membranes using fluorescence resonance energy transfer," *Biochemistry*, 2004;43:8754-8765.
Muretta et al., High-performance time-resolved fluorescence by direct waveform recording, *Rev Sci Instrum*, 2010;81:103101.
Muretta et al., *Proc Acad Natl Sci USA*, 2013;110:7211-7216.
Nesmelov et al., *Proc Acad Natl Sci USA*, 2011;108(5):1891.
Oda et al., "Defective Regulation of interdomain interactions within ryanodine receptor plays a key role in the pathogenesis of heart failure," *Circulation*, 2005;111:3400-3410.
Oda et al., "In Cardiomyocytes, Binding of Unzipping Peptide Activates Ryanodine Receptor 2 and Reciprocally Inhibits Calmodulin binding," *Circulation*, 2013;112:487-497.
Ono et al., *CardiovasRes*, 2010;87:609-617.
Park et al., "Sarco(endo)plasmic reticulum Ca2+-ATPase 2b is a major regulator of endoplasmic reticulum stress and glucose homeostasis in obesity," *Proc Natl Acad Sci USA*, 2010;107:19320-19325.
Paterson et al., "A fluorescence lifetime-based assay for serine and threonine kinases that is suitable for high-throughput screening," *Anal Biochem*, 2010;402:54.
Paul-Pletzer et al., *Biochem J*, 2005;387:905-909.
Peterson et al., "Fluorescence lifetime plate reader: Resolution and precision meet high-throughput," *Review of Scientific Instruments*, 2014;85:113101.
Picht et al., "Sparkmaster: Automated calcium Spark Analysis with ImageJ," *Am J Physiol Cell; Physiol*, :2007;293:C1073-C1081.
Prestle et al., "Overexpression of FK506-binding protein FKBP12.6 in cardiomyocytes reduces ryanodine receptor-mediated Ca(2+) leak from the sarcoplasmic reticulum and increases contractility," *CircRes*, 2001;88:188-194.
Priori et al., "Inherited dysfunction of sarcoplasmic reticulum Ca2+ handling and arrhythmogenesis," *CircRes*, 2011;108:871-883.
Pritz et al., "A Fluorescence Lifetime-Based Assay for Abelson Kinase," *J Biomol Screening*, 2011;16(1): 65-72.
Pritz et al., *Expert Opin Drug Discovery*, 2011;6:663.
Qin et al., *JAmHeartAssoc*, 2013;2:e000184.
Raina et al., *PLoSOne*, 2012;7:e38594.
Rolland et al., "Sarcopenia: Its assessment, etiology, pathogenesis, consequences and future perspectives," *J Nutr Health Aging*, 2008;12:433-450.
Sambrook et al., *Molecular Cloning: A Laboratory Manual*, Cold Spring Harbor Laboratory Press, 1989.
Samsó et al., "Apocalmodulin and Ca2+-calmodulin bind to neighboring locations on the ryanodine receptor," *JBiolChem*, Jan. 11, 2002;277(2):1349-1353.
Samsó et al., "Structural Characterization of the RyR1-FKBP12 interaction," *J Mol Biol*, 2006;356:917-927.
Shan et al., *JClinInvest*, 2010;120:4375-4387.
Simeonov et al., *J Med Chem*, 2008;51:2363.
Song et al., *J Biol Chem*, 2011;286:9120-9126.
Song et al., "Differential integration of Ca2+-calmodulin signal in intact ventricular myocytes at low and high affinity Ca2+-calmodulin targets," *JBiolChem*, 2008;283 :31531-31540.
Stange et al., *JBiolChem.*, 2003;278:51693-51702.
Stergiopoulous et al., *BMC Health Serv Res*, 2012;12:345.
Szollosi et al., *CommunicationsinClinicalCytometry*, 1998;34:159-179.
Tateishi et al., "Defective domain-domain interactions within the ryanodine receptor as a critical cause of diastolic Ca$^{2+}$ leak in failing hearts," *CardiovascRes*, 2009;81:536-545.
Tazzeo et al. "the NADPH oxidase inhibitor diphenyleneiodonium is also a potent inhibitor of cholinesterases and the internal Ca(2+) pump," *Br J Pharmacol*, 2009;158:790-796.
Terentyev et al., *CircRes*, 2008;103:1466-1472.
Thomas et al., *PNAS USA*, 1978;75:5746-5750.
Thorne et al., "Apparent activity in high-throughput screening: origins of compound-dependent assay interference," *Curr Opin Chem Biol*, 2010;14:315.
Tung et al., "The amino-terminal disease hotspot of ryanodine receptors forms a cytoplasmic vestibule," *Nature*, 2010;468:585-588.
Uchinoumi et al., "Catecholaminergic polymorphic ventricular tachycardia is caused by mutation-linked defective conformational regulation of the ryanodine receptor," *CircRes*, 2010;106:1413-1424.
Valley et al., "Tumor Necrosis Factor-related Apoptosis-inducing Ligand (TRAIL) Induces Death Receptor 5 Networks That Are Highly Organized," *J Biol Chem*, 2012;287:21265-21278.
Wagner et al., *CircRes*, 2011;108:555-565.
Wang et al., "Localization of an NH(2)-terminal disease-causing mutation hot spot to the "clamp" region in the three-dimensional structure of the cardiac ryanodine receptor," *JBiolChem*, 2007;282:17785-17793.
Wang et al., *J BiolChem*, 2011;286:12202-12212.
Wehrens et al., "FKBP12.6 deficiency and defective calcium release channel (ryanodine receptor) function linked to exercise-induced sudden cardiac death," *Cell*, 2003;113:829-840.
Wehrens et al., "Ryanodine receptor/calcium release channel PKA phosphorylation: A critical mediator of heart failure progression," *PNAS USA*, 2006;103:511-518.
Xiao et al., "Removal of FKBP12.6 does not alter the conductance and activation of the cardiac ryanodine receptor or the susceptibility to stress-induced ventricular arrhythmias," *J Biol Chem*, 2007;282:34828-34838.

(56) References Cited

OTHER PUBLICATIONS

Xu et al., "Defective calmodulin binding to the cardiac ryanodine plays a role in CPVT-associated channel dysfunction," *BiochemBiophysResComm*, 2010;394:660-666.

Yamaguchi et al., "Molecular basis of calmodulin binding to cardiac muscle Ca(2+) release channel (ryanodine receptor)," *J Biol Chem*, 2003;278:23480-23486.

Yamaguchi et al., *JClinInvest*, 2007;117:1344-1353.

Yamamoto et al., "Peptide Probe study of the critical regulatory domain of the cardiac ryanodine receptor," *BiochemBiophysResCommun*, 2002;291:1102-1108.

Yamamoto et al., "Spectroscopic Monitoring of Local Conformational Changes during the Intramolecular Domain-Domain Interaction of the Ryanodine Receptor," *Biochem*, 2002;41(5):1492-1501.

Yamamoto et al., "Postulated role of interdomain interaction within the ryanodine receptor Ca(2+) channel regulation," *JBiolChem*, 2000;275:11618-11625.

Yan et al., "Bidirectional regulation of Ca21 sparks by mitochondria-derived reactive oxygen species in cardiac myocytes," *CardiovasRes*, 2008;77:432-441.

Yang et al., "In situ measurement of RyR2-calmodulin binding in permeablized cardiomyocytes," *Biophys J*, 2011;100:413a-414a.

Yang et al., *CircRes*, 2014;114:295-306.

Yano et al., "Altered stoichiometry of FKBP12.6 versus ryanodine receptor as a cause of abnormal Ca(2+) leak through ryanodine receptor in heart failure," *Circulation*, 2000;2131-2136.

Yano et al., *Circulation*, 2005;112:3633-3643.

Yuan et al., "Genetic mapping of targets mediating differential chemical phenotypes in Plasmodium falciparum," *Nat Chem Biol*, 2009;5:765-771.

Zhang et al., "A simple statistical parameter for use in evaluation and validation of high throughput screening assays," *JBiolScreen*, 1999;4:67-73.

Zima et al., *J Physiol.*, 2010;588:4743-4757.

Fluorescence Innovations, "NovaFluor PR Fluorescence Lifetime Plate Reader" Poster, Mar. 2011.

\* cited by examiner

SEQUENCE LISTING

```
<160> NUMBER OF SEQ ID NOS: 1

<210> SEQ ID NO 1
<211> LENGTH: 36
<212> TYPE: PRT
<213> ORGANISM: artificial
<220> FEATURE:
<223> OTHER INFORMATION: DPc10 sequence

<400> SEQUENCE: 1

Gly Phe Cys Pro Asp His Lys Ala Ala Met Val Leu Phe Leu Asp Arg
1               5                   10                  15

Val Tyr Gly Ile Glu Val Gln Asp Phe Leu Leu His Leu Leu Glu Val
            20                  25                  30
```

Gly Phe Leu Pro
    35

METHODS TO IDENTIFY MODULATORS OF RYR CALCIUM CHANNELS

CROSS-REFERENCE TO RELATED APPLICATIONS

This application claims the benefit of U.S. Provisional Application Ser. No. 61/914,048, filed Dec. 10, 2013, which is incorporated by reference herein.

GOVERNMENT FUNDING

This invention was made with government support under R01-HL092097, R01HL076433, P01-HL080101, and R01GM27906 awarded by the National Institutes of Health. The government has certain rights in the invention.

SEQUENCE LISTING

This application contains a Sequence Listing electronically submitted via EFS-Web to the United States Patent and Trademark Office as an ASCII text file entitled "11004350101_SequenceListing_ST25.txt" having a size of 1 kilobyte and created on Aug. 28, 2017. The information contained in the Sequence Listing is incorporated by reference herein.

BACKGROUND

The cardiac ryanodine receptor (ryanodine receptor 2, RyR2) $Ca^{2+}$ release channel in the sarcoplasmic reticulum (SR) membrane plays a central role in cardiac excitation—contraction coupling (Bers, *J Mol Cell Cardiol*, 2004; 37:417-429). During the past 10 years, diastolic $Ca^{2+}$ leak through dysfunctional RyR2 has been recognized as an important factor contributing to altered $Ca^{2+}$ homeostasis and arrhythmias in heart failure (HF). Evidence from several reports shows that RyR2 abnormality in HF causes increased diastolic $Ca^{2+}$ leak, leading to contractile and relaxation dysfunction (Yano et al., *Circulation*, 2000; 102:2131-2136; Ai et al., *Circ Res*, 2005; 97:1314-1322; Wehrens et al., *PNAS USA*, 2006; 103:511-518). Furthermore, the abnormal $Ca^{2+}$ leak through RyR2 provides a substrate for delayed after depolarization that leads to lethal arrhythmias (Wehrens et al., *Cell*, 2003; 113:829-840). The connection between cardiac dysfunction and RyR2 leak is extensively discussed in Bers D M (Annu Rev Physiol, 2014; 76:107-127)

One leading hypothesis explains the RyR2 dysfunction in HF and lethal arrhythmias, such as catecholaminergic polymorphic ventricular tachycardia (CPVT), by structural RyR2 changes that result in defective interaction (or zipping) between the N-terminal (N: 0-600) and the central (C: 2000-2500) domains (Yamamoto et al., *Biochem Biophys Res Commun*, 2002; 291:1102-1108). According to this concept, in the resting state, the N-terminal and central RyR2 domains interact with each other to act as a regulatory switch that influences RyR channel gating. This tight interdomain interaction, termed domain zipping, seems to stabilize the closed channel. Weakening of these interdomain interactions may be caused by mutations either in the N-terminal or central regions of RyR2 (Uchinoumi et al., *Circ Res*, 2010; 106:1413-1424) or via competition by peptides derived from these 2 domains (domain unzipping), (Ikemoto, *Front Biosci*, 2002; 7:d671-d683; Ikemoto in "Ryanodine Receptors: Structure, Function and Dysfunction in Clinical Disease," New York, N.Y.: Springer; 2004:53-65; Yamamoto et al., *J Biol Chem*, 2000; 275:11618-11625) resulting in an increased opening probability of the RyR2 and leakiness of $Ca^{2+}$. Domain peptide corresponding to RyR2 residues 2460-2495 (DPc10) is a synthetic peptide corresponding to a 36-residue stretch of the central domain ($Gly^{2460}$-$Pro^{2495}$) of RyR2 (Yamamoto et al., *Biochem Biophys Res Commun*, 2002; 291:1102-1108). It has been shown that DPc10 can specifically and directly associate with the N-terminal domain, (Oda et al., *Circulation*, 2005; 111:3400-3410; Tateishi et al., *Cardiovasc Res*, 2009; 81:536-545) and thus can compete with its zipping to the central domain, and that the N-domain/DPc10 association can destabilize RyR2 (via domain unzipping) to increase $Ca^{2+}$ leakiness (Oda et al., *Circulation*, 2005; 111:3400-3410). A single point mutation in DPc10 (R2474S) prevents all DPc10 effects, and a related human RyR2 mutation is associated with CPVT and RyR2 leakiness.

Tateishi et al. (Tateishi et al., *Cardiovasc Res*, 2009; 81:536-545) reported that a domain peptide (residues 163-195 of the N-terminal RyR2 domain, DP163-195) also induced $Ca^{2+}$ leak from SR, presumably because it binds to the central domain and competes with the N-terminal/central zipping.

The FK506-binding proteins FKBP12 and FKBP12.6 are expressed in cardiac myocytes and can form tight complexes with RyR at a stoichiometry of 4 FKBPs per tetrameric RyR channel (Bers, *J Mol Cell Cardiol*, 2004; 37:417-429). As such, these FKBP isoforms are considered important RyR2 subunits and have been reported to promote the closed channel state, but this role is controversial in myocytes from normal rat hearts (Bers, *Circ Res*, 2012; 110:796-799). FKBP12 does not significantly alter $Ca^{2+}$ sparks, whereas FKBP12.6 is slightly inhibitory, PKA-dependent RyR2 phosphorylation does not alter FKBP binding, and only a small fraction of RyR2 in native myocytes is FKBP12.6-bound (Guo et al., *Circ Res*. 2010; 106:1743-1752). Two previous studies in which RyR2 was treated with domain peptides to mimic pathological $Ca^{2+}$ leakage found no direct effect of DPc10 on FKBP12.6 coimmunoprecipitation with RyR2 (Oda et al., *Circulation*, 2005; 111:3400-3410; Tateishi et al., *Cardiovasc Res*, 2009; 81:536-545). It is unknown whether FKBP12.6 influences binding of DPc10 to RyR2 or the ensuing increased $Ca^{2+}$ leakage.

Calmodulin (CaM) is a ubiquitous $Ca^{2+}$-binding protein that binds to the RyR2 and modulates its channel function (Yamaguchi et al., *J Biol Chem*, 2003; 278:23480-23486). Binding of CaM within the cytosolic domain of RyR2 (at a site partly formed by residues 3583-3603) inhibits channel activity both at diastolic and at elevated $[Ca^{2+}]$ (Fruen et al., *Am J Physiol, Cell Physiol*, 2000; 279:C724-C733; Balshaw et al., *J Membr Biol*, 2002; 185:1-8). This indicates that CaM stabilizes the closed state of RyR2 in the resting state (Guo et al., *Circ Res*. 2006; 99:398-406). Interestingly, concurrent addition of a high concentration of CaM with DPc10 in wild-type cardiomyocytes reduced the $Ca^{2+}$ spark frequency (CaSpF) (calcium spark frequency) compared with addition of DPc10 alone. Furthermore, myocytes carrying a CPVT-linked RyR2 mutation (where β-adrenergic stimulation activates SR Ca leak) have defective interdomain interaction and reduced CaM binding to the RyR2 vs wild-type myocytes (Xu et al., *Biochem Biophys Res Commun*, 2010; 394:660-666). In addition, Ono et al. (Ono et al., *Cardiovasc Res*, 2010; 87:609-617) also reported that the CaM-binding affinity to RyR2 in HF is significantly reduced compared with that of normal RyR2. Treatment of wild-type myocytes with DPc10 also inhibited CaM binding at the Z-line in the CPVT mutants (Xu et al., *Biochem Biophys Res Commun*, 2010; 394:660-666).

SUMMARY OF THE APPLICATION

Described herein are methods based on fluorescence lifetime (FLT) detection of fluorescence resonance energy transfer (FRET), derivatives of the FK506 binding protein 12.6 (FKBP12.6) that may be covalently labeled with a fluorescent probe (termed F-FKBP) that bind specifically to the ryanodine receptor (RyR) calcium channels, and RyR constructs that contain one or two fluorescent fusion proteins. These methods permit high-throughput screening (HTS) of small-molecule libraries for compounds that modulate RyR function. FRET between RyR-bound FKBP or RyR/fluorescent fusion protein constructs and fluorescent derivatives of RyR binding partners (e.g., calmodulin) or domain-peptide biosensors is used to provide a readout dependent on the RyR functional state.

Changes in this readout are often too small to detect using conventional steady-state fluorescence detection, but the inventors have determined they can be reliably detected using direct wave recording measurements of FLT. These methods can be used with tissue-extracted RyR (e.g., isolated sarcoplasmic reticulum vesicles) or with suspensions of cells natively or recombinantly expressing RyR constructs (e.g., myocytes, HEK-293, etc.). The principles of fluorescence and FRET assays for RyRs have been described (Cornea et al., *Proc Natl Acad Sci USA*. 2009; 106:6128-6133; Cornea et al., *J Biol Chem*. 2010; 285:19219-19226.; Guo et al., *Circ Res*. 2010; 106:1743-1752; Guo et al., *Biophys J*. 2011; 101:2170-2177). However, high-throughput screening assays for RyR (or other intracellular channels) have not been described previously, and it was unclear if and how the principles of these FRET assays could be applied to design a feasible high-throughput screening campaign for the discovery of RyR modulators within large collections of small-molecule chemical compounds.

Provided herein are methods for identifying a compound that modulates an RyR molecule. In one embodiment, the method includes providing a complex that includes an RyR molecule, an FKBP, and a domain peptide, and contacting the complex with a test compound to form a mixture. The FKBP includes a donor probe, and the domain peptide includes an acceptor probe. The donor probe and the acceptor probe can be used for energy transfer. The method also includes measuring the fluorescence lifetime or intensity of the donor probe. A difference between the fluorescence lifetime or intensity in the presence of the test compound and the fluorescence lifetime or intensity in the absence of the test compound indicates that the test compound modulates RyR.

In another embodiment, the method includes providing a complex that includes an RyR molecule, an FKBP, and a modulatory protein, and contacting the complex with a test compound to form a mixture. The FKBP includes a donor probe, and the modulatory protein includes an acceptor probe. The donor probe and the acceptor probe can be used for energy transfer. The method also includes measuring the fluorescence lifetime or intensity of the donor probe. A difference between the fluorescence lifetime or intensity in the presence of the test compound and the fluorescence lifetime or intensity in the absence of the test compound indicates that the test compound modulates RyR.

In yet another embodiment, the method includes providing a complex that includes an RyR molecule, an FKBP, a domain peptide, and a modulatory protein, and contacting the complex with a test compound to form a mixture. The domain peptide includes a first chromophore, and the modulatory protein includes a second chromophore. The first chromophore and the second chromophore are a donor-acceptor pair such that energy transfer can occur between two chromophores. The method also includes measuring the fluorescence lifetime or intensity of the first or the second chromophore, wherein a difference between the fluorescence lifetime or intensity in the presence of the test compound and the fluorescence lifetime or intensity in the absence of the test compound indicates that the test compound modulates RyR.

In one embodiment, the RyR molecule used in the methods provided herein may be RyR1, RyR2, or RyR3. A non-limiting example of a domain peptide is DPc-10. Non-limiting examples of modulatory proteins include calmodulin, S100A1, and sorcin.

In one embodiment, the difference between the fluorescence lifetime in the presence of the test compound and the fluorescence lifetime in the absence of the test compound is a ΔE of greater than 3 times the ΔE standard deviation of a control. In one embodiment, the measuring includes high throughput screening.

In one embodiment, the concentration of the FKBP is at, or within one order of magnitude, of the $K_d$ of the FKBP for the RyR molecule. In one embodiment, the concentration of the domain peptide is at, or within one order of magnitude, of the $K_d$ of the domain peptide for the RyR molecule. In one embodiment, the concentration of the modulatory protein is at, or within one order of magnitude, of the $K_d$ of the modulatory protein for the RyR molecule.

In one embodiment, the concentration of the FKBP is a saturating concentration. In one embodiment, the concentration of the domain peptide is a saturating concentration. In one embodiment, the concentration of the modulatory protein is a saturating concentration.

In one embodiment, the complex is present in a permeabilized cell. In one embodiment, the complex is present in a purified membrane.

In one embodiment, the mixture includes a compound that mimics the environment present in dystrophic or heart failure myocytes and results in, for instance, a pathological condition. Examples of a pathological condition include, for instance, heart failure and lethal arrhythmia such as catecholaminergic polymorphic ventricular tachycardia. Examples of compounds include, but are not limited to, $H_2O_2$ and oxidized glutathione.

As used herein, the terms "RyR channel," "RyR molecule," and "RyR protein" refer to the ryanodine receptor homotetrameric channel.

The terms "modulate" and cognates thereof refer to the capacity to alter a measurable biological activity, e.g., interactions between different RyR domains, movement of $Ca^{2+}$ through the RyR channel, interactions between RyR and other binding partners such as domain peptides, FKBP, modulatory proteins (e.g., calmodulin, S100A1, and sorcin), and variants of ryanodine (e.g., unlabeled or fluorescently labeled). Altered biological activity may be the result of altering the secondary and/or tertiary structure of an RyR protein.

As used herein, RyR "biological activity" or "activity" refers to a function of an RyR channel, e.g., interactions between different RyR domains, movement of $Ca^{2+}$ through the RyR channel, interactions between RyR and other binding partners such as domain peptides, FKBP, modulatory proteins (e.g., calmodulin, S100A1, and sorcin), and variants of ryanodine (e.g., unlabeled or fluorescently labeled). Inhibition of RyR activity refers to inhibition of a pathological state of an RyR channel, for instance, a decrease in the movement of $Ca^{2+}$ compared to an appropriate control, a decrease in access of a domain peptide to a specific site on an RyR channel, an increase in the binding of a modulatory protein to an RyR channel, an increase in the binding of a ryanodine variant, and the like.

As used herein, the term "wild-type" refers to the most typical form of an organism, protein, or characteristic as it occurs in nature.

As used herein, the term "protein" refers broadly to a polymer of two or more amino acids joined together by peptide bonds. The term "protein" also includes molecules which contain more than one protein joined by disulfide bonds, ionic bonds, or hydrophobic interactions, or complexes of polypeptides that are joined together, covalently or noncovalently, as multimers (e.g., dimers, tetramers). Thus, the terms peptide, oligopeptide, and polypeptide are all included within the definition of protein and these terms are used interchangeably. It should be understood that these terms do not connote a specific length of a polymer of amino acids, nor are they intended to imply or distinguish whether the protein is produced using recombinant techniques, chemical or enzymatic synthesis, or is naturally occurring.

As used herein, the terms "FRET," "fluorescence resonance energy transfer," "Forster resonance energy transfer" and "resonance energy transfer" are used interchangeably, and refer to an energy transfer process that occurs between two chromophores.

As used herein, a "chromophore" is a molecule that interacts with another chromophore so as to be useful for FRET. A chromophore may be monomeric or multimeric molecule, such as a protein, organic molecule, or combinations thereof. Chromophores suitable for use in a FRET assay are known to the skilled person and are readily available. In one embodiment, a chromophore may be a donor (also referred to as a donor probe). A donor probe refers to a molecule that will absorb energy and then re-emit at least a portion of the energy over time. In one embodiment, a chromophore may be an acceptor (also referred to as an acceptor probe). An acceptor probe refers to a molecule that will also absorb energy and then re-emit at least a portion of the energy over time, however, the energy absorbed by the acceptor is predominantly the energy re-emitted by the donor probe. Thus, provided that a donor probe and an acceptor probe are physically located sufficiently close (most often within 2.5 to 12 nm), the two probes function together and, upon excitation with an appropriate wavelength, the donor probe transfers a precise amount of energy to the acceptor probe. This process can be specifically and quantitatively detected by observing the decrease in donor fluorescence intensity or lifetime or, in some cases, also the energy re-emitted by the acceptor probe as fluorescence. Thus, FRET assays are typically used to measure (1) the mole fraction of donors coupled with acceptor (e.g., to determine the binding affinity between the donor-labeled and acceptor-labeled molecules) and (2) the distance and/or distance changes between donor and acceptor.

As used herein, the term "F" refers to a fluorescent label. For instance, F-DPc10 refers to a DPc10 molecule with an attached fluorescent label. As used herein, the term "D" refers to a donor chromophore. For instance, D-FKBP refers to an FKBP molecule with an attached donor chromophore. As used herein, the term "A" refers to an acceptor chromophore. For instance, A-DPc10 refers to a DPc10 molecule with an attached acceptor chromophore.

As used herein, the term "high-throughput screening" or "HTS" refers to a method drawing on different technologies and disciplines, for example, optics, chemistry, biology or image analysis to permit rapid analysis of multiple samples at rates that permit highly parallel biological research and drug discovery.

As used herein, an "isolated" protein is one that has been either removed from its natural environment, produced using recombinant techniques, or chemically or enzymatically synthesized. For instance, an isolated protein is a protein that has been removed from the cytoplasm or from the membrane of a cell, and many of the proteins, nucleic acids, and other cellular material of its natural environment are no longer present.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

μmol/L DPc10 (3 hours, 25° C.) before adding CaM. B, Quantitative analysis of data from (A) for 20 and 500 nmol/L CaM. Data are reported as mean±standard error (SE). C, Confocal images illustrating FRET between AF568-110-CaM (donor) and HF647-DPc10 (acceptor) measured using the acceptor photobleaching method. Photobleached area is clearly delineated in the middle of the myocyte image. D, Dependence of AF568-110-CaM fluorescence intensity on the extent of HF647-DPc10 photobleach. Data are best fitted by a linear function ($R^2$=0.986), indicating that each donor participates in FRET with only 1 acceptor. E, Summary of FRET efficiency E and distances between AF568-110-CaM and HF647-DPc10, and between AF488-34-CaM and HF647-DPc10 derived from FRET. Data are reported as mean±SE.

Figure 19:
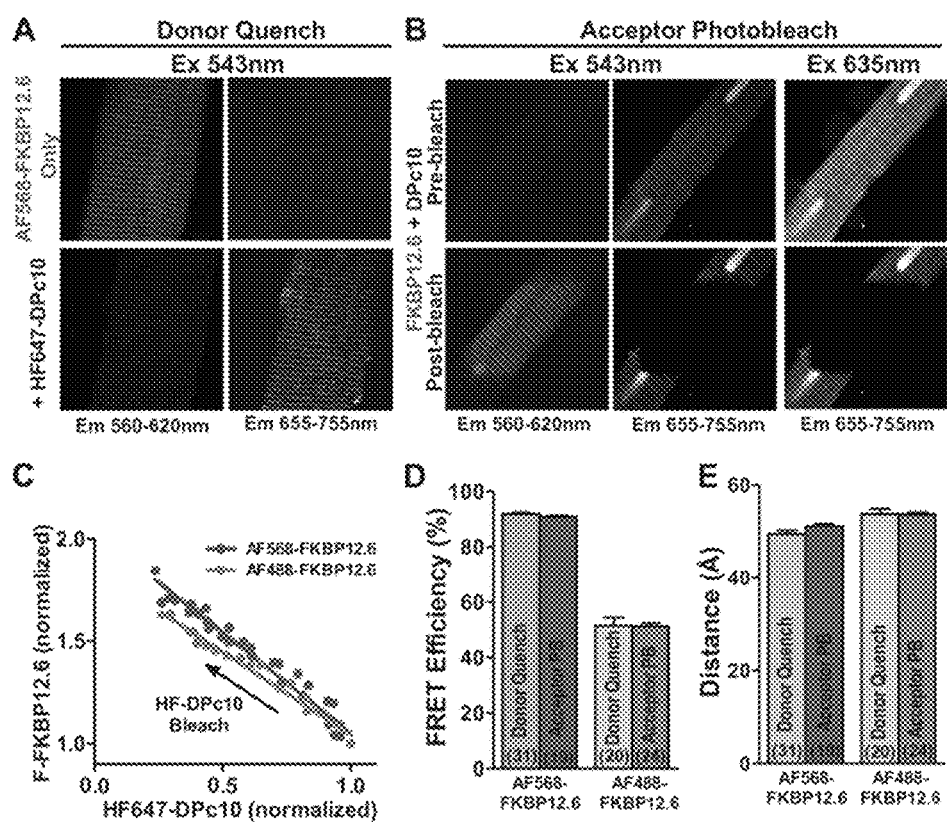

FIG. 19. Fluorescence resonance energy transfer (FRET) between FK506-binding binding protein (FKBP12.6) labeled with AF568 or AF488 (donor) and HF647-DPc10 (acceptor) in permeabilized cardiomyocytes. A, Confocal images showing FRET as the decrease in AF568-FKBP12.6 fluorescence (donor quench) on addition of HF647-DPc10. B, Confocal images illustrating FRET as the increase in AF568-FKBP12.6 fluorescence after photobleaching HF647-DPc10. Acceptor photobleach is clear in the center of the confocal myocyte image. C, Dependence of AF568-FKBP12.6 and AF488-FKBP12.6 fluorescence intensity on the extent of HF647-DPc10 photobleaching. Data are best fit by a linear function ($R^2$=0.966 for AF568-FKBP12.6, $R^2$=0.972 for AF488-FKBP12.6), indicating that each donor participates in FRET with only 1 acceptor. D and E, Summary of E and distances between AF568-FKBP12.6/AF488-FKBP12.6 and HF647-DPc10 based on FRET measured by donor quench and acceptor photobleach. Data are reported as mean±standard error.

Figure 20:
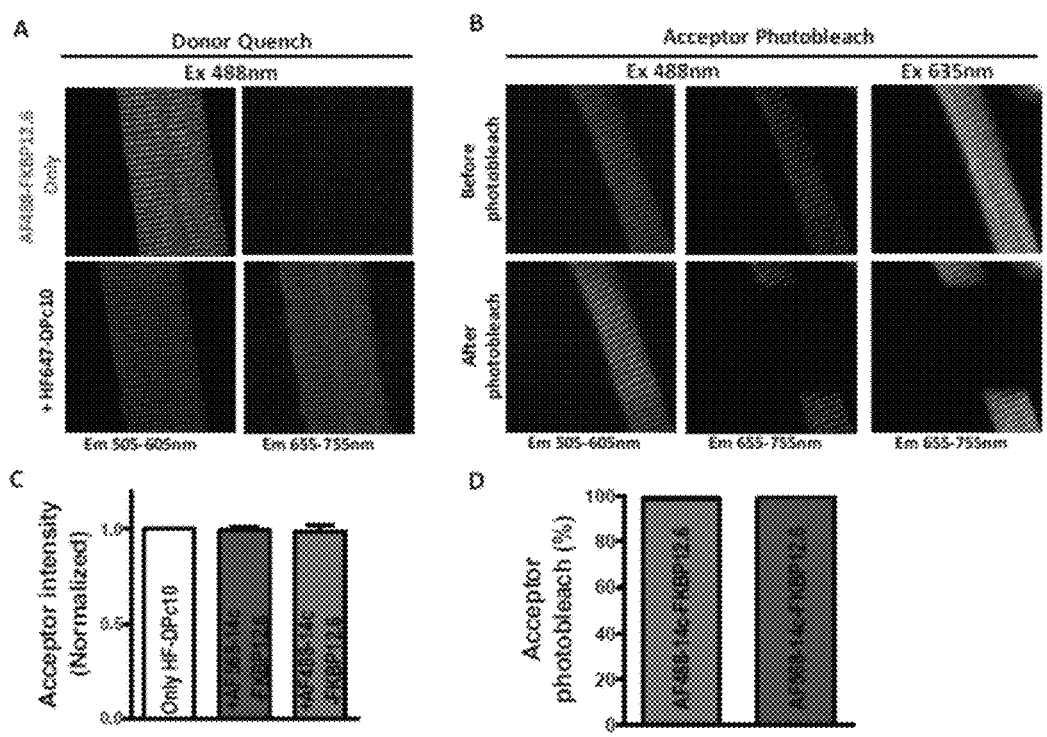

FIG. 20. A. Representative image of AF488-FKBP12.6 quench following addition of HF647-DPc10. B. Confocal images showing AF488-FKBP12.6 and HF647-DPc10 fluorescence before and after acceptor photobleaching from permeabilized myocytes. C. Summarized data of acceptor (HF647-DPc10) fluorescence intensity with or without equilibrated donors which was normalized to without donor condition. D. The extent of the acceptor photobleaching in both cases (AF488-FKBP12.6 and AF568-FKBP12.6).

Figure 21:
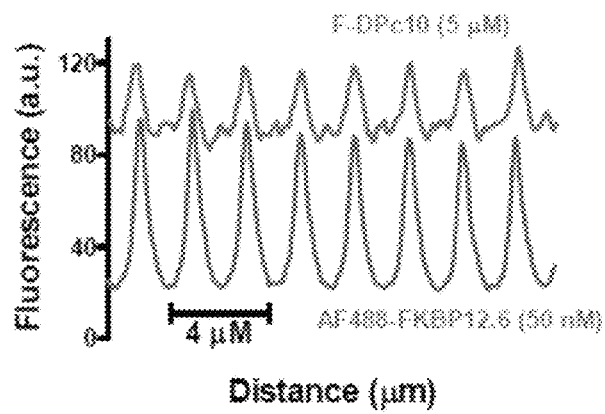

FIG. 21. Plot profile of striated sarcomeric pattern shows both F-DPc10 (5 μmol/L) binding and AF488-FKBP12.6 (50 nmol/L) binding at Z-lines and M-lines.

Figure 9:
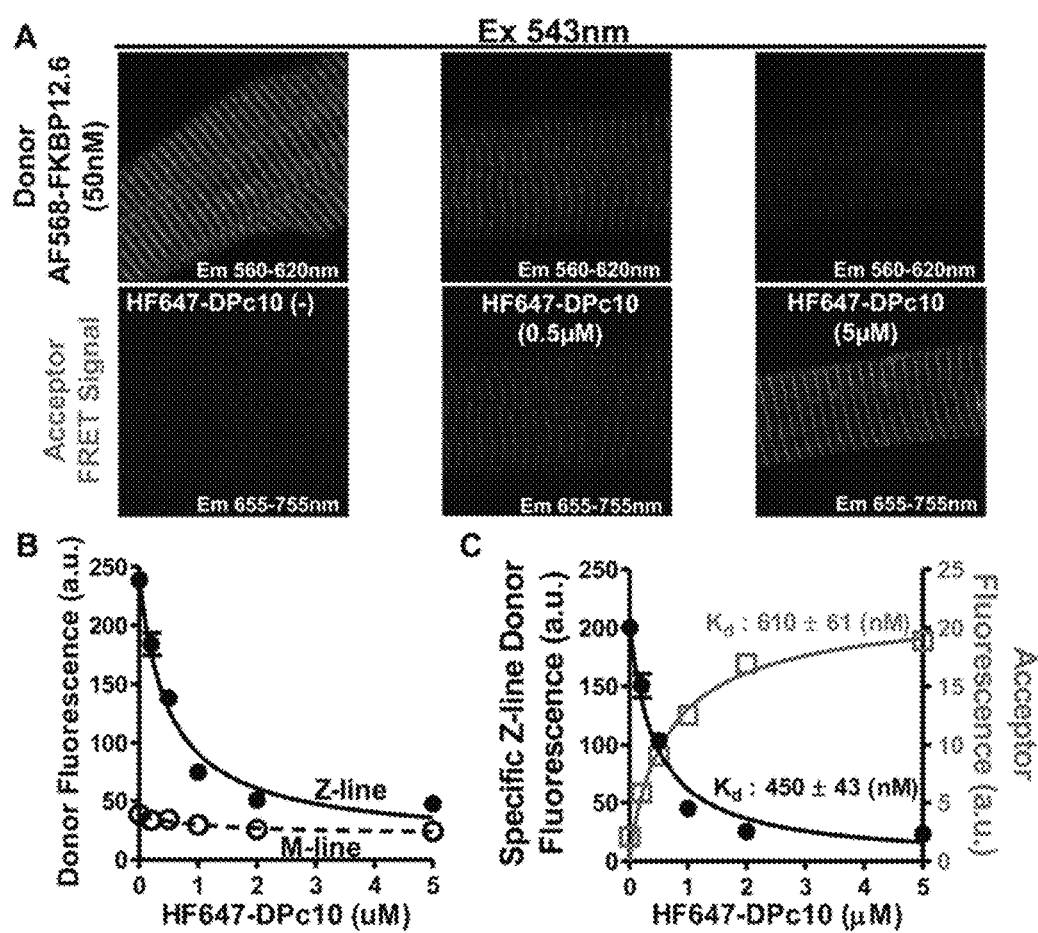
FIG. 9. Steady-state dissociation constant ($K_d$) measurement of DPc10 by using fluorescence resonance energy transfer (FRET) between FK506-binding protein 12.6 (FKBP12.6) labeled with AF568 (donor) and HF647-DPc10 (acceptor) in permeabilized cardiomyocytes. A, Confocal images of FRET with decrease of AF568-FKBP12.6 fluorescence (donor quench) on addition of 0.5 and 5 µmol/L HF647-DPc10. B, Donor fluorescence intensity (arbitrary units [a.u.]) from Z-line and M-line plotted vs [HF647-DPc10]. C, FRET as a result of HF647-DPc10 (acceptor) binding was detected at the Z-line ($F_Z$-$F_M$) either as decrease in donor fluorescence or as an enhancement in acceptor fluorescence. Data are reported as mean±standard error.
Figure 10:
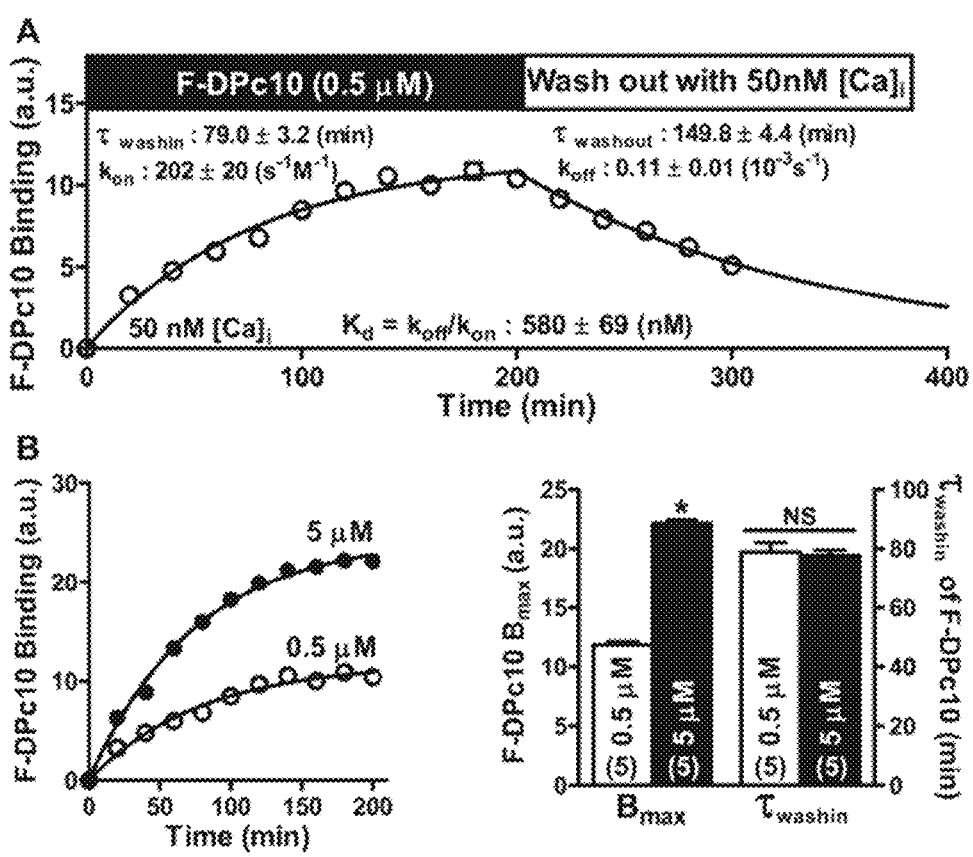
FIG. 10. Kinetics of fluorescent DPc10 (F-DPc10) binding at the myocyte Z-line. A, Time course of F-DPc10 (0.5 µmol/L) wash-in and washout. B, Effect of [F-DPc10] (0.5 and 5 µmol/L) on $\tau_{wash-in}$ and $B_{max}$. Data are reported as mean±standard error.
Figure 13:
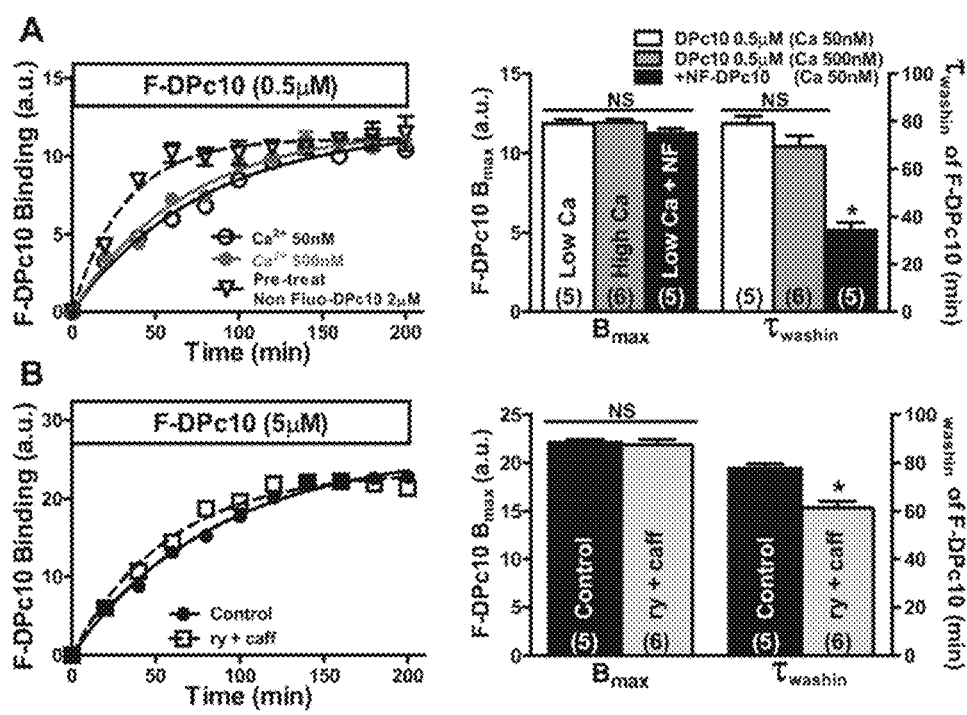
FIG. 13. Effect of cardiac ryanodine receptors (RyR2) channel modulators on the kinetics of fluorescent DPc10 (F-DPc10) Z-line association. A, Time course of F-DPc10 (0.5 µmol/L) Z-line binding in internal solution containing low $[Ca^{2+}]_i$ or high $[Ca^{2+}]_i$, or after a 3-hour pre-equilibration with saturating [NF-DPc10] (2 µmol/L) in low $[Ca^{2+}]_i$ (triangles). Data are reported as mean±standard error (SE). B, Time course of F-DPc10 (5 µmol/L) Z-line binding after a 3-hour pre-equilibration in internal solution containing ryanodine (100 µmol/L) and caffeine (5 µmol/L). Data are reported as mean±SE (n values on bars; a.u., arbitrary units).
Figure 18:
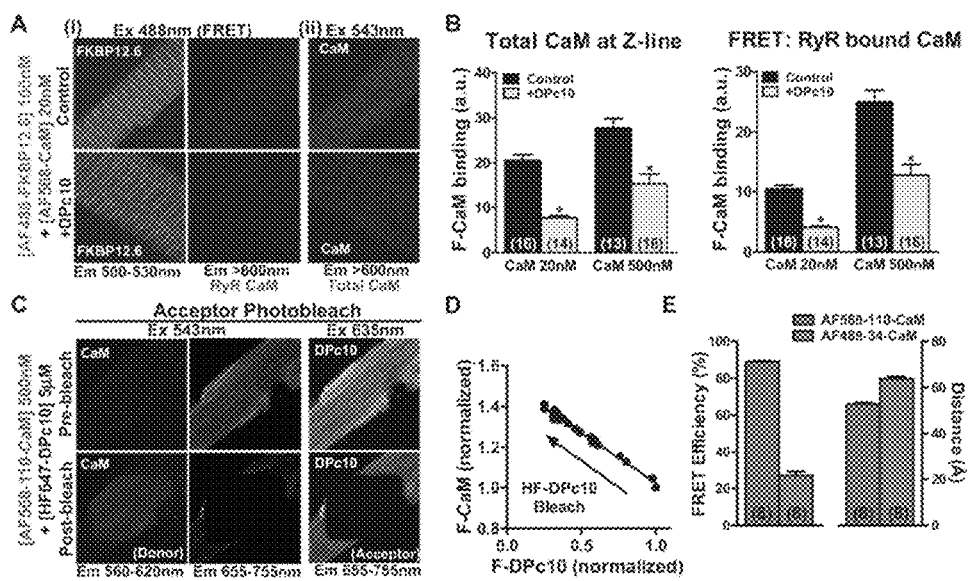
FIG. 18. The effect of DPc10 on calmodulin (CaM) and FK506-binding protein 12.6 (FKBP12.6) binding to cardiac ryanodine receptors (RyR2) in cardiac myocytes. A, Representative confocal image of the effect of DPc10 on AF568-CaM binding at the Z-lines (ii, Ex=543 nm) and at the RyR2 detected by fluorescence resonance energy transfer (FRET) between AF488-FKBP12.6 (donor) and AF568-CaM (acceptor) (i, Ex=488 nm). Myocytes were incubated with 5
Figure 22:
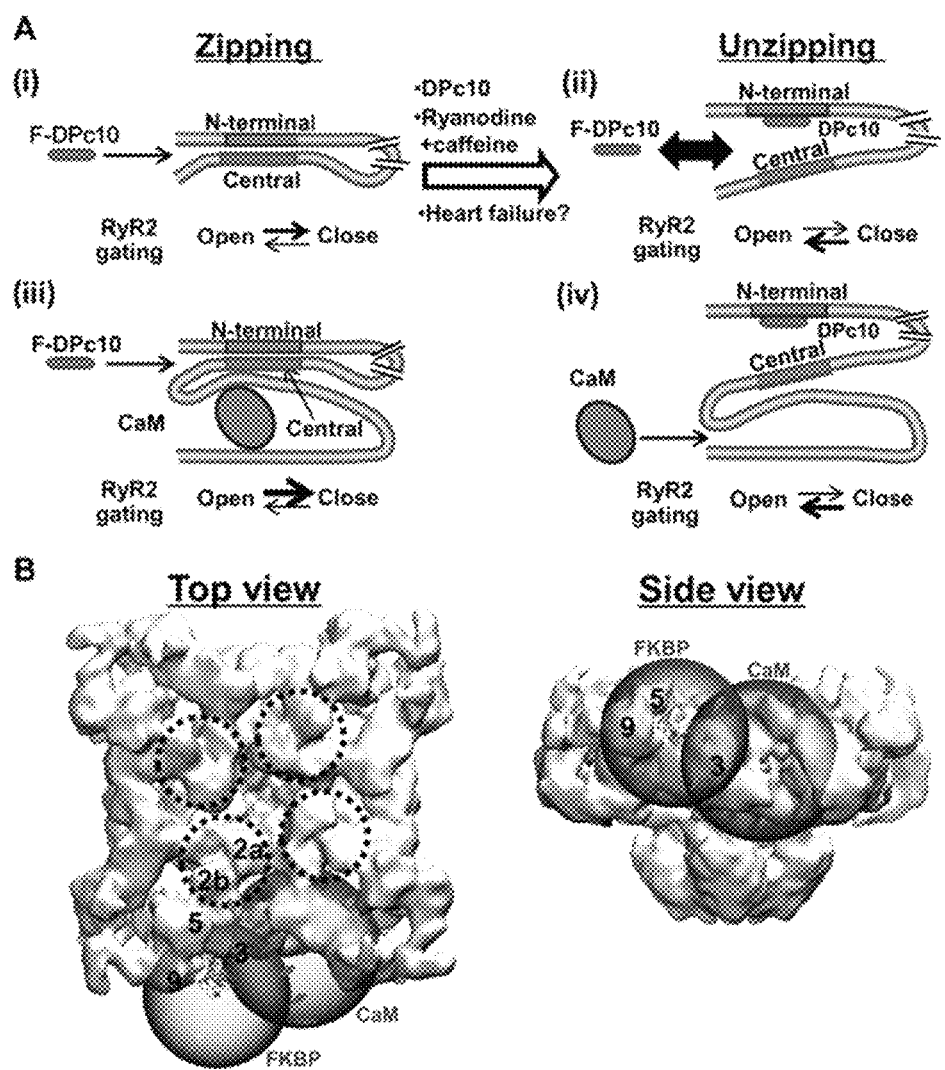

FIG. 22. Proposed model of the interaction between N-terminal and central domains, and localization of the DPc10-binding site in the 3-dimensional (3D) structure of cardiac ryanodine receptors (RyR2). A, Kinetic results (FIGS. 9, 10, and 13) suggest that fluorescent DPc10 (F-DPc10) access to its binding site is controlled by interdomain interaction within RyR2. i, The F-DPc10 access is sterically hindered in resting normal RyR2 (zipped state). ii, Pretreatment of RyR2 with physiological, pharmacological, or disease-mimetic agents that promote unzipping increase the F-DPc10 association rate. iii, Calmodulin (CaM) inhibits the F-DPc10 binding to RyR2. iv, DPc10 binding to RyR2 inhibits CaM binding to RyR2. B, Localization of DPc10 in the 3D structure of RyR2. Fluorescence resonance energy transfer (FRET) data between CaM and DPc10 (FIG. 18) and between FK-binding protein (FKBP) and DPc10 (FIG. 19) suggest that DPc10 binds near to, or within, the RyR handle domain, between FKBP12.6 and CaM. The transparent sphere to the right is centered at the surface projection (opaque blue ball) of the mass center of the cryo-EM CaM density (Samsó et al., J Biol Chem. 2002; 277:1349-1353) and has a radius of 58 Å (FIG. 18E). The transparent sphere to the left is centered at position 14 of FKBP (Samsó et al., J Mol Biol. 2006; 356:917-927) (indicated by the opaque ball) and has a radius of 53 Å (FIG. 19E). The intersection of a sphere skin with the RyR surface defines possible locations of the DPc10 acceptor within the RyR 3D structure. In the top view, we note that the FKBP sphere intersects the clamp domain. The dashed black circles approximately delineate the cryo-EM densities where the atomic structure of the skeletal muscle RyR domain 1-559 was previously docked (Tung et al., Nature. 2010; 468:585-588). In the side view, the intersection continues through the clamp but also through domain 3. The locus of the DPc10 should be approximately at the intersections between the spheres (green arrows) and the RyR surface.

Figure 23:
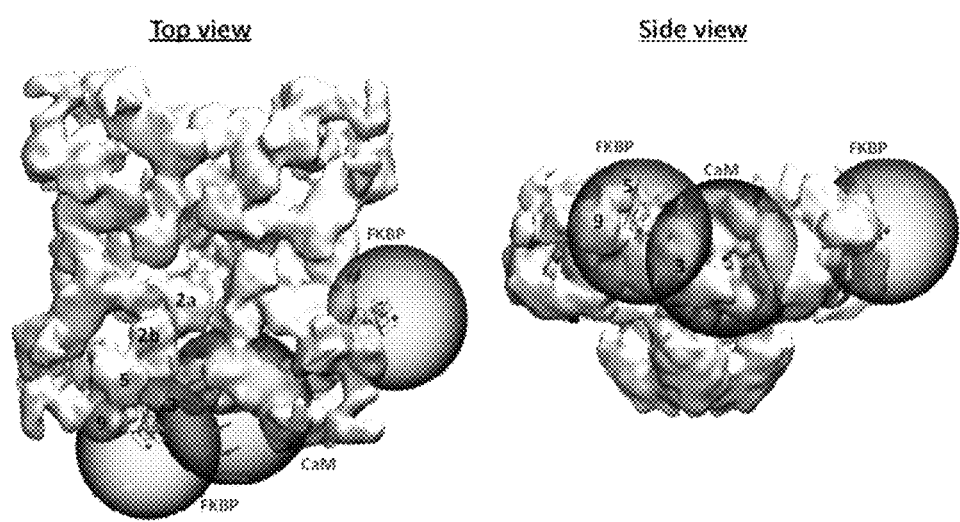

FIG. 23. Variant of FIG. 7B to better illustrate the location of the DPc10 acceptor within the RyR cryo-EM map, as suggested by FRET measurements from FKBP and CaM donors. The CaM-centered sphere (blue, R=58 Å) is flanked by two FKBP-centered spheres (red, R=53 Å)—one on the same face as the shown CaM, and the other one on an adjacent face. Spheres are of radii calculated from FRET, which indicate the distance between the donors at FKBP or CaM and the acceptor at DPc10). The FKBP and CaM spheres on the same face of the RyR clearly intersect along a circle (arrowheads indicating the portion that is not buried within the RyR map) that meets the RyR density map to delineate the locus of the DPc10 acceptor (green arrowhead). However, the FKBP and CaM spheres on adjacent faces of the RyR are separated by more than 20 Å (distance of closest approach indicated by magenta arrow in Top View), suggesting that the DPc10 donor does not locate in domains 5 or 9.

Figure 24:
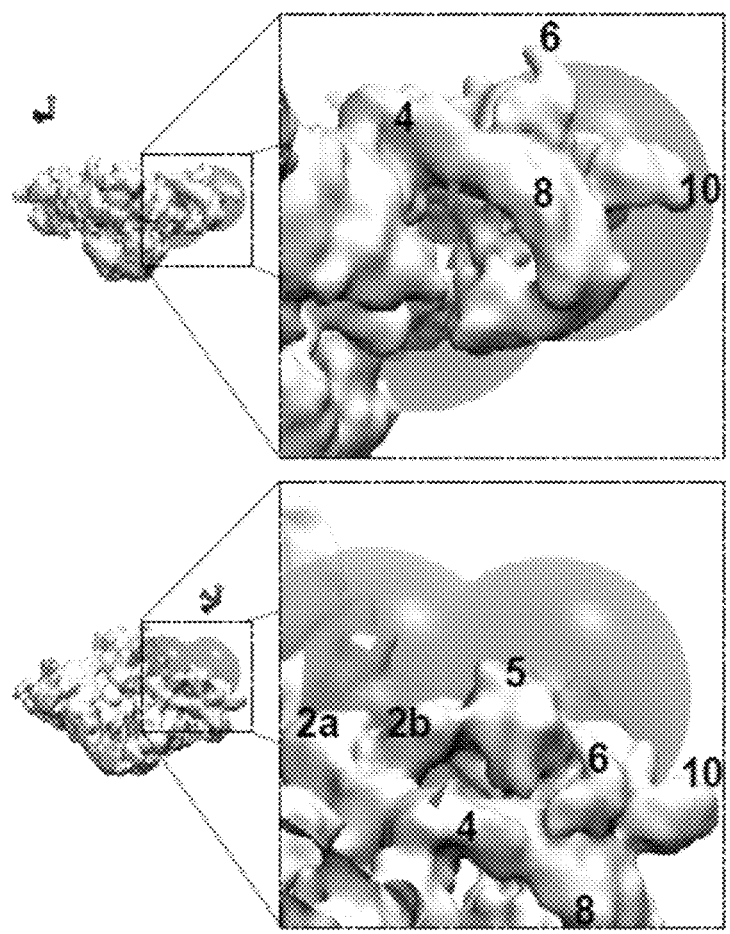

FIG. 24. Sight-lines via galleries formed between the peripheral RyR domains 3, 8, 9, and 10, and the more central domains 2 and 4 allow viewing the HF647-DPc10 locus along the inside face of domain 3.

Figure 25:
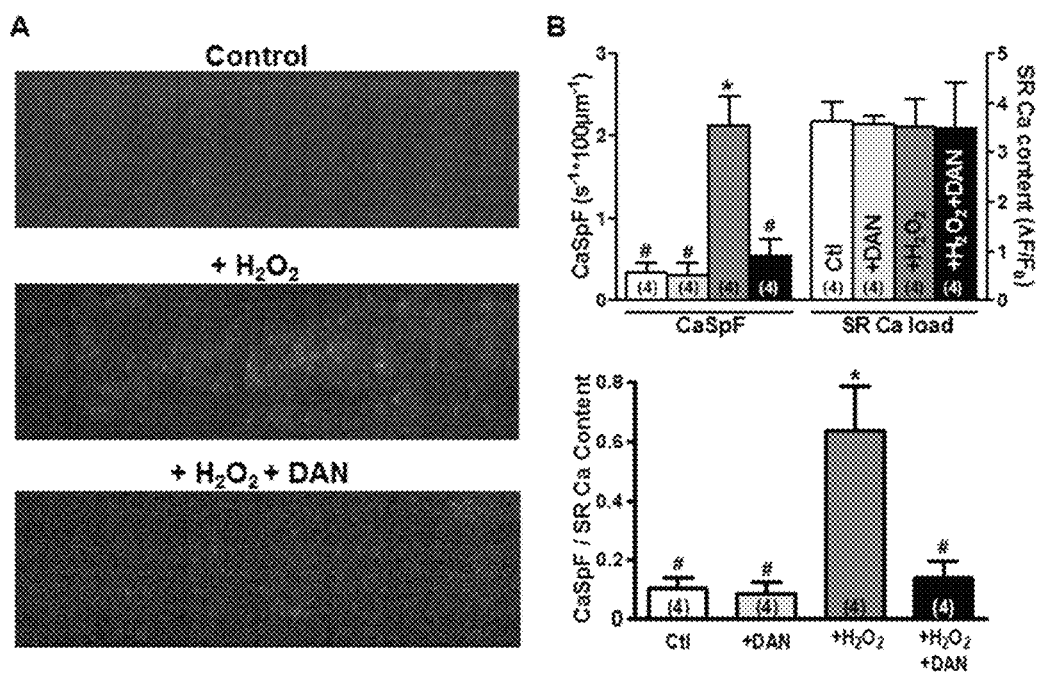

FIG. 25. Effects of $H_2O_2$ and dantrolene on $Ca^{2+}$ sparks and SR $Ca^{2+}$ content in intact myocytes. $Ca^{2+}$ sparks and SR $Ca^{2+}$ content were measured in myocytes treated with $H_2O_2$ (50 μmol/L), dantrolene (DAN; 1 μmol/L), and a combination of $H_2O_2$ and dantrolene. A, Representative line-scan images of $Ca^{2+}$ sparks. B, Summarized data of CaSpF and SR $Ca^{2+}$ content. Data are reported as mean±SE *P<0.05 vs. Control, #P<0.05 vs. $H_2O_2$.

Figure 26:
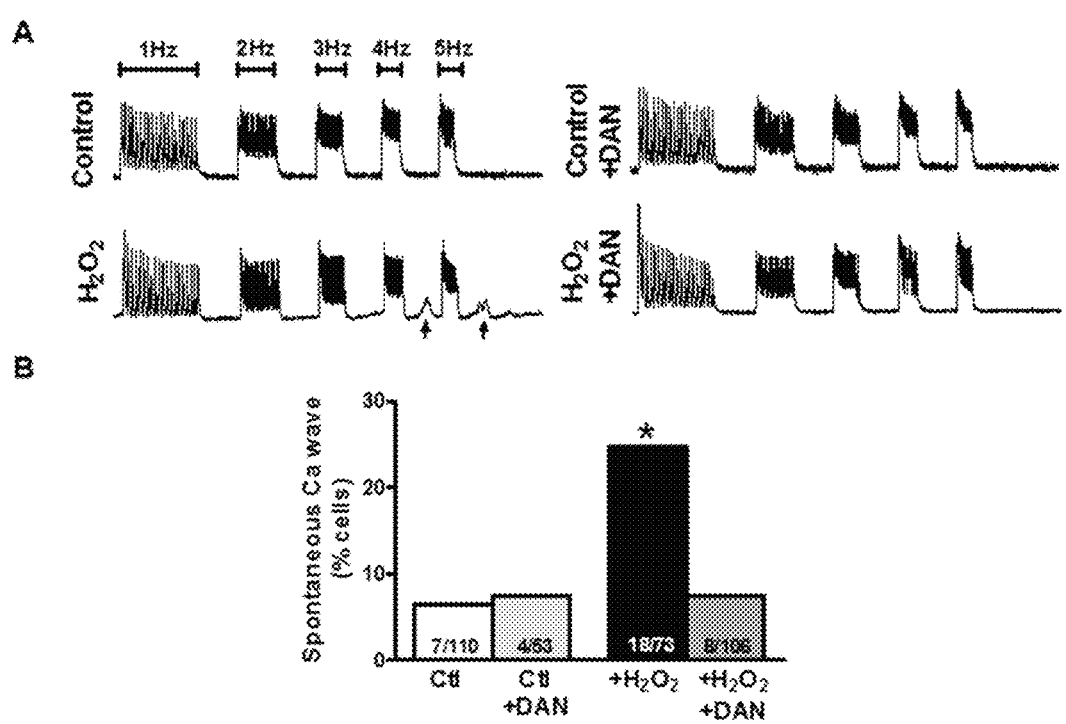

FIG. 26. Arrhythmogenic spontaneous $Ca^{2+}$ waves (SCW) following treatment with $H_2O_2$ in intact myocytes. A, Treatment with $H_2O_2$ led to an increased incidence of SCW (arrows), but dantrolene (DAN) prevented SCW. Representative time-plots of intracellular $Ca^{2+}$ during pacing. B, Summary of % occurrence of SCW. Numbers inside the bars indicate cells with SCW/total cells studied for each group. *P<0.05 vs. Control, Fisher's exact test.

Figure 27:
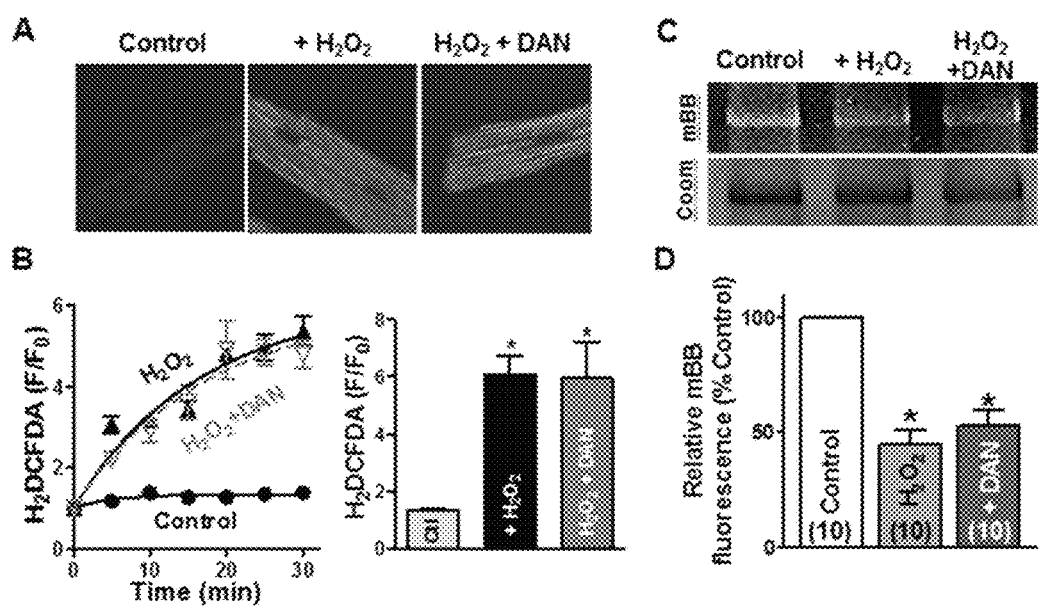

FIG. 27. Oxidation status of the intracellular environment and RyR2. A, Representative confocal images of control, $H_2O_2$ (50 μmol/L), and $H_2O_2$ (50 μmol/L)+DAN (1 μmol/L) loaded with an ROS-sensitive fluorescent indicator $H_2$DCFDA. B, Time course of $H_2$DCFDA fluorescence recorded under the same condition as indicated for panel A (left), and quantitative analysis of the $H_2$DCFDA fluorescence intensity at equilibrium for each condition (right). C, Representative RyR2-bound mBB fluorescence intensity (upper strip) and Coomassie-stained gels (lower strip) of RyR2 measured under control conditions, +$H_2O_2$ (50 μmol/L), or +$H_2O_2$ (50 μmol/L)+DAN (1 μmol/L) treatment. D, Relative free thiol content of RyR2 (indicated by mBB fluorescence) normalized by the corresponding intensity of the Coomassie-stained RyR2 band. Data are reported as mean±SE. DAN: dantrolene.

Figure 28:
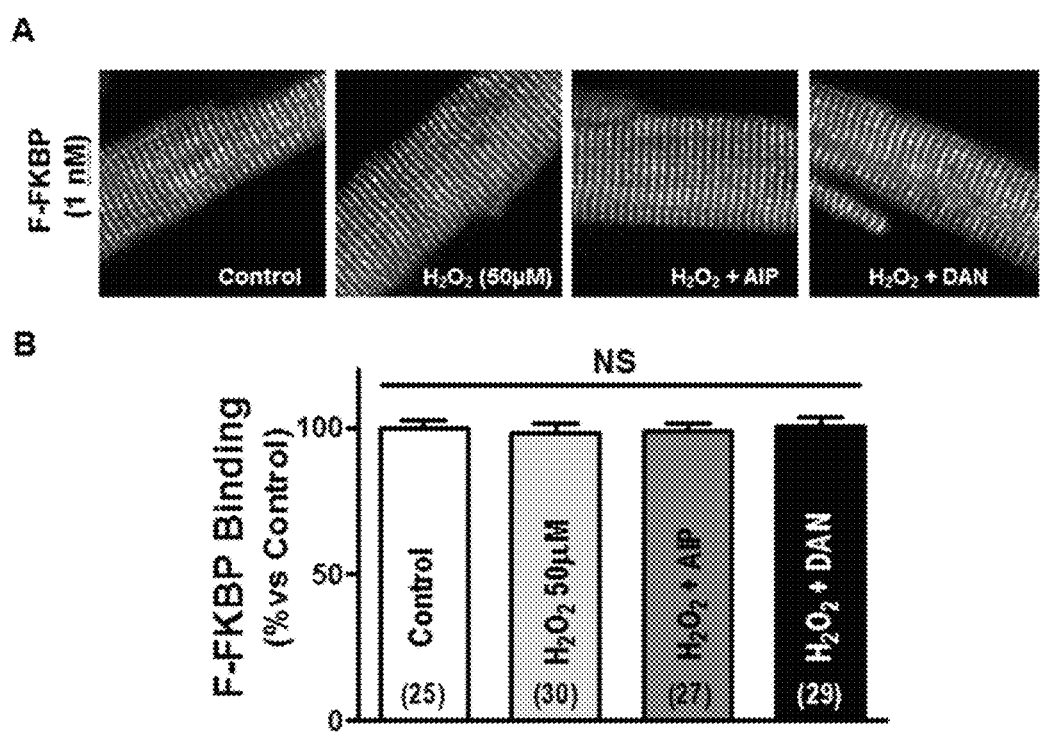

FIG. 28. Effect of $H_2O_2$ (50 µmol/L) on FKBP12.6 binding at the Z-line. A, Representative confocal images of saponin-permeabilized myocytes incubated with F-FKBP (1 nM/L), which were exposed to $H_2O_2$ (50 µmol/L), $H_2O_2$ (50 µmol/L) +AIP (1 µmol/L) or $H_2O_2$ (50 µmol/L) +DAN (1 µmol/L). B, Summary of the F-FKBP Z-line binding corresponding to the experiment in panel A. Data are reported as mean±SE. DAN: dantrolene.

Figure 29:
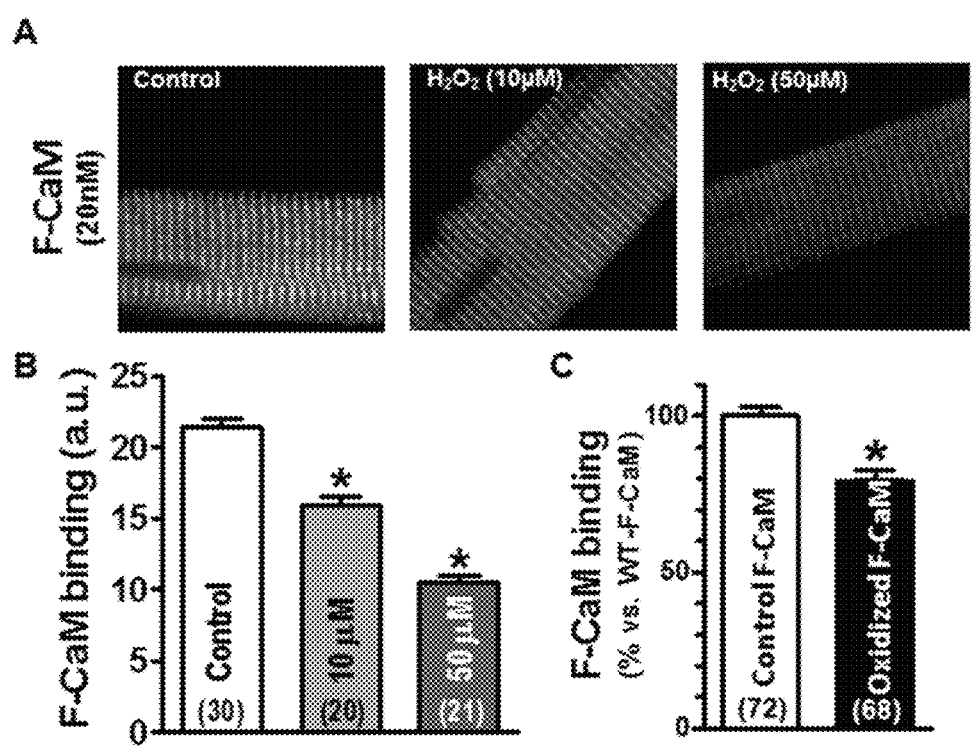

FIG. 29. Effect of $H_2O_2$ on calmodulin (CaM) binding at the Z-line. A, Representative confocal images illustrating the effect of myocyte oxidation by $H_2O_2$ on F-CaM binding at the Z-lines. $H_2O_2$ was applied to the bath 1 hour before beginning to image and was present throughout the experiment. B, Quantitative analysis of data from A. C, Effect of F-CaM oxidation on binding at the Z-line. F-CaM was pre-incubated in $H_2O_2$, then applied to the myocyte bath under control conditions. Data are reported as mean±SE. *p<0.001 vs. control.

Figure 30:
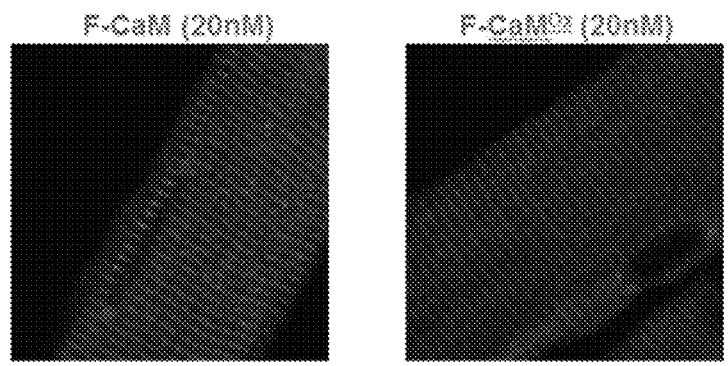

FIG. 30. Representative myocyte confocal images illustrating decreased Z-line binding of oxidized relative to unoxidized F-CaM.

Figure 31:
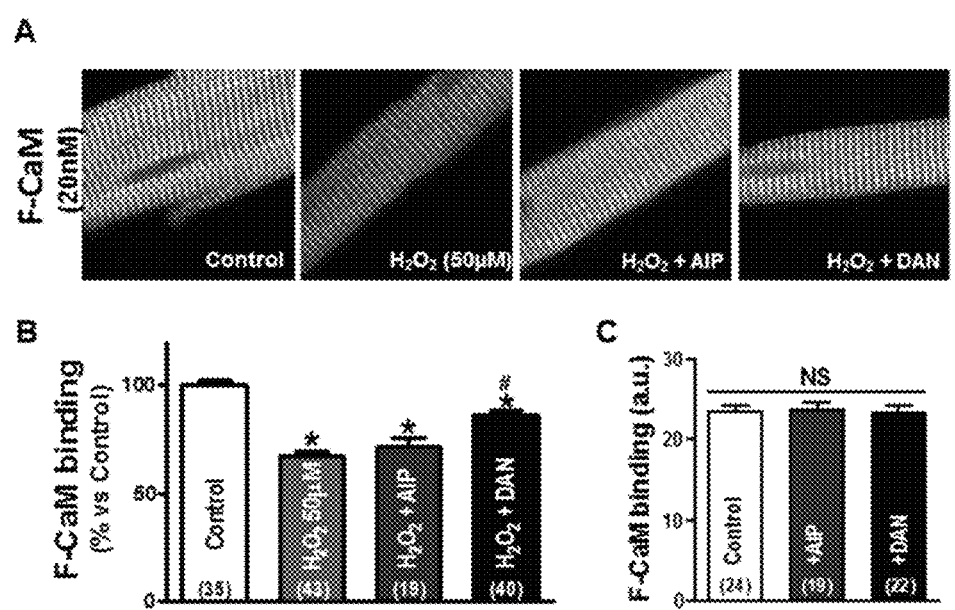

FIG. 31. Effects of RyR2 oxidation on calmodulin (CaM) binding at the Z-line. $H_2O_2$ was applied to the myocyte bath 1 hour before beginning the recording, and was removed before the applying the F-CaM. A, Representative confocal images of the effects of $H_2O_2$, $H_2O_2$+AIP, and $H_2O_2$+dantrolene on the F-CaM binding at the Z-lines. B, Quantitative analysis of data from A. C, Effect of AIP and DAN in on F-CaM Z-line binding in control myocyte. Data are reported as mean±SE. *p<0.001 vs. control, #p<0.001 vs. $H_2O_2$. DAN: dantrolene.

Figure 32:
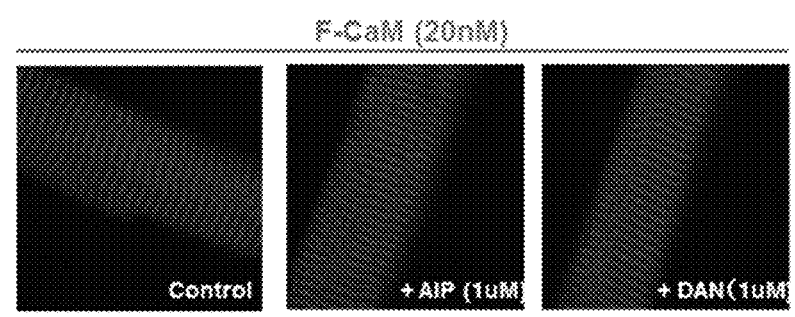

FIG. 32. Representative confocal images of the effects of AIP, and dantrolene (DAN) on F-CaM binding at the myocyte Z-line under control conditions (no $H_2O_2$).

Figure 33:
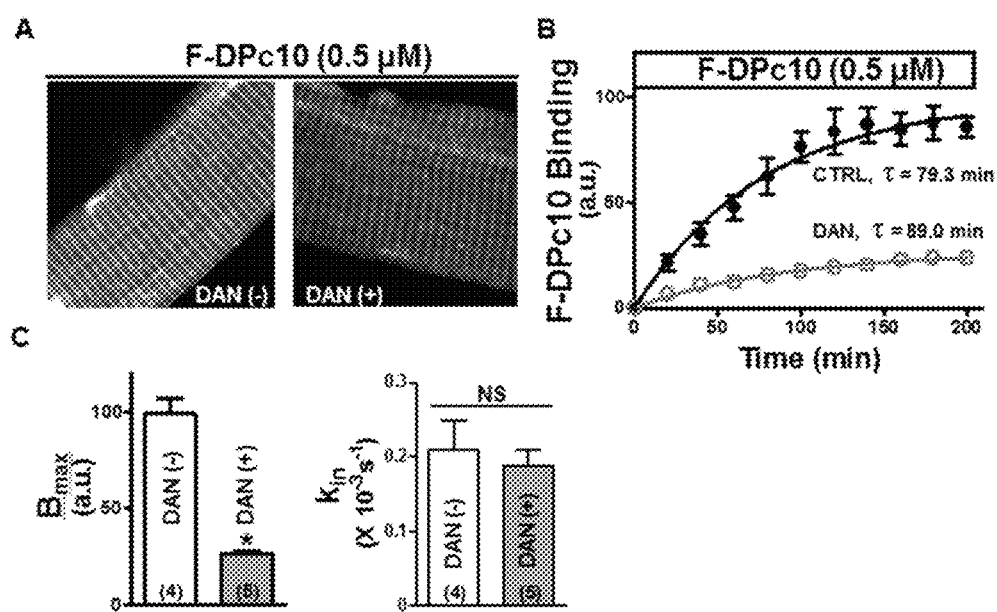

FIG. 33. Effect of dantrolene (DAN) (1 µmol/L) on F-DPc10 (0.5 µmol/L) binding at Z-line. A, Representative confocal images illustrating the effect of dantrolene (1 µmol/L) on the F-DPc10 (0.5 µmol/L) binding at the Z-lines. B, Time course of F-DPc10 (0.5 µmol/L) wash-in (full circles), and in the presence of dantrolene (1 µmol/L, open circles). C, Summary of $B_{max}$ and $k_{in}$ for the data in panel B. Data are reported as mean±SE.

Figure 34:
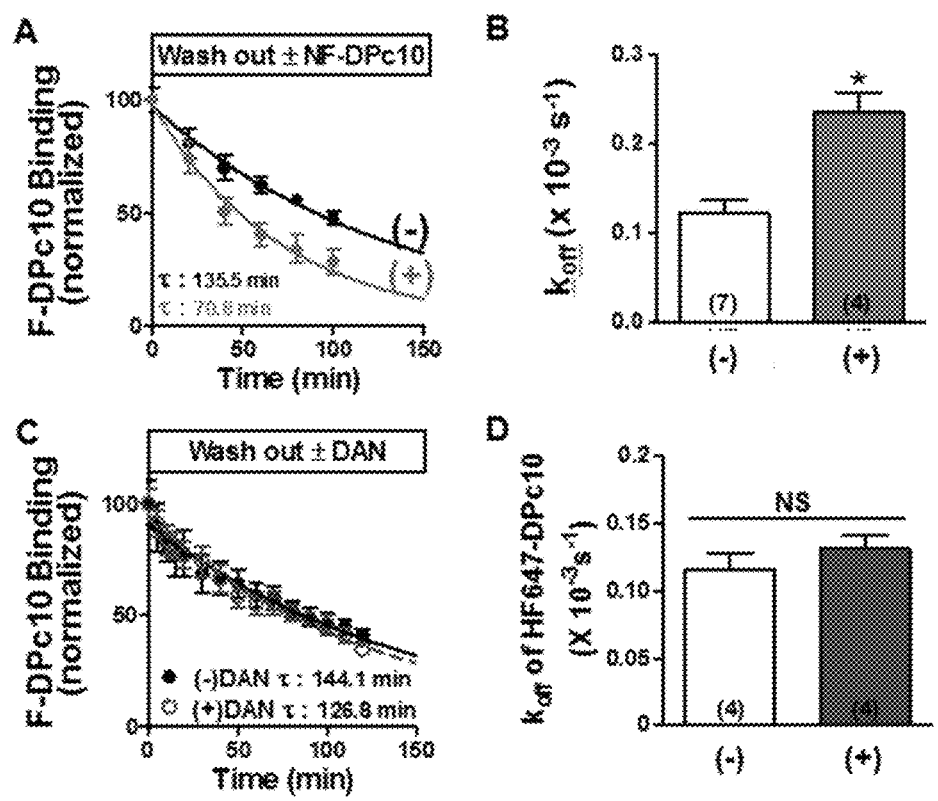

FIG. 34. Effects of non-fluorescent DPc10 (NF-DPc10) and dantrolene (DAN) on the time-course of F-DPc10 (0.5 µmol/L) wash-out. A, Time-course of F-DPc10 with (+) or without (−) NF-DPc10 (5 µmol/L). B, Summary of the $k_{off}$ values corresponding to the data in panel A. C, Time-course of F-DPc10 (0.5 µmol/L) wash-out under control conditions (−) and after treatment with DAN (1 µmol/L, +). D, Summary of the $k_{off}$ for the data in panel C. Data are reported as mean±SE.

Figure 35:
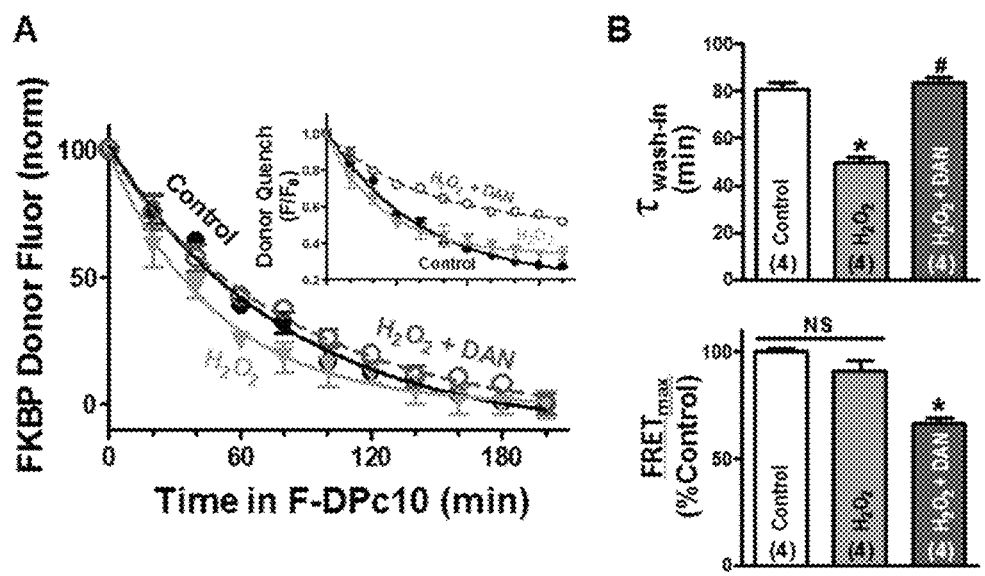

FIG. 35. Effects of $H_2O_2$ and dantrolene (DAN) on the F-DPc10 wash-in kinetics, detected via FRET between F-FKBP (donor) and F-DPc10 (acceptor). A, FRET, detected as donor quenching in myocytes pre-equilibrated with $H_2O_2$ (50 µmol/L) or $H_2O_2$ (50 µmol/L) +DAN (1 µmol/L). B, Summary of $\tau_{wash-in}$ and $FRET_{max}$ corresponding to the data in panel A. Data are reported as mean±SE. *p<0.001 vs. control, #p<0.001 vs. $H_2O_2$.

Figure 36:
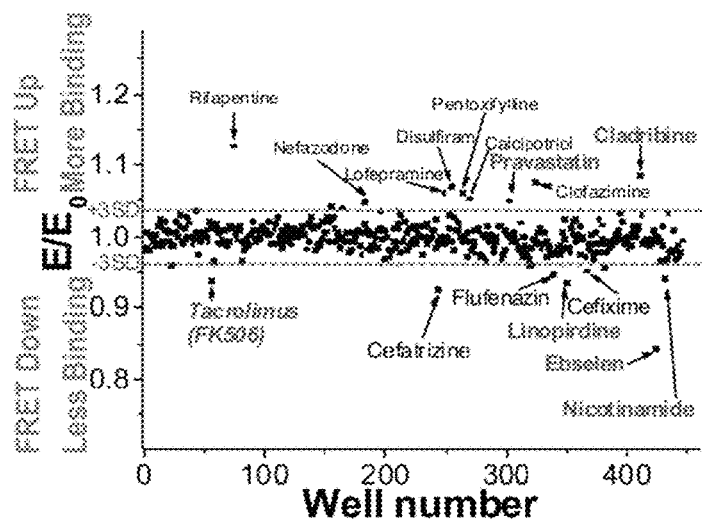

FIG. 36. Pilot screen of NIH Clinical Collection 1. This method picked up FK506 and several compounds that alter intracellular $Ca^{2+}$ cycling (Pravastatin, Cladribine, Linopirdine, Ebselen, and Nicotinamide). $E/E_0$, E(compound)/E (control); dotted line, 3SD threshold.

DETAILED DESCRIPTION OF ILLUSTRATIVE EMBODIMENTS

Provided herein are methods for identifying compounds that modulate a ryanodine receptor (RyR) intracellular $Ca^{2+}$ release channel. Calcium plays a central role in muscle contraction. In muscle contraction, $Ca^{2+}$ is released through the RyR from the sarcoplasmic reticulum (SR) intracellular reservoir, then pumped back into the SR by sarco/endoplasmic reticulum calcium ATPase (SERCA) pump. Therefore, RyR gating is critical to normal muscle function. In a resting cell (e.g., myocyte in diastole, relaxed muscle) elevated $Ca^{2+}$ in the cytoplasm due to leak through the RyR (and also insufficient $Ca^{2+}$ transport by SERCA pumps) is a hallmark dysfunction directly underlying severe diseases of the striated muscle, including skeletal (e.g., Duchenne muscular dystrophy (MD), limb girdle MD, geriatric muscle dysfunctions) and cardiac (e.g., ischemic heart failure (HF), catecholaminergic ventricular tachycardia (CPVT)). Moreover, evidence increasingly points to RyR dysregulation as a therapeutic target for widely spread non-muscle diseases e.g., type 2 diabetes and Alzheimer's disease (AD). Elevated intracellular $Ca^{2+}$ is part of a vicious cycle generating these severe and widespread pathologies in muscle, as well as other types of tissue. This vicious cycle may be interrupted by actions on the main $Ca^{2+}$ cycling players, the RyR channel and the SERCA pumps, to restore normal intracellular calcium concentration.

RyR Protein

The RyR protein is a homotetrameric complex (565 kDa/protomer) with most of its mass in a cytosolic headpiece that serves as scaffold for a multitude of smaller soluble partners that regulate the RyR $Ca^{2+}$ channel function (Bers D M, *J Mol Cell Cardiol*. 2004; 37:417-429). Three RyR isoforms have been identified in mammals. RyR1 is expressed in skeletal muscle, which provides an abundant source for in vitro studies. RyR2 is expressed mainly in the heart, while RyR3 is more ubiquitous. The three dimensional structures of the three RyR isoforms are highly similar, and structural studies of RyR1 and RyR2 show highly similar accessory protein topologies within RyR complexes (Cornea et al., *Proc Natl Acad Sci USA*. 2009; 106:6128-6133; Cornea et al., *J Biol Chem*. 2010; 285:19219-19226; and Guo et al., *Biophys J*. 2011; 101:2170-2177).

The smaller soluble partners that regulate the RyR $Ca^{2+}$ channel function include, but are not limited to, FK506 binding protein (FKBP12 and 12.6, ~12 kDa), which promotes the closed RyR state, and calmodulin (CaM, ~16 kDa), which integrates intracellular $[Ca^{2+}]$ into target-specific functional signals.

Figure 1:
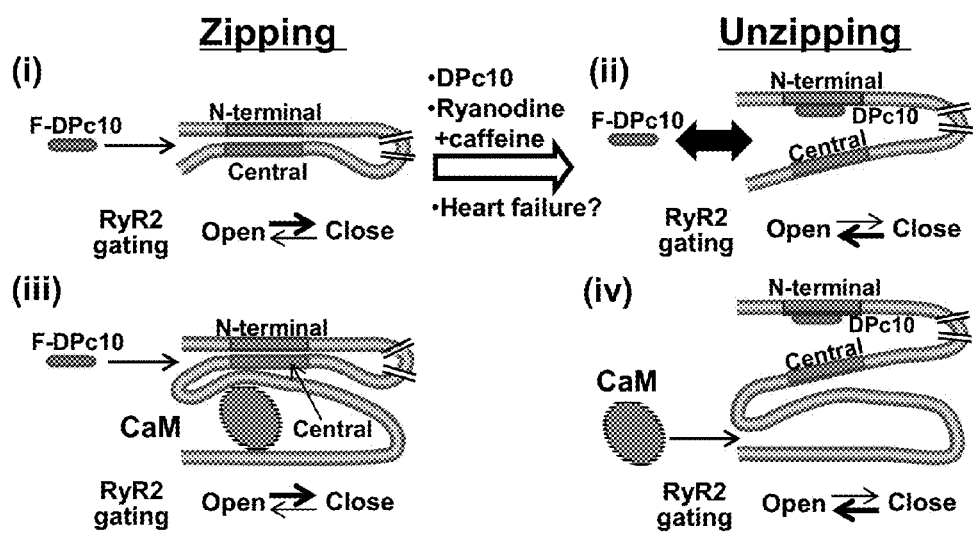
FIG. 1. Proposed model of the interaction between N-terminal and central domains. Kinetic results (Example 1) suggest that fluorescent DPc10 (F-DPc10) access to its binding site is controlled by interdomain interaction within RyR2. (i) The F-DPc10 access is sterically hindered in resting normal RyR2 ("zipped" state). (ii) Pre-treatment of RyR2 with physiological, pharmacological, or disease-mimetic agents that promote unzipping increase the F-DPc10 association rate and reduce CaM binding to RyR2. (iii) CaM inhibits the F-DPc10 binding to RyR2. (iv) DPc10 binding to RyR2 inhibits CaM binding to RyR2.

There is general agreement that sarcoplasmic reticulum calcium leak is increased in numerous pathological conditions, and several mechanisms are under consideration. Relevant for the methods described herein, for pathologically active (leaky) RyR channels (1) calmodulin binding is decreased (Ai et al., Circ Res. 2005; 97:1314-1322; Guo et al., Circ Res. 2006; 99:398-406; and Aracena et al., Antioxid Redox Signal. 2005; 7:870-881) and (2) structural interactions between N-terminal and central RyR domains are disrupted (a phenomenon often referred to as unzipping) (Kobayashi et al., *J Biol Chem*. 2005; 280:6580-6587; Kimura et al., *Cell Calcium*. 2009; 45:264-274; *Circ J*. 2010; 74:2579-2584; Oda et al., *Circulation*. 2005; 111:3400-3410; and Uchinoumi et al., *Circ Res*. 2010; 106:1413-1424). As described in Example 1, using FRET the inventors have found that access of a fluorescently-labeled unzipping domain peptide (F-DPc10, where "F" refers to the fluorescent label) to its RyR2 binding site is sterically hindered in the resting normal RyR2 (zipped state, (FIG. 1(i)), but physiological and pharmacological RyR activators increase F-DPc10 association rate (FIG. 1(ii)). Calmodulin, which quiets RyR2 opening (and therefore decreases $Ca^{2+}$ movement through the channel), also strongly inhibits F-DPc10 binding to RyR2 (FIG. 1(iii)). Reciprocally, F-DPc10 inhibits calmodulin binding to RyR2 (FIG. 1(iv)). Furthermore, it has been shown that DPc10 and calmodulin binding sites interact via a negative allosteric mechanism (Oda et al., Circ Res. 2013; 112:487-497). Taken together, these strongly support the notion that FRET detection of RyR binding of CaM and unzipping peptides (like DPc10) provide measurable indices of the pathological RyR leakiness. The methods described herein detect effects of compounds on RyR CaM binding and/or unzipping domain peptide (DP) access. Such compounds may be useful as therapeutic agents and/or as lead compounds in the development of therapeutic agents.

Without being bound by theory, in one embodiment, modulation of RyR by a test compound may have an effect on the conformation of an RyR molecule. The altered conformation may be a change in the secondary structure of the RyR, the tertiary structure of the RyR, or a combination thereof. In one embodiment, modulation of RyR by a test compound may alter the movement of calcium through the RyR channel. In one embodiment, modulation of RyR by a test compound may alter the binding of a domain peptide, a modulatory protein, a ryanodine variant, or a combination thereof, to an RyR molecule.

In one embodiment, the RyR protein used in the methods described herein is wild-type, and in some embodiments the RyR molecule includes one or more mutations that are present in RyR molecules associated with RyR dysfunction. In certain embodiments, an RyR protein is RyR1, RyR2, RyR3, or a combination thereof. The amino acid sequences of examples of each of these isoforms in various animals (including human, porcine, rat, and mouse), and the amino acid mutations associated with RyR dysfunction, are known to the person skilled in the art and are readily available.

In one embodiment, the RyR molecule used in the methods is a fusion protein, where the fusion is with a chromophore, such as a fluorescent protein. The fusion can be in any location within the amino acid sequence of an RyR monomer, provided it does not abolish the activity of an RyR channel, and provided the location of the fusion permits FRET between the chromophore and a second chromophore. Most known RyR constructs with fluorescent protein tags have altered function in some way. RyR fusion proteins useful herein may have altered function, but preserve essential channel characteristics, such as maintaining the RyR response to caffeine. The first chromophore may be a donor or an acceptor, and in one embodiment is a donor. In one embodiment, the second chromophore is also present in an RyR monomer as a fusion.

In one embodiment, an RyR protein includes a chromophore, and the chromophore (donor, acceptor, or both) is inserted into the RyR amino acid sequence to result in a fusion protein. Various RyR2 constructs with green fluorescent protein (GFP)-like inserts have been described (e.g., Liu et al., J Cell Sci. 2010; 123:1775-1784; Wang et al., J Biol Chem. 2011; 286:12202-12212; Huang et al., J Cell Sci. 2013; 126:4527-4535). Similar constructs that are near the 3 dimensional position of the FKBP binding site, or CaM binding site, or DPc10 binding site may be used herein. The optical properties of the GFP-like inserts can be optimized for brightness and separation from cell autofluorescence. In one embodiment, a GFP-like tag at position 1 (as described for RyR1 by Raina et al., PLoS One. 2012; 7:e38594), is used as FRET donor for acceptor-labeled fluorescent ryanodine variants. In one embodiment, a non-protein chromophore can be attached to the RyR.

An RyR protein used in the methods described herein can be produced using recombinant techniques, chemical or enzymatic synthesis, or be naturally occurring. An RyR protein may be isolated, or may be present in a cell.

FKBP

In one embodiment, the methods include the use of FKBP. In some embodiments, FKBP is FKBP12 and/or FKBP12.6. The FKBP12 and FKBP12.6 proteins are normally expressed in cardiac myocytes and can form tight complexes with RyR at a stoichiometry of 4 FKBPs per tetrameric RyR channel (Bers, J Mol Cell Cardiol. 2004; 37:417-429.). These FKBP isoforms are considered important RyR2 subunits and have been reported to promote the closed channel state. In some embodiments, the use of an FKBP variant with lower RyR-binding affinity is desirable. Examples of such FKBP variant proteins are known and include, but are not limited to, D41C (Cornea et al., J Biol Chem. 2010; 285:19219-19226), and the isoform FKBP12, which binds to RyR2 with ~100-fold lower affinity than FKBP12.6 (and only ~4-fold lower binding affinity for RyR1). In other cases, single point mutations, within regions of FKBPs that interface with RyRs, can significantly reduce FKBP-RyR binding affinity. In one embodiment, an FKBP variant has a 5 to 100-fold decrease in affinity, which would provide appropriate sensitivity. The amino acid sequences of examples of each of these isoforms, and the amino acid sequences of FKBP variants with decreased RyR-affinity, are known to the person skilled in the art and are readily available.

In one embodiment, an FKBP or a variant thereof includes a chromophore. The chromophore may be a donor or an acceptor. In one embodiment, the chromophore is a donor. When an FKBP includes a chromophore, it provides an RyR-specific fluorescent signal that maintains association with the RyR over the time-course of a typical FRET experiment. A molecule that includes a chromophore is referred to herein as being labeled with that chromophore. The chromophore and an FKBP protein or variant thereof may be attached by, for instance, an ionic bond, a hydrogen bond, a Van der Waals force, a hydrophobic interaction, a covalent bond, or a combination thereof. In one embodiment, the attachment includes a covalent bond. The chromophore may be attached to any location of an FKBP or variant thereof, provided the attached chromophore does not prevent the FKBP protein or variant thereof from binding to an RyR. In one embodiment an F-FKBP variant having unaltered RyR binding affinity and having reduced potency to inhibit RyR, namely ALEXA FLUOR™488-labeled N32C/C22A/C76I-hFKBP12.6, (Cornea et al., J Biol Chem. 2010;285:19219-19226) may be used. Suitable locations for attachment of a chromophore to an FKBP protein or variant thereof are known.

An FKBP protein used in the methods described herein can be produced using recombinant techniques, chemical or enzymatic synthesis, or be naturally occurring. An FKBP protein may be isolated, or may be present in a cell.

Modulatory Proteins

In one embodiment, the methods include the use of a protein that modulates the activity of an RyR protein, but is not an FKBP. In one embodiment, the modulatory protein is a calmodulin protein. Calmodulin (CaM) is an RyR modulator which integrates intracellular calcium concentration into target-specific functional signals. Other examples of modulatory proteins include, but are not limited to, soluble globular proteins like S100A1 and sorcin, membrane proteins like triadin and junctin, or venom peptides like imperatoxins A. The amino acid sequences of examples of calmodulin, S100A1, and sorcin are known to the person skilled in the art and are readily available. Mutants of these proteins that induce the pathological leaky state of RyR might be particularly useful, for example, Ca-insensitive CaMs (Cornea et al., *Proc Natl Acad Sci USA*. 2009; 106:6128-6133), or a CaM carrying the N54I or N98S mutations (Hwang et al., *Circ Res*. 2014; 114:1114-1124) linked to cathecolaminergic polymorphic ventricular tachycardia.

In one embodiment, a modulatory protein includes a chromophore. The chromophore may be a donor or an acceptor. In one embodiment, the chromophore is an acceptor. The interaction between a modulatory protein and a chromophore may be, for instance, an ionic bond, a hydrogen bond, a Van der Waals force, a hydrophobic interaction, a covalent bond, or a combination thereof. In one embodiment, the interaction includes a covalent bond. The chromophore may be attached to any location of a modulatory protein, provided the attached chromophore does not prevent the modulatory protein from binding to an RyR protein.

A modulatory protein used in the methods described herein can be produced using recombinant techniques, chemical or enzymatic synthesis, or be naturally occurring. A modulatory protein may be isolated, or may be present in a cell.

Domain Peptides

In one embodiment, the methods include the use of a domain peptide. An RyR molecule includes an N-terminal region and a central region that interact to stabilize and close the channel and prevent the movement of calcium through the channel. A domain peptide, also referred to as DP, specifically associates with the N-terminal region or the central region of an RyR molecule to destabilize the interaction between the two regions (a process referred to as "unzipping") and increase movement of calcium through the channel.

In one embodiment, a domain peptide is a protein that has a sequence identical to a series of 8 to 50 consecutive amino acids in an RyR polypeptide, such as residues 2460-2495 of RyR2 (Tateishi et al., *Cardiovasc Res*. 2009; 81:536-545) and the equivalent region of RyR1 (e.g., residues 2442-2477, Yamamoto & Ikemoto, *Biochemistry* 2002; 41:1492-1501). In one embodiment, a domain peptide has a sequence that is identical to a wild-type RyR. The amino acid sequences of examples of domain peptides are known to the person skilled in the art and are readily available. The skilled person can easily design other domain peptides that are a subset of known domain peptides and determine if they specifically associate with the N-terminal region or the central region of an RyR molecule to destabilize the interaction between the two regions. An example of a domain peptide is DcP10, which corresponds to RyR2 residues 2460-2495 (Yamamoto and Ikemoto, *Biochem Biophys Res Commun*. 2002; 291: 1102-1108). Another example of a domain peptide is DP163-195, which corresponds to RyR2 residues 163-195 (Tateishi et al., *Cardiovasc Res*. 2009; 81:536-545). In one embodiment, a domain peptide has a sequence that includes a mutation that is present in RyR molecules associated with RyR dysfunction, such as heart failure and lethal arrhythmias (e.g., catecholaminergic polymorphic ventricular tachycardia [CPVT]) (Tateishi et al., *Cardiovasc Res*. 2009; 81:536-545).

In one embodiment, a domain peptide includes a chromophore. The chromophore may be a donor or an acceptor. In one embodiment, the chromophore is an acceptor. The interaction between a domain peptide and a chromophore may be an ionic bond, a hydrogen bond, a Van der Waals force, a covalent bond, or a combination thereof. In one embodiment, the interaction includes a covalent bond. In one embodiment, the chromophore is present at the N-terminus. The chromophore may be attached to any location of a domain peptide, provided the attached chromophore does not prevent the domain peptide from binding to an RyR protein and inhibiting zipping.

A domain peptide used in the methods described herein can be produced using recombinant techniques, chemical or enzymatic synthesis, or be naturally occurring. A domain peptide may be isolated, or may be present in a cell.

Ryanodine

In one embodiment, the methods include the use of a ryanodine molecule. In one embodiment, ryanodine is labeled with a chromophore. The chromophore may be a donor or an acceptor. In one embodiment, the chromophore is an acceptor. Methods for attaching a chromophore to a ryanodine molecule are known to the skilled person and are routine.

Chromophores

Any appropriately selected two chromophores can be used as a donor-acceptor pairs in the methods described herein, provided that the energy emitted by a donor (the emission spectrum) overlaps with the energy absorbed by an acceptor (the excitation spectrum), e.g., an energy transfer process (FRET) occurs between two chromophores. A donor and an acceptor that meet this overlap are referred to as a donor-acceptor pair. In one embodiment, donor-acceptor pairs are chosen such that interference from cell autofluorescence or test-compound fluorescence is minimized. Accordingly, in some embodiments donors that can be excited at longer wavelengths are superior to those excitable at shorter wavelengths (e.g., ALEXA FLUOR™ 488 is superior to IAEDANS). Also, in some embodiments probes with longer fluorescence lifetime (FLT) (more than 3 nanoseconds (ns)) will be superior to probes with shorter FLT.

Chromophores suitable for the methods described herein are known to the skilled person and are routinely used. Methods for attaching a chromophore to a selected protein are known and routine. In one embodiment, examples include those suitable for analysis by conventional flow cytometry. Donor-acceptor pairs which can be used for detection by most conventional flow cytometers are discussed in, for example, Szollosi et al., *Communications in Clinical Cytometry*, 1998; 34:159-179). Chromophores as used herein may be fluorescent or non-fluorescent (e.g., luminescent components, or 4-((4-(dimethylamino)phenyl) azo)benzoic acid (DABCYL)). In certain embodiments, combinations of chromophores as used herein include those used in the classical tandem conjugates (see van Dongen et al., U.S. Pat. No. 7,413,862).

Examples of fluorescent components that are suitable for FRET assays disclosed herein include, but are not limited to, fluorescein, rhodamine, Green Fluorescent Protein (and variants thereof), 4-nitrobenzo-2-oxa-1 ,3-diazole (NBD); cascade blue, 4,4-difluoro-5,7-diphenyl-4-bora-3a,4a-diaza-s-indacene-3- propionic acid; 4,4-difluoro-5,p-methoxyphenyl-4-bora-3a,4a-diaza-s-indacene-3-propionic acid; 4,4-difluoro-5-styryl-4-bora-3a,4a-diaza-s-indacene-propionic acid; 6-carboxy-Xrhodamine, N,N,N',N'-tetramcthyl-6-carboxyrhodamine; iodoacetyl-directed probes such as 5-((((2-iodoacetyl)amino)ethyl)amino) naphthalene-1-sulfonic acid (1AEDANS, used interchangeably with AEDANS); 5-carboxyfluorescein; 6-carboxyfluorescein; 6-(fluorescein-5- carboxamide)hexanoic acid; fluorescein isothiocyanate (FITC); tetramethylrhodamine isothiocyanate (TRJTC); TEXAS RED™ (TR); eosin; a phycobiliprotein; cyanine dye; coumarin; R-phycoerythrin; allophycoerythrin (APC); a R-phycoerythrin (R-PE) conjugate; an ALEXA FLUOR dye; a HILYTE FLUOR™ dye; a quantum dot dye; maleimide-directed probes such as 4-dimethylaminoazobenzne-4'-maleimide (DABmal) and fluorescein-5-maleimide (Fmal); or a combination thereof (e.g., tandem conjugates) (see Thomas et al., WO 2010/085514).

In one embodiment, a chromophore used herein is a nucleotide analog such as an ATP-, ADP- or AMP-analog (see, e.g. Bagshaw, *J of Cell Science* 2001; 114:459-460). In certain embodiments, a nucleotide analog is fluorescent. Examples of fluorescent nucleotide analogs include, but are not limited to, 2'-(or -3')-0-(trinitrophenyl)adenosine 5'-triphosphate (TNP-A TP), 2'-(or -3')-0-(trinitrophenyl) adenosine 5'-diphosphate (TNP-ADP), e-A TP, e-aza-A TP, FTP, 2AP-TP, ant-ATP. Mant-ATP, DEDAA TP, FEDA-ATP, RED A-A TP and Cys3-EDA-ATP.

In one embodiment, examples of luminescent chromophores that are suitable for the methods disclosed herein include, but are not limited to, the luminescent ions of europium and terbium introduced as lanthanide chelates (Thomas et al.,*Proc Nat/ Acad Sci USA*, 1978;75:5746-5750). In one embodiment, examples of donor-acceptor pairs include fluorescein and rhodamine, NBD and rhodamine, NBD and eosin, NBD and erythrosine, fluorescein and eosin, fluorescein and erythrosin, dansyl and rhodamine, acridine orange and rhodamine, lanthanide ion and fluorescein, IAEDANS and TNP-ADP, IAEDANS and FITC, IAEDANS and DABmal, IAEDANS and Fmal, IAEDANS and DABCYL, ALEXA FLUOR™ 488 and either ALEXA FLUOR™ 568 or a HILYTE FLUOR™ 647. In one embodiment, the donor and acceptor pair as used herein is ALEXA FLUOR™ 488 and either ALEXA FLUOR™ 568 or a HILYTE FLUOR™ 647.

Methods

In the methods described herein, the experimental observations indicate that FRET detection of RyR binding of modulatory proteins like calmodulin and domain peptides like DPc10 provide measurable indications of the functional state of an RyR molecule. In some embodiments, the methods described herein will detect the effects of compounds on binding of FKBP to RyR, binding of calmodulin to RyR, access of domain peptides to their RyR binding sites, and/or binding of ryanodine-like molecules to RyR.

In preferred embodiments, the methods use the lifetime of a chromophore instead of its intensity. Methods for measuring fluorescence lifetime (FLT) are known to the skilled person and are routine. In one embodiment, FLT is measured using a plate reader (FLT-PR). FLT-PRs useful in the methods described herein are readily available (e.g., the FLT-PR available at the Biophysical Spectroscopy Center, University of Minnesota, Minneapolis, Minn.). The measurement of FLT by using direct wave recording detection technology in a plate reader provides the precision to resolve small changes in FRET, and can scan the plate rapidly (around 2 minutes/384-well plate). Advantages of the FLT readout include its insensitivity to variability in the donor concentration and to sample inhomogeneity (e.g., whether cells or membranes settle at the bottom of the well or are uniformly dispersed throughout the volume of the sample). Further, in some embodiments noise is decreased 30-fold, which greatly decreases both false positives and negatives. The conventional wisdom has been that FLT detection at high precision was just too slow for high throughput screening.

Figure 2:
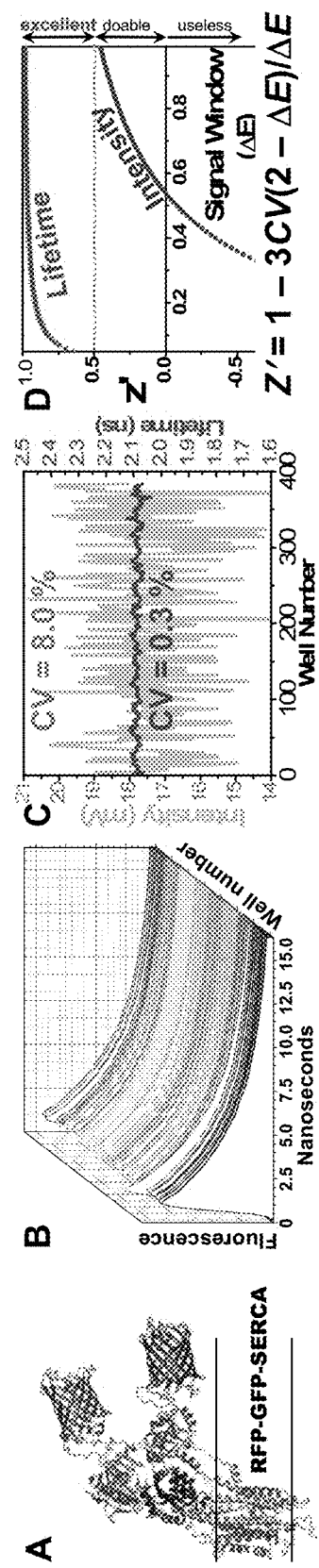
FIG. 2. The high-precision of FLT-PR enables reliable detection, in high-throughput mode, of very small changes in FRET. An enzyme labeled with donor and acceptor (panel A) is loaded in a 384-well microplate and fluorescence decays are rapidly measured (~2 minutes/plate) (panel B), with a coefficient of variance (CV) that is more than 20 times smaller (higher precision) in lifetime mode (panel C, trace at CV=0.3%) than in intensity mode (panel C, trace at CV+8.0%). This high-precision lifetime detection enables high-throughput screening assays of high quality (high Z'), whereas intensity measurements allow high-throughput screening assays of low quality of Z' value (D).

Typical lifetime plate-readers require greater than an hour to scan a 384-well plate at a signal/noise (S/N) of 100, while a lifetime plate-reader such as those described herein can scan a 384-well plate in approximately 2 minutes at S/N of 100. The result is a surprising and unexpected improvement of a factor of 100,000. In contrast, steady-state fluorescence readers measure intensity and provide much less information and less precision (FIG. 2 of HEK cells with a GFP-RFP-tagged SERCA (A)). Panel B of FIG. 2 shows FLT decays from all 384 wells (S/N>100) in the FLT-PR. Panel C of FIG. 2 shows differences in variance (CV=StDev/mean %) for fluorescence intensity vs. lifetime (CV=9 vs. 0.3%). The use of FLT-PR improved CV by 30×, resulting in an excellent quality high throughput screening index, z' (FIG. 2D) (Zhang et al., *J Biomol Screen*. 1999; 4:67-73). Z' is routinely used to determine whether an assay is amenable to screening in a high throughput format. A z'>0.5 indicates an excellent assay that can resolve a given signal change (x-axis). The precision provided by the FLT measurement (FIG. 2D, trace labeled "lifetime") would resolve tiny FRET changes ($\Delta E>0.05$), whereas intensity measurement (FIG. 2D, trace labeled "intensity") would be useless in high throughput screening at $\Delta E<0.5$, and mediocre at best for $\Delta E>0.5$. In one embodiment, the fluorescence lifetime in the presence of the test compound and the fluorescence lifetime in the absence of the test compound is a $\Delta E$ of greater than 2 times, greater than 2.5 times, or greater than 3 times the $\Delta E$ standard deviation of the control samples.

A measuring instrument useful in the methods disclosed herein is a spectrometer that is compatible with FRET assays and can perform direct waveform recording to detect the entire time course of a time-resolved fluorescence decay with high quality (signal/noise>100) within 1 ms or less, in a microplate format that allows for the analysis of several hundred samples per minute. An example of such an instrument is described by Cornea et al.(*J Biomol Screen*. 2013; 18:97-107). In certain embodiments, the FRET assays disclosed herein are measured at a single emission wavelength. In certain embodiments, the entire emission spectrum of the FRET is measured. For example, when ALEXA FLUOR™ 488 is the fluorescent donor, the emission wavelength is scanned from 500 nm to 650 nm.

RyR molecules are normally present in the membrane of the sarcoplasmic reticulum. RyR molecules useful in the methods described herein may be present in membranes purified from cells, or may be present in permeabilized cells. The cells that are used as a source of purified membranes and the cells that are permeabilized may be cells that normally have a large amount of sarcoplasmic reticulum. Such cells include myocytes, for example cardiomyocytes, such as ventricular myocytes. In some embodiments, myocytes from muscle that is dysfunctional, e.g., failing heart, pathologically stressed, or dystrophic, may be used as a source of RyR molecules. Cells may be vertebrate cells, such as human, murine (including mouse and rat), canine, or porcine, or from invertebrates, such as Army worm (e.g., Sf21 cells). Other cells include those engineered to express RyR molecules. The RyR used may be the isoform RyR1, RyR2, or RyR3

In some embodiments, the conditions used to assay RyR functional states may be modified to mimic the environment present in dystrophic or heart failure myocytes. For instance, the conditions may include supplementation with $H_2O_2$ or oxidized glutathione, an FKBP mutant with attenuated potency to inhibit RyR, a CaM mutant that activates RyR2 in nanomolar calcium or with attenuated potency to inhibit RyR2 in nanomolar calcium, e.g., the CaM with N54I or N98S mutations (Hwang et al., Circ Res. 2014; 114:1114-1124).

In one embodiment, the methods use permeabilized myocytes, such as ventricular myocytes. The myocytes may be adult myocytes. Prior to running the experiment, it was uncertain and unexpected that changes in FRET could be detected in cells when the subject protein was RyR, as it may be present in certain cells at higher levels, but it was unclear whether such levels were high enough to permit detection of FRET and FRET changes.

Figure 4:
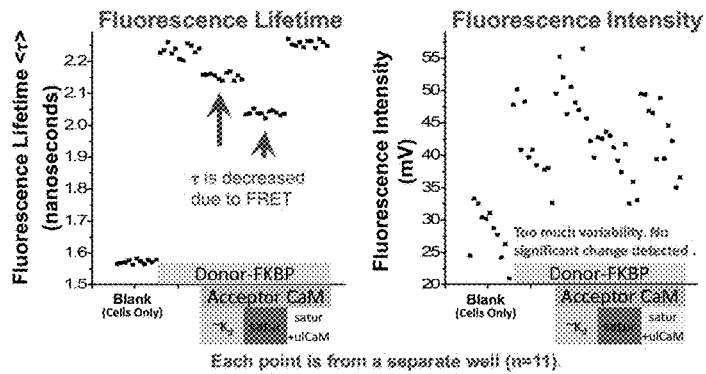
FIG. 4. FLT-detection enables high-precision FRET in cardiomyocytes.

To achieve 3-10 nM [D-FKBP] bound, it was estimated that 3,000-30,000 cells/well were needed. To test feasibility, permeabilized adult rat myocytes were used, treated with D-FKBP12.6 (unbound removed), with subsaturating and saturating acceptor-labeled CaM (FIG. 4). FLT and intensity readings were compared against a cell background. This initial pilot was promising and surprising in that differences in FRET were detected in cells at both sub-saturating and saturating concentrations of the modulatory protein calmodulin.

In FIG. 4 (left panel), it was found that FLT detection in the microplate reader enabled detection of small FRET differences in cardiomyocytes. In contrast, no significant difference were detected in intensity mode (steady-state fluorescence) as shown for the same samples, read in the same instrument, at the same time (FIG. 4, right panel). The table in FIG. 4 shows that precision (CV %) is ~20 times better in FLT mode, which is comparable with the results obtained with SERCA in HEK cells (FIG. 2). One way to further minimize interference from cell autofluorescence (blank in FIG. 4) is to use a donor that can be excited with a red laser, such as 532 nm, or that has a significantly longer FLT than the cell autofluorescence.

The sources for compounds that may modulate an RyR molecule include, but are not limited to, for instance, chemical compound libraries, fermentation media of *Streptomycetes*, other bacteria and fungi, and cell extracts of plants and other vegetations. Small molecule libraries are available, and include AMRI library, AnalytiCon, BioFocus DPI Library, Chem-X-Infinity, ChemBridge Library, ChemDiv Library, Enamine Library, The Greenpharma Natural Compound Library, Life Chemicals Library, LOPAC1280™, MicroSource Spectrum Collection, Pharmakon, The Prestwick Chemical Library®, SPECS, NIH Clinical Collection, Chiral Centers Diversity Library. In some embodiments, the number of compounds evaluated in an assay includes between 1 and 200,000 compounds, between 1 and 100,000 compounds, between 1 and 1,000 compounds, or between 1 and 100 test compounds. In one embodiment, during testing a compound may be present a micromolar concentrations, such as 10 micromolar.

Provided herein are methods for identifying a compound that modulates RyR. In one embodiment, the method includes providing a complex that includes an RyR molecule, an FKBP, and a domain peptide. The FKBP includes an attached chromophore that is a donor or an acceptor. The domain peptide also includes an attached chromophore that can be used with the chromophore attached to the FKBP for energy transfer. In one embodiment, the FKBP chromophore is a donor and the domain peptide chromophore is an acceptor. The method includes contacting the complex with a test compound to form a mixture, and measuring the fluorescence lifetime or intensity of the donor chromophore and/or the acceptor chromophore. A difference between the fluorescence lifetime or intensity in the presence of the test compound and the fluorescence lifetime or intensity in the absence of the test compound indicates that the test compound modulates RyR.

In one embodiment, the method includes providing a complex that includes an RyR molecule, an FKBP, and a modulator. The FKBP includes an attached chromophore that is a donor or an acceptor. The modulator also includes an attached chromophore that can be used with the chromophore attached to the FKBP for energy transfer. In one embodiment, the FKBP chromophore is a donor and the modulator chromophore is an acceptor. The method includes contacting the complex with a test compound to form a mixture, and measuring the fluorescence lifetime or intensity of the donor chromophore and/or the acceptor chromophore. A difference between the fluorescence lifetime or intensity in the presence of the test compound and the fluorescence lifetime or intensity in the absence of the test compound indicates that the test compound modulates RyR.

In one embodiment, the method includes providing a complex that includes an RyR molecule, an FKBP, a domain peptide, and a modulator. The domain peptide includes an attached chromophore that is a donor or an acceptor. The modulator also includes an attached chromophore that can be used with the chromophore attached to the domain peptide for energy transfer. In one embodiment, the domain chromophore is an acceptor and the modulator chromophore is a donor. The method includes contacting the complex with a test compound to form a mixture, and measuring the fluorescence lifetime or intensity of the donor chromophore and/or the acceptor chromophore. A difference between the fluorescence lifetime or intensity in the presence of the test compound and the fluorescence lifetime or intensity in the absence of the test compound indicates that the test compound modulates RyR.

In the methods described herein, the fluorescence lifetime or intensity of a chromophore may increase or decrease. In general, a test compound that decreases FRET between an FKBP and a domain peptide, such as DPc10, is considered an inhibitor of RyR1, RyR2, and RyR3. A test compound that increases FRET between an FKBP and a modulator such as calmodulin is considered an RyR2 inhibitor. For RyR1, the correlation between increased FRET from FKBP to calmodulin and RyR1 channel function may be different, because calmodulin has an activating effect on RyR1 at nanomolar $Ca^{2+}$, and an inhibitory effect at micromolar $Ca^{2+}$. Nevertheless, it is expected that a predictable correlation exists between test compound effects on FRET and RyR1 function. Such test compounds may be useful as therapeutic agents and/or as lead compounds in the development of therapeutic agents.

In some embodiments, the order of addition of the components may vary. For instance, in one embodiment, the complex includes an RyR molecule and the FKBP, and the test compound is added to the mixture before the domain peptide is added. In another embodiment, the complex includes an RyR molecule and the FKBP, and the test compound is added to the mixture before the modulator is added.

Figure 3:
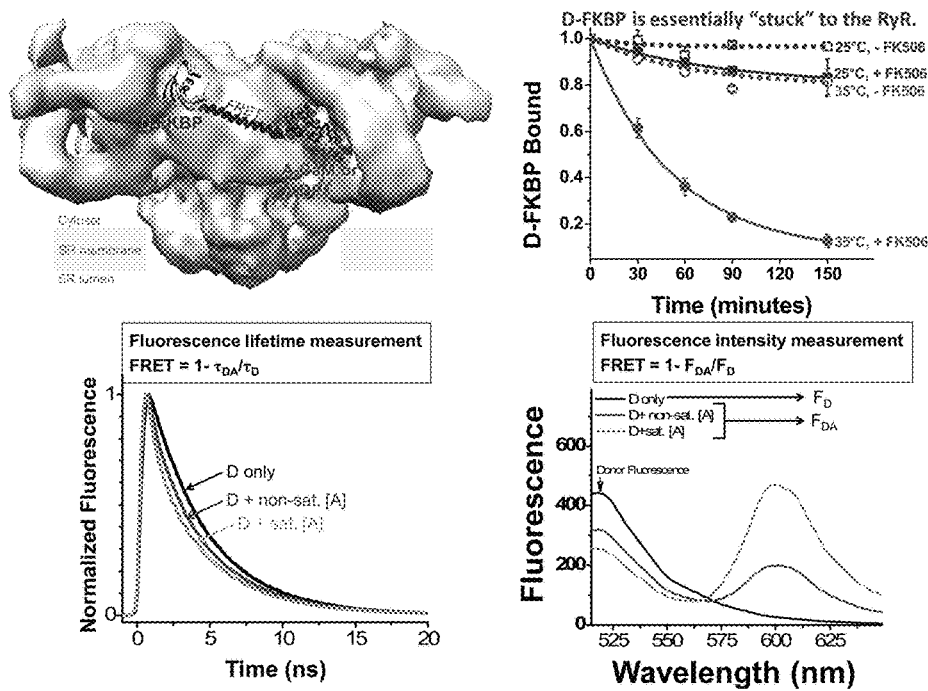
FIG. 3. FRET assays for RyRs. Using FKBP labeled with a FRET donor (D-FKBP) that is tightly bound to RyR it is possible to specifically detect binding of acceptor-labeled CaM (A-CaM), or domain peptides (A-DP) to RyR in the proximity of D-FKBP (upper left panel). D-FKBP dissociates from RyR very slowly, which means that most (>90%) D-FKBP remains bound to the RyR within the time frame of a FRET experiment (i.e., approximately 2.5 hrs) (upper right panel; "25° C., –FK506" trace). FRET can be detected as the decrease of fluorescence lifetime of donor ("D") in the presence of an acceptor ("A") bound in the donor's proximity (lower left panel). Fluorescence lifetime detection provides a significantly more precise measurement than the alternative method of FRET detection, the decrease in donor fluorescence intensity in the presence of an acceptor (lower right panel).
Figure 5:
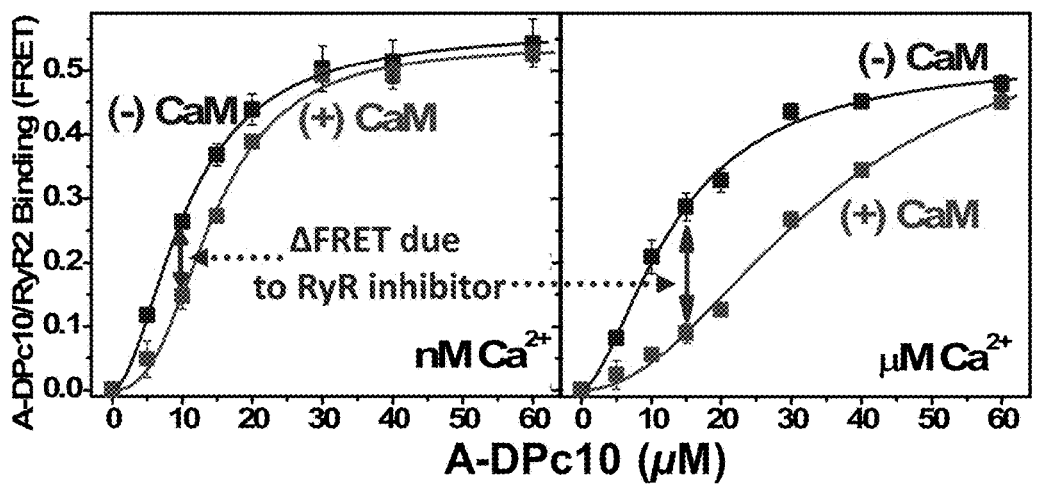
FIG. 5. Steady-state A-DPc10 binding by RyR2 is inhibited by CaM.

In certain embodiments, methods provided herein use FRET based methods to specifically detect RyR binding of modulatory proteins (e.g., CaM) and domain peptides which act as biosensors of channel unzipping (e.g., DPc10). FRET donor-probes are targeted to the cytoplasmic domain of RyR2 by using a FKBP or a variant thereof that is labeled with an appropriate chromophore, such as ALEXA FLUOR™ 488 or 568. As an RyR protein is typically the most prevalent FKBP target in the sarcoplasmic reticulum membranes and cells used in the methods, labeled FKBP provides an RyR specific fluorescent signal that is associated with its target over the time-course of a typical FRET experiment (FIG. 3, upper right). Upon addition of an acceptor labeled RyR ligand (e.g., calmodulin or a domain peptide), FRET is detected as a decrease in the fluorescence lifetime (FIG. 5 bottom left) or intensity of D-FKBP (FIG. 5 bottom right). This is analogous to placing a lamp post on the RyR to monitor binding events or conformational changes in its proximity.

In certain embodiments, the experimental design includes assays for RyR-specific FRET from D-FKBP (where D refers to donor probe) to both A-Donor Peptide (A-DP) and/or A-Calmodulin (A-CaM) (where A refers to acceptor probe) at subsaturating concentrations of the acceptor. In this embodiment, a "hit"-compound is a potential RyR inhibitor, and will both reduce DP binding and enhance CaM binding. Assays may use, for instance, isolated sarcoplasmic reticulum or permeabilized cells expressing RyR, such as the isoform RyR1, RyR2, or RyR3. In one embodiment, the amount of protein per well, the concentration of A-CaM, and the concentration of A-DP is used to give ~50% of maximal FRET. Precision (CV) may be assessed in full plates, with DMSO (the typical solvent in chemical libraries), with a test library and appropriate positive controls. In some embodiments, controls compared to conditions that mimic the environment in dystrophic or heart failure myocytes. Dystrophic or heart failure myocytes can be produced in a laboratory setting by exposure of cardiac myocytes to low concentrations of $H_2O_2$ or oxidized glutathione (GSSG)). As shown in Example 2, oxidative modification by $H_2O_2$ promotes RyR leakiness, reduces the affinity of calmodulin for RyR, has no effect on the affinity of FKBP for RyR, and causes domain unzipping. These lead to untimely and potentially arrhythmogenic RyR channel opening, however, domain peptides and modulators such as calmodulin are useful biosensors of this pathophysiological state of RyR. Further, $H_2O_2$ treatment to decrease CaM affinity and increase DP access can be used to widen the dynamic range (hence sensitivity) of the assays described herein.

In one embodiment, the method includes providing a complex that includes an RyR molecule, an FKBP protein, and a domain peptide. In one embodiment, the FKBP protein includes a donor probe, and the domain peptide includes an acceptor probe. The donor probe and the acceptor probe are matched in that they can be used for energy transfer from the donor to the acceptor that can be detected as a decrease in fluorescence lifetime or intensity. The complex is contacted with a test compound to form a mixture, and the fluorescence lifetime or intensity of the donor probe is measured. A difference between the fluorescence lifetime or intensity in the presence of the test compound and the fluorescence lifetime or intensity in the absence of the test compound indicates that the test compound modulates RyR. In one embodiment, the fluorescence lifetime or intensity of the donor probe is increased in the presence of the test compound, indicating that the test compound inhibits binding of the domain peptide to RyR.

Changes in FRET between D-FKBP and A-DPc10 were detectable after 2 hours incubation with 10-20 μM A-DPc10. In preliminary studies, the inventors have found that DPc10 binding to RyR2 is decreased by CaM (via allosteric interaction). Indeed, CaM inhibits A-DPc10 binding in the presence of nanoMolar (nM) $Ca^{2+}$ (relaxation), and in microMolar (μM) $Ca^{2+}$ (contraction) (FIG. 5). This is expected because CaM is an inhibitor of RyR2 throughout the physiological $Ca^{2+}$ concentration range, and therefore CaM should inhibit domain unzipping (thus DPc10 access). CaM is a moderate activator of RyR1 in nM $Ca^{2+}$ and an inhibitor in μM $Ca^{2+}$, so different CaM effect is expected on domain peptide binding to RyR1 samples. Differences between isoform responses are expected to possibly serve to isolate tissue specific effects. A test compound that decreases FRET is likely to be an RyR inhibitor.

In one embodiment, the method includes providing a complex that includes an RyR molecule and an FKBP protein, where the FKBP protein includes a donor probe. The complex is contacted with a test compound to form a mixture. A domain peptide is added to the mixture, where the domain peptide includes an acceptor probe. The donor probe and the acceptor probe are matched in that they can be used for energy transfer from the donor to the acceptor that can be detected as a decrease in fluorescence lifetime or intensity. The fluorescence lifetime or intensity of the donor probe is measured. A difference between the fluorescence lifetime or intensity in the presence of the test compound and the fluorescence lifetime or intensity in the absence of the test compound indicates that the test compound modulates RyR. In one embodiment, the modulation is alteration of access of the domain peptide for the RyR molecule. In one embodiment, the fluorescence lifetime or intensity of the donor probe is increased in the presence of the test compound, indicating that the test compound decreases access of the domain peptide for the RyR molecule.

Instead of equilibrium D-FKBP/A-DPc10 FRET (as described herein) the kinetics of A-DPc10 binding to RyR1 can be assessed. For instance, a an assay can be read at various times after A-DPc10 addition, such as 0 and 30 min after A-DPc10 addition). Data in myocytes shows slow F-DPc10 τwash-in (~80 min) in controls, and 50% faster τwash-in after $H_2O_2$ treatment, and this is restored by the positive-control compound (RyR inhibitor) dantrolene (FIG. 35B, upper panel). Compounds that slow A-DPc10 access to RyR are likely to be RyR inhibitors.

In one embodiment, the method includes providing a complex that includes an RyR molecule, an FKBP protein, and a modulatory protein. The FKBP protein includes a donor probe and the modulatory protein includes an acceptor probe. The donor probe and the acceptor probe are matched in that they can be used for energy transfer from the donor to the acceptor that can be detected as a decrease in fluorescence lifetime or intensity. The complex is contacted with a test compound to form a mixture, and the fluorescence lifetime or intensity of the donor probe is measured. A difference between the fluorescence lifetime or intensity in the presence of the test compound and the fluorescence lifetime or intensity in the absence of the test compound indicates that the test compound modulates RyR.

Figure 6:
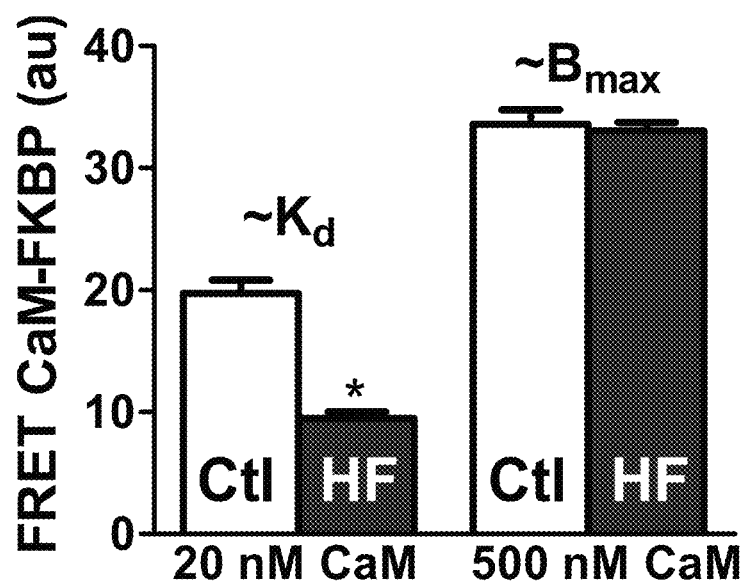
FIG. 6. CaM-RyR2 binding affinity is reduced in heart failure (reduced binding at sub-saturating CaM concentration but the same maximal binding at saturating CaM concentration).

Preliminary data show a 50% reduction of RyR2 A-CaM binding (at subsaturating concentrations of A-CaM) in myocyte from failing hearts (and similarly by 50 μM $H_2O_2$). However, CaM binding is unaltered at saturating A-CaM concentrations (FIG. 6). The optimal concentration of A-CaM may vary from sarcoplasmic reticulum to cell samples, but using a concentration of A-CaM that is at or near its $K_d$ will allow detection of enhanced CaM binding by FRET assays. Compounds that modulate CaM binding are expected to also affect RyR channel function, which can optionally be determined in secondary functional assays. Further preliminary data show compounds alter the binding of FKBP and/or CaM. A pilot screen of NIH Clinical Collection 1 used donor labeled FKBP and acceptor labeled CaM near their $K_d$. Several compounds known to perturb intracellular $Ca^{2+}$ cycling were identified as either increasing FRET (increasing binding of D-FKBP and/or A-CaM) or decreasing FRET (decreasing binding of D-FKBP and/or A-CaM) (FIG. 36). One of the compounds identified as reducing FRET was FK506, known to prevent binding of FKBP to RyR. The identification of FK506 as reducing FRET, and the identification of other FRET-altering compounds that alter intracellular $Ca^{2+}$ cycling, strongly suggest this approach is useful for identifying compounds that interact with RyR, perturb RyR structure, and modulate RyR channel function.

In some embodiments, a FKBP variant is used to detect changes in FKBP binding by using FRET between the FKBP variant and CaM. Wild-type FKBP12.6 binds too tightly, associates too fast, dissociates too slow to make it a practical probe in measuring changes in FKBP binding in some embodiments; however, FKBP variants having lowered RyR-binding affinity can be used. Such FKBP variants, e.g., D41C (Cornea et al., *J Biol Chem*. 2010; 285:19219-19226), have been reported. Screens in the presence of subsaturating D-FKBP concentration (i.e., near the $K_d$) and saturating A-CaM concentration can be conducted. In one embodiment, an FKBP has a $K_d$ of 5 to 1000 times higher than wild type FKBP. In one embodiment, a FKBP is at or within 1, 2, or 3 orders of magnitude of the $K_d$ of the FKBP for an RyR molecule. Compounds that significantly change FRET at equilibrium (i.e., alter the D-FKBP affinity) or in kinetic mode (i.e., alter association or dissociation constants) are expected to affect RyR channel function. Compounds that enhance D-FKBP/RyR affinity or association rate, or slow the dissociation rate do so presumably by promoting the closed RyR.

In one embodiment, the RyR molecule used in the methods is a fusion protein, where the fusion is with a fluorescent protein. Instead of the donor assays or the acceptor assays described above, an RyR-fluorescent fusion protein of optical properties suitable for a FRET partner is inserted at appropriate discrete locations within the RyR structure. The acceptor probe is attached to a modulatory protein or a domain peptide. Preliminary data using a Yellow Fluorescent Protein-RyR1 construct indicate that this is a perfectly feasible approach, as enabled by the FLT readout.

In yet another embodiment, the donor is an RyR-fluorescent fusion protein, where the fusion protein is inserted at the N-terminus of RyR. The acceptor is attached to a ryanodine molecule. Alterations in FRET in the presence and absence of a test compound indicate that the test compound modulates RyR. For example, a fusion with Yellow Fluorescent Protein at position 1 of an RyR would function as donor for an ALEXA FLUOR™ 568-ryanodine acceptor.

Kits

Also provided herein are kits for identifying a compound that modulates RyR. A kit may include, in any combination, a FKBP protein (optionally labeled with a donor or an acceptor probe), a modulatory protein such as calmodulin (optionally labeled with an acceptor probe), and/or a domain peptide (optionally labeled with an acceptor probe). A kit may optionally include a RyR molecule fusion protein, where the fusion is with a fluorescent protein. A kit may optionally include a ryanodine molecule that is attached to an acceptor probe.

In certain embodiments, a kit may further include buffers and reagents useful for the procedure, and instructions for carrying out the assay. In certain embodiments, a kit may further include other useful agents, such as positive and negative control reagents, and the like.

Methods and kits disclosed herein may be carried out in numerous formats known in the art. In certain embodiments, the methods provided herein are carried out using solid-phase assay formats. In certain embodiments, the methods provided herein are carried out in a well of a plate with a plurality of wells, such as a multi-well plate or a multi-domain multi-well plate. The use of multi-well assay plates allows for the parallel processing and analysis of multiple samples distributed in multiple wells of a plate. Multi-well assay plates (also known as microplates or microtiter plates) can take a variety of forms, sizes and shapes (for instance, round- or flat-bottom multi-well plates). Examples of multi-well plate formats that can be used in the methods provided herein include those found on 96-well plates (12×8 array of wells), 384-well plates (24×16 array of wells), 1536-well plate (48×3 2 array of well), 3456-well plates and 9600-well plates. Other formats that may be used in the methods provided herein include, but are not limited to, single or multi-well plates comprising a plurality of domains. In certain embodiments, the plates are opaque-wall, opaque-bottom plates. In certain embodiments, the plates are black-wall, black-bottom plates. In certain embodiments, the plates have black walls and clear bottoms in order to allow bottom excitation and reading of the fluorescence signals. In certain embodiments, the plates are chosen with minimal and uniform intrinsic fluorescence intensity within the range used in the method to avoid interference with the FRET signals.

The present invention is illustrated by the following examples. It is to be understood that the particular examples, materials, amounts, and procedures are to be interpreted broadly in accordance with the scope and spirit of the invention as set forth herein.

EXAMPLE 1

In Cardiomyocytes, Binding of Unzipping Peptide Activates Ryanodine Receptor 2 and Reciprocally Inhibits Calmodulin Binding DPc10 and related RyR2 peptides therefore may, serve as useful molecular probes to study the channel's structure-function relationship. However, the details of DPc10 binding to RyR2, including affinity and kinetics, are still unknown. In the present study, our goal was to characterize the binding of DPc10 to the RyR2 in the relatively intact environment of saponin-permeabilized rat ventricular myocytes. We used fluorescent DPc10 to measure the affinity and kinetics of DPc10 binding to RyR2 and its influence on CaM and FKBP12.6 binding and function. Furthermore, we used fluorescence resonance energy transfer (FRET) among fluorescent FKBP12.6, DPc10 and CaM to determine how DPc10 alters CaM and FKBP12.6 binding and to assess where the DPc10-binding site on RyR2 is in relation to CaM-binding and FKBP12.6-binding sites.

Materials and Methods

Figure 7:
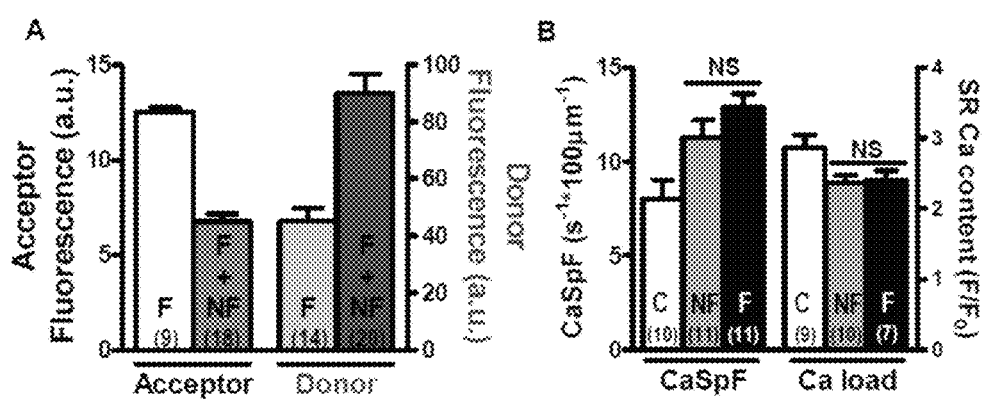
FIG. 7. A, Detection by FRET, as EAF or quenching of donor fluorescence, of the competitive inhibition of F-DPc10 binding to RyR2 by NF-DPc10 in permeabilized myocytes. Cells were incubated with FDPc10 (F, 1 µmol/L) or with equal concentrations (1 µmol/L) of F-DPc10 and NF-DPc10 (F+NF). B, Ca spark frequency and SR Ca content for control (C) myocytes, and after addition of NF-DPc10 (NF, 5 µmol/L) or FDPc10 (F, 5 µmol/L). Data are reported as mean±SE (n values on bars).

Rat ventricular myocytes were isolated and permeabilized as previously described (Li et al., *Circ Res*, 2002; 90:309-316). All procedures were performed according to the Guiding Principles in the Care and Use of the Animals and were approved by the Council of American Physiological Society. DPc10, FKBP12.6, and CaM were labeled at specific sites with small fluorescence probes, similar to our previous studies (Guo et al., *Circ Res*, 2010; 106:1743-1752; Cornea et al., *PNAS USA*, 2009; 106:6128-6133; Guo et al., *Biophys J*, 2011; 101:2170-2177). Competitive inhibition of fluorescent DPc10 (F-DPc10) binding to RyR2 by nonfluorescent DPc10 (nonfluorescent [NF]-DPc10) showed that both bind to RyR2 at the same site and same affinity (FIG. 7A). NF-DPc10 and F-DPc10 produce similar effects on $Ca^{2+}$ sparks and SR $Ca^{2+}$ content (FIG. 7B), confirming that F-DPc10 exhibits the same functional effect as NF-DPc10.

Rat Cardiac Myocyte Isolation

Single ventricular myocytes were isolated from rat hearts as described previously (Li et al., Circ Res. 2002; 90:309-316). Briefly, after anesthesia (isoflurane, 5%), hearts were excised and perfused (5 min, 37° C.) with the minimal essential medium (MEM, GIBCO Life Technologies) gassed with 95% O2/5% CO2 before inclusion of collagenase B (0.5 mg/ml, Boehringer Mannheim) and protease (0.02 mg/ml, Sigma). Triturates were incubated (10 min, 37° C.) in the same enzyme solution, washed and kept in 100 µM Ca2+MEM solution.

Domain Peptide

DPc10 peptides unlabeled and labeled with 5-carboxyfluorescein or HiLyte Fluor™647 were synthesized at AnaSpec (Fremont, Calif.). The DPc10 sequence is: 2460-GFCPDHKAAMVLFLDRVYGIEVQDFLLHLLEVGFLP-2495 (SEQ ID NO:1).

Fluorescent Labeling of Single-Cysteine Mutants of FKBP12.6 and CaM

A single-cysteine variant of the human FKBP12.6-isoform (T14C-C22A-C76I-FKBP12.6) was labeled using the thiol-specific maleimide derivatives of ALEXA FLUOR™ 488 and ALEXA FLUOR™ 568 (Invitrogen), as described previously (Cornea et al., PNAS USA, 2009; 106:6128-6133; Cornea et al., JBio Chem, 2010; 285:19219-19226). A single-cysteine CaM (T34CCaM) was labeled with ALEXA FLUOR™ 568 maleimide as described previously (Cornea et al., PNAS USA, 2009; 106:6128-6133; Cornea et al., JBio Chem, 2010; 285:19219-19226).

Laser scanning confocal microscopy

Confocal images was measured using a Biorad RADIANCE2100™ laser scanning confocal microscope equipped with an Argon ion laser, Green HeNe laser and with a Nikon Fluo x40 oil lens. FRET (fluorescence resonance energy transfer) experiments between CaM and DPc10, and FKBP12.6 and DPc10 were performed using an Olympus FV1000 confocal microscope. All experiments were done at room temperature.

Ca2+Sparks in Permeabilized Cells Using Confocal Microscopy

Myocytes were permeabilized with saponin (50µg/mL) for 60 seconds and placed in internal solution composed of EGTA 0.5 mmol/L; HEPES 10 mmol/L; Kaspartate 120 mmol/L; ATP 5 mmol/L; free MgCl2 1 mmol/L, reduced glutathione 10 mmol/L; and free [Ca2+] 50nmol/L (calculated using MaxChelator), creatine phosphokinase 5 U/mL, phosphocreatine 10 mmol/L, dextran 4% Fluo-4 0.025 mmol/L, pH 7.2. Ca2+sparks were recorded by a laser scanning confocal microscope (RADIANCE2000™ MP, Bio-Rad, UK) as previously described (Li et al., Circ Res, 2002; 90:309-316). Fluo-4 was excited at 488 nm and emission was recorded using 500/530 nm bandpass filter. To assess SR Ca2+content, caffeine (15 mmol/L) was rapidly perfused. Ca2+spark were analyzed as using SparkMaster (Picht et al., Am J Physiol Cell Physiol, 2007; 293:C1073-C1081).

FRET Measurements

For the FRET between CaM and DPc10, and FKBP12.6 and DPc10, we used Alexa Fluor 568 attached at the C-lobe of CaM (AF568-110-CaM) (Yano et al., Circulation, 2000; 102:2131-2136), ALEXA FLUOR™ 488 attached at the N-lobe of CaM (AF488-34-CaM), ALEXA FLUOR™ 568-, or ALEXA FLUOR™ 488-FKBP12.6 (Ai 'et al., Circ Res, 2005; 97:1314-1322; Wehrens et al., PNAS USA, 2006; 103:511-518) (AF488-FKBP12.6, AF568-FKBP12.6) and HiLyte Fluor™647-DPc10 (HF647-DPc10) as a donor-acceptor pair. AF488-, AF568- and HF647- were excited with separate laser channels of 488 nm, 543 nm and 635 nm, respectively. Emission fluorescence intensity data were obtained at 505-605 nm for AF488-FKBP12.6/AF488-34-CaM, 560-620 nm for AF568-FKBP12.6/AF568-110-CaM and 655-755 nm for HF647-DPc10. We used two experimental approaches, (1) comparing the donor fluorescence intensities before and after equilibration with acceptor (donor quenching) and (2) monitoring the increase in donor fluorescence after acceptor photobleaching (acceptor photobleaching), to detect and measure FRET signals in the permeabilized cardiomyocytes.

For the donor quenching method, FRET is indicated by a decrease in the donor fluorescence at wavelengths 505-605 nm (AF488-FKBP12.6) or 560-620 nm (AF568-FKBP12.6). The FRET efficiency (E) was calculated according to:

$$E = 1 - F_{DA}/F_D,$$

Where $F_D$ and $F_{DA}$ are the fluorescence intensities of the donor-only and donor-acceptor samples, respectively.

Complete acceptor (HF647) photobleaching was achieved by repeated scans of a defined area of the myocyte with the 635 nm laser at maximum power, for 60 sec. E was calculated according to:

$$E = [(I_{donor-post} - I_{donor-pre})/I_{donor-post}] \times 100\%,$$

where $I_{donor-post}$ and $I_{donor-pre}$ are donor fluorescence intensities before and after acceptor photobleach. Donor-acceptor distances, R, were calculated from the equation:

$$R = R_0(E^{-1} - 1)^{1/6},$$

where the Förster distance, $R_0$ is defined as the distance at which E=0.5. $R_0$ is calculated from $$R_0 = 9780(J\kappa^2 n^{-4}\phi_D)^{1/6},$$

where n is the refractive index of protein in aqueous solution (1.4), κ is the orientation factor (set to ⅔, corresponding to random orientation), $\phi_D$ is the fluorescence quantum yield of the donor (0.92 for AF488, and 0.69 for AF568[5]). J is the normalized spectral-overlap integral of donor emission $F_D(\lambda)$ and acceptor absorbance $\epsilon(\lambda)$ and is calculated from $$J = (\int F_D(\lambda)\epsilon(\lambda)\lambda^4 d\lambda)/\int F_D(\lambda)d\lambda,$$

by numerical integration using a Microcal Origin template. For the AF488-HF647 and AF568-AF647 donor-acceptor pairs we used $\epsilon_{H647}$ (652 nm)=250,000 (mol$^{-1}$ cm$^{-1}$) to calculate $R_0$ values of 54 A and 75 A, respectively.

Statistics

Data were expressed as mean±SEM, and significance was evaluated using student's t test or one-way ANOVA. A P-value below 0.05 was considered statistically significant.

Results

Localization and Binding Isotherms of F-DPc10 in Permeabilized Myocytes

FIG. 7A shows confocal images of saponin-permeabilized rat ventricular myocytes incubated with different concentrations of DPc10 labeled with 5-carboxyfluorescein at its N terminus (F-DPc10). Myocytes were exposed to 0.2, 0.5, and 5µmon F-DPc10, with intracellular [$Ca^{2+}$] ([$Ca^{2+}$]$_i$) set at 50 nmol/L. F-DPc10 fluorescence is highest at the Z-lines, where RyR2 is concentrated, forming a typical cross-striated pattern. The difference between fluorescence intensity at the Z-line (Fz) and M-line (FM) is taken to represent [F-DPc10]

specifically bound at the myocyte Z-line. We calibrated the bound [F-DPc10] in permeabilized myocytes using the linear relationship between F-DPc10 fluorescence and bath [F-DPc10] (FIG. 7B). In-cell F-DPc10-binding isotherms indicate an apparent dissociation constant ($K_d$) for F-DPc10 binding at the Z-line of 480±24 nmol/L; the maximal binding ($B_{max}$) (binding maximum), which reflects the concentration of F-DPc10-binding sites, was 1.59±0.03 μmon (FIG. 7C). This $B_{max}$ value for F-DPc10 is similar to our previous steady-state binding measurements of FKBP12.6 sites, which specifically bind to RyR2 (ryanodine receptor 2) in permeabilized myocytes with subnanomolar affinity (Guo et al., Circ Res, 2010; 106:1743-1752).Thus, we infer that RyR2 is the main target for F-DPc10 (see Discussion). To further test whether this Z-line-associated F-DPc10 represents RyR2-bound F-DPc10, we measured FRET between FKBP12.6 (known to specifically bind to RyR2 with subnanomolar affinity) (Guo et al., Circ Res, 2010; 106:1743-1752) and F-DPc10. FIG. 9A shows confocal images of FRET between FKBP12.6 labeled with ALEXA FLUOR™ 568 as a donor (AF568-FKBP12.6) and different concentrations of DPc10 labeled with HYLITE FLUOR™ 647 (HF647) as an acceptor (HF647-DPc10). Donor (AF568-FKBP12.6) fluorescence at the Z-line was quenched by HF647-DPc10, but the M-line signal was not (FIG. 9B). The apparent $K_d$ calculated based on enhanced acceptor fluorescence was 610±61 nmol/L, and the apparent $K_d$ calculated based on donor fluorescence quench was 450±43 nmol/L (FIG. 9C). The donor quench measurement is less complicated (eg, by donor bleed-through), and consequently likely to be more accurate, yielding a $K_d$ value that is remarkably similar to that obtained in our direct measurements of F-DPc10 at the Z-line (FIG. 8C).

Binding Kinetics of F-DPc10 in Permeabilized Cardiac Myocytes

Figure 8:
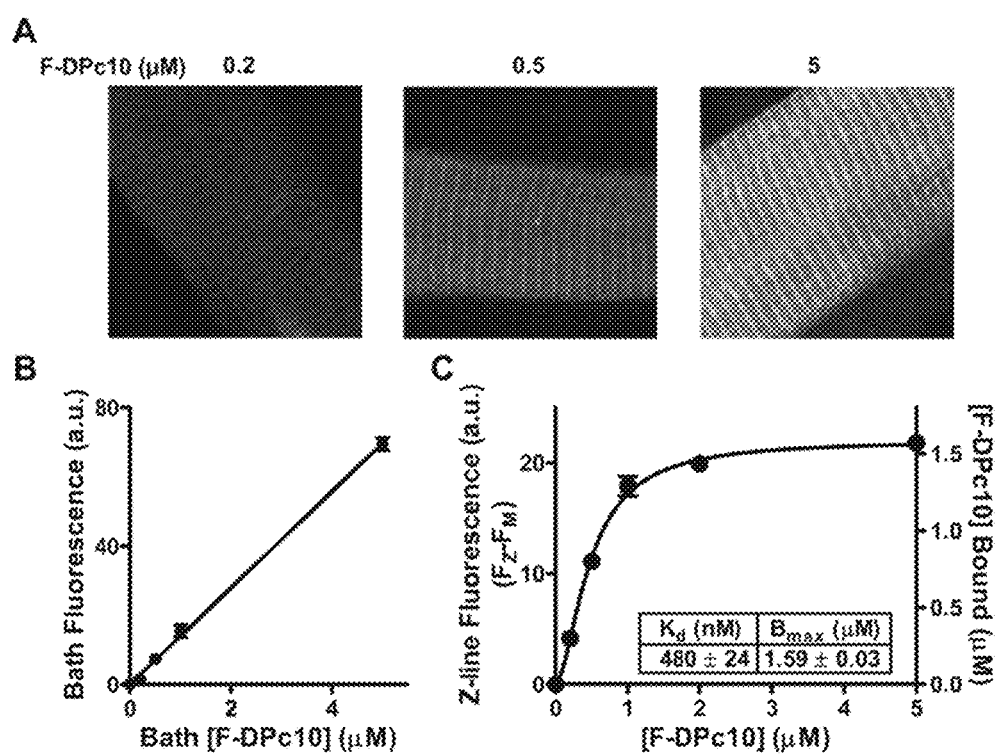
FIG. 8. Localization and steady-state binding of fluorescent DPc10 (F-DPc10) in permeabilized myocytes. A, Confocal images of saponin-permeabilized myocytes incubated in internal solution containing 0.2, 0.5, and 5 µmol/L F-DPc10. B, Dependence of bath F-DPc10 fluorescence on [F-DPc10]. C, Specific binding of F-DPc10 at the Z-lines ($F_Z$-$F_M$), calibrated based on the standard curve in (B), and fit to single-site binding isotherm. Data are reported as mean±standard error with n=10.
Figure 11:
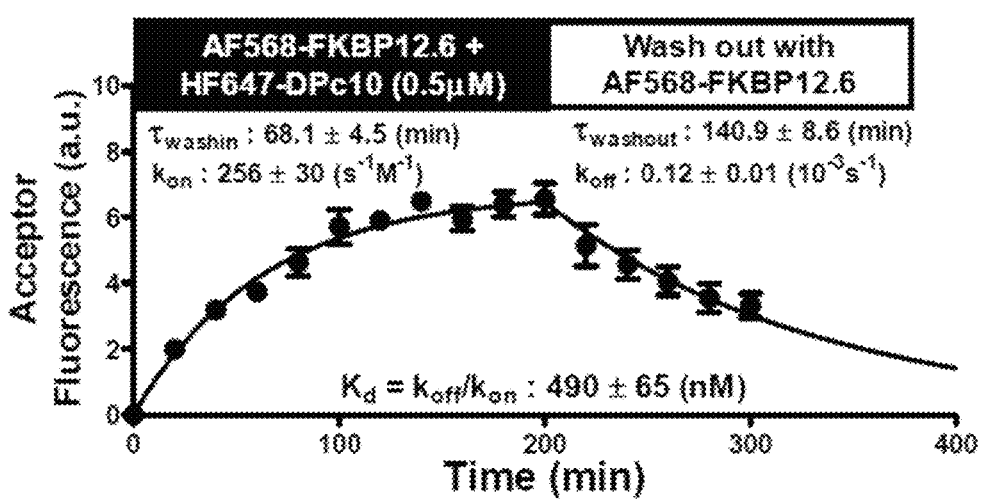
FIG. 11. Kinetics of HF-DPc10 binding, measured by FRET between FFKBP12.6 and HF-DPc10. Wash-in and wash-out time course of FRET after addition of HF-DPc10 (0.5 µmol/L), detected as EAF (A) or as donor quenching (B). Data are reported as mean±SE (n=4).
Figure 11:
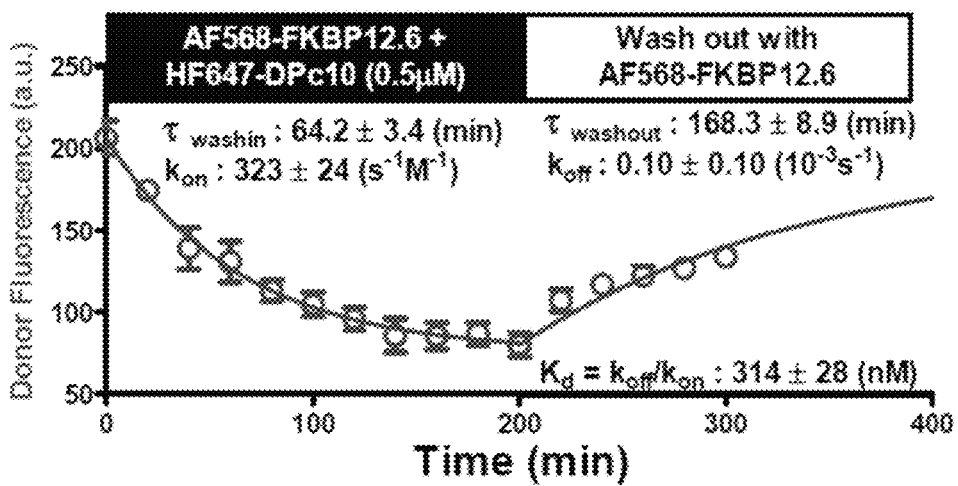

To characterize DPc10-binding kinetics at Z-lines, we performed F-DPc10 wash-in (500 nmol/L) and washout experiments in permeabilized myocytes (FIG. 10A). Association ($\tau_{wash-in}$=79.0±3.2 minutes) and dissociation ($\tau_{washout}$=149.8±4.4 minutes) were very slow compared with similar FKBP12.6 measurements (Guo et al., Circ Res, 2010; 106:1743-1752). From the wash-in/washout measurements, we calculated the association and dissociation rates constants, $k_{on}$ and $k_{off}$, respectively, according to the following equation:

$$k_{wash-in}=[F\text{-}DPc10]k_{on}+k_{off}$$

where $k_{washout} \approx k_{off}$ and $k=1/\tau$ (s$^{-1}$). Accordingly, $k_{on}$=202±20 (L mol$^{-1}$ s$^{-1}$) and $k_{off}$=0.11±0.01 (10$^{-3}$ s$^{-1}$). Based on these values and $K_d=k_{off}/k_{on}$, F-DPc10 binds at the Z-line with $K_d$=580±69 nmol/L, consistent with the steady-state $K_d$ measurements (FIG. 8). We repeated this kinetic analysis using FRET between FKBP12.6 and DPc10, thus assessing the RyR2-specific DPc10 binding (FIG. 11A AND 11B). Both methods of detecting FRET (enhanced acceptor fluorescence and donor quench) showed slow association and dissociation rates similar to those in FIG. 3 for direct detection of F-DPc10 binding at the Z-line. Based on these kinetic and affinity analyses, we infer that most of the Z-line-specific DPc10 binding is to RyR2. This is also consistent with $B_{max}$, which would imply ≈1 DPc10 per RyR2 monomer.

Figure 12:
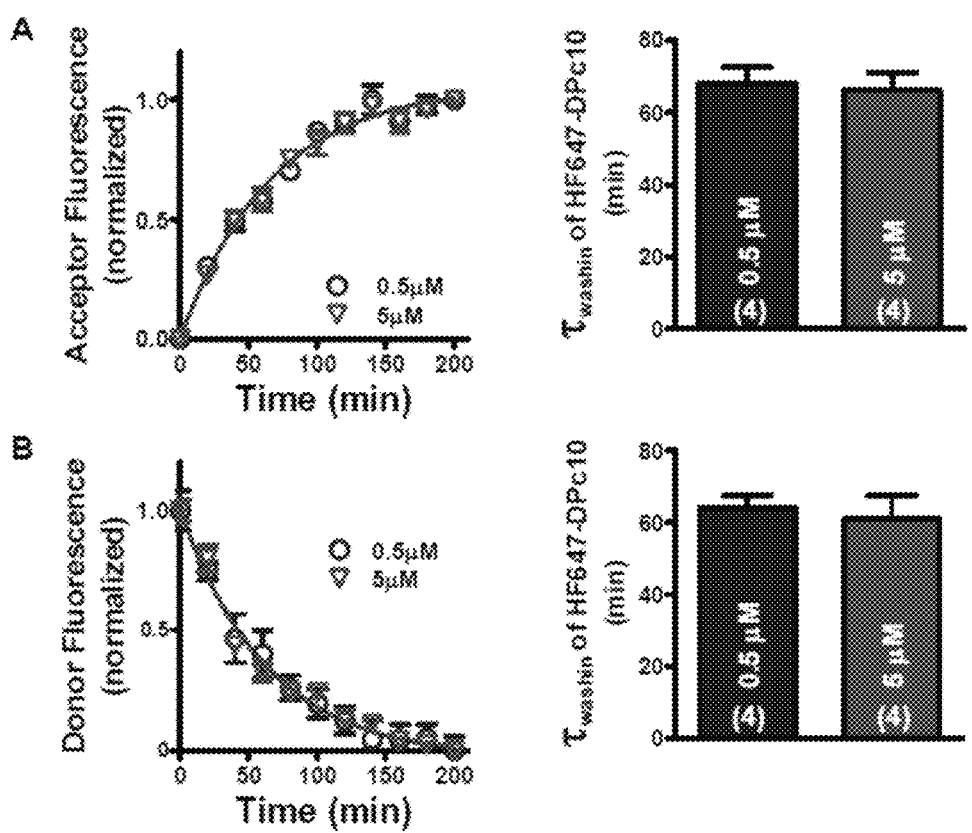
FIG. 12. Effect of DPc10 concentration on the wash-in rate, measured using FRET between FFKBP12.6 and HF-DPc10. FRET was detected as EAF (A) or as donor-fluorescence quenching (B), at 0.5 µM (circles) and 5 µM (triangles) HF-DPc10. Data are reported as mean±SE (n values on bars).

We were intrigued by the slow $k_{wash-in}$ and conducted measurements to further understand the basis of this slow association. We tested the hypothesis that at resting [Ca$^{2+}$]$_i$, DPc10 access to its RyR2 binding site is sterically hindered. If the N-terminal and central domains are tightly zipped to each other, then this interaction may occlude the DPc10-binding site on the RyR2, thus limiting the $k_{on}$ for DPc10. Alternatively, a limiting factor may be the rate at which DPc10 adopts a conformation that can bind to RyR2. To discern between these mechanisms, we determined the effect of [F-DPc10] on $\tau_{wash-in}$. If the small fraction of DPc10 in the right conformation limits binding rate, then $\tau_{wash-in}$ should be faster at higher [F-DPc10], according to Equation. FIG. 10B shows that this was not the case. Instead, a 10-fold increase in [F-DPc10] had no significant effect on the $\tau_{wash-in}$, although it did increase $B_{max}$ (FIG. 10B). The same was seen when using FKBP12.6-DPc10 FRET to assess $\tau_{wash-in}$ with 0.5 vs 5 μmol/L HF647-DPc10 (FIG. 12A AND 12B). These results indicate that F-DPc10 association at its RyR2 binding site exhibits restricted access by a factor residing on RyR2 (eg, binding site opening or transitions from zipped to unzipped state).

In our working model, under resting conditions, the RyR2 closed state may be stabilized by the interaction between the N-terminal and central domain in the zipped state. We hypothesized that conditions that promote RyR2 opening might enhance the rate of unzipping and accelerate $\tau_{wash-in}$ for F-DPc10. To test this, we first monitored F-DPc10 wash-in at elevated Ca$^{2+}$ (500 nmol/L). However, the 13% faster mean $\tau_{wash-in}$ was not significant (FIG. 13A). Although 500 nmol/L Ca$^{2+}$ can increase RyR2 opening, it does not prolong open time appreciably, and the latter might be important in the propensity for unzipping. Thus, we preincubated myocytes with ryanodine (100 μmol/L) plus caffeine (5 μmol/L), which are known to favor long RyR2 openings and were reported to cause RyR2 domain unzipping in HEK293 cells (Liu et al., J Cell Sci, 2010; 123: 1775-1784). Ryanodine+caffeine produced a 21% faster $\tau_{wash-in}$ (P=0.002; FIG. 13B). However, the most significant effect was seen after presaturating RyR2 with NF-DPc10 (and then NF-DPc10 washout with F-DPc10 present; FIG. 13A). This treatment significantly accelerated F-DPc10 association by a factor of ≈2 (FIG. 13A). None of these treatments significantly altered $B_{max}$ (FIG. 13A ABD 13B). Assuming that $k_{off}$ of NF-DPc10 is the same as for F-DPc10 and using Equation, the $k_{on}$ is increased by 3.2-fold by unzipping as a result of prebinding of NF-DPc10 to the RyR2. Our working hypothesis is that the RyR2 open state may increase the probability of an RyR2 shifting to the unzipped state and may allow faster F-DPc10 wash-in. It also seems that the RyR2 open state (favored by caffeine-ryanodine) differs from the unzipped state (bound with DPc10).

Figure 14:
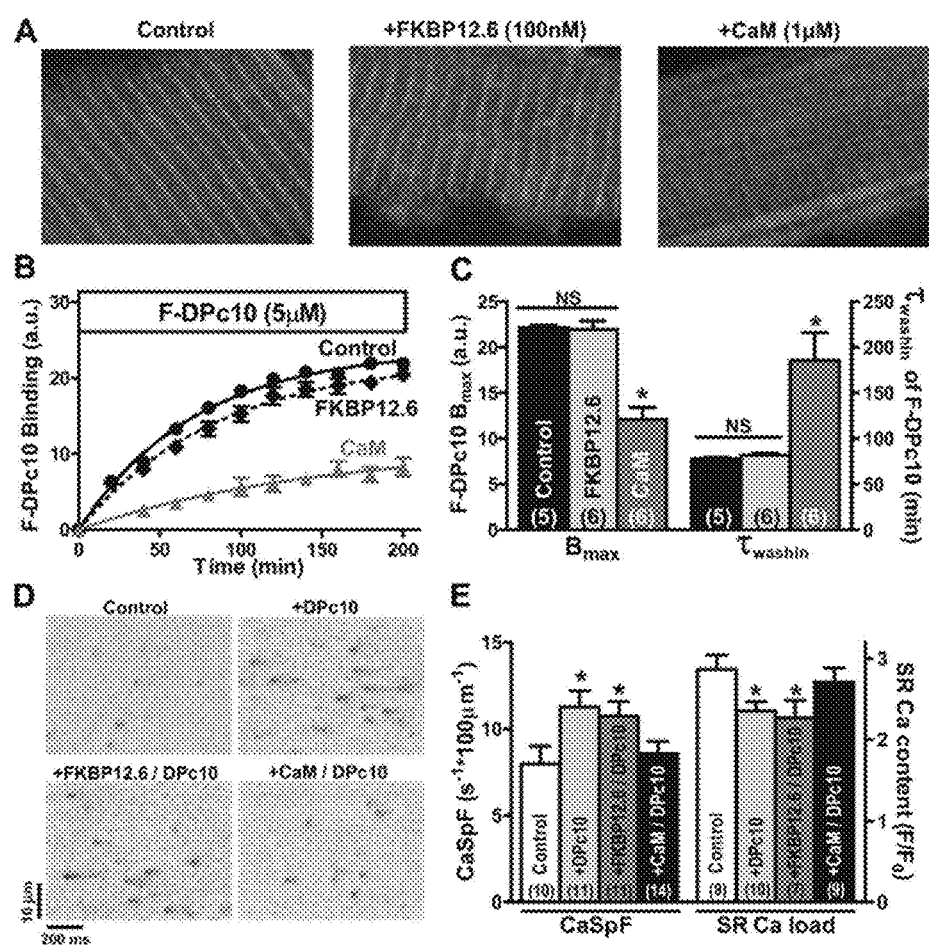
FIG. 14. Effects of FK506-binding protein 12.6 (FKBP12.6) and calmodulin (CaM) on fluorescent DPc10 (F-DPc10) binding at the Z-line and on local $Ca^{2+}$ release events in permeabilized cardiomyocytes. A, Representative confocal images illustrating the effect of FKBP12.6 (100 nmol/L) and CaM (1 µmol/L) on the F-DPc10 (5 µmol/L) binding at the Z-lines. B, Time course of F-DPc10 (5 µmol/L) wash-in (circles) and in the presence of FKBP12.6 (100 nmol/L, diamonds) or CaM (1 µmol/L, triangles). C, Summary of fitting parameters ($B_{max}$ and $\tau_{wash-in}$) for the data in (B). Data are reported as mean±standard error (SE). D, $Ca^{2+}$ sparks measured using Fluo-4 as $Ca^{2+}$ indicator. Representative line-scan images acquired after addition of DPc10 (5 µmol/L), DPc10 (5 µmol/L) plus FKBP12.6 (100 nmol/L), and DPc10 (5 µmol/L) plus CaM (1 µmol/L). $[Ca^{2+}]_i$=50 nmol/L, buffered by 0.5 µmol/L EGTA. E, Summary of $Ca^{2+}$ spark frequency and sarcoplasmic reticulum (SR) $Ca^{2+}$ content. SR $Ca^{2+}$ content was measured by addition of 15 µmol/L caffeine. Data are reported as mean±SE (n values on bars; a.u., arbitrary units).
Figure 15:
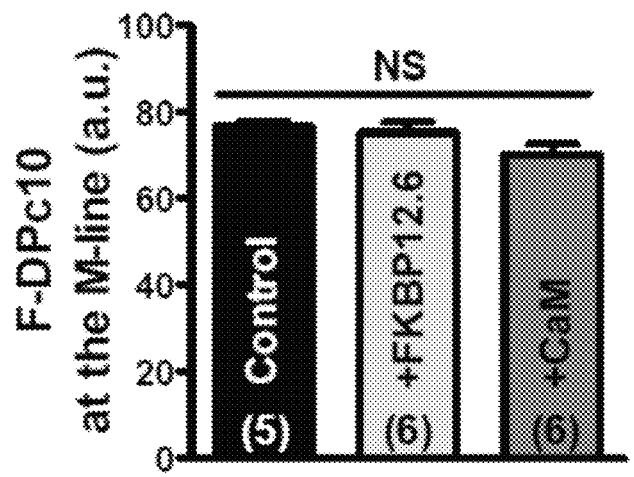
FIG. 15. Influence of FKBP12.6 or CaM on F-DPc10 fluorescence at the M-line. Addition of FKBP12.6 or CaM does not significantly change the M-line fluorescence intensity of F-DPc10. Data are reported as mean±SE (n values on bars).

Both FKBP12.6 and CaM bind to the RyR2 and can reduce channel opening, which might alter DPc10 binding. FIG. 14A shows representative confocal images of FKBP12.6 (100 nmol/L) and CaM (1 μmol/L) effects on F-DPc10 binding, as detected after a 200-minute incubation with F-DPc10. Although pre-equilibration with saturating CaM (1 μmol/L) greatly reduced F-DPc10 binding, pretreatment with FKBP12.6 (100 nmol/L) did not alter F-DPc10 binding in permeabilized myocytes. Neither CaM nor FKBP12.6 pretreatment altered M-line F-DPc10 fluorescence (FIG. 15). FIG. 14B shows the time course of F-DPc10 wash-in with or without pretreatment with FKBP12.6 or CaM. Saturation of RyR2 with FKBP12.6 (100 nmol/L) did not alter either F-DPc10 maximal binding ($B_{max}$) or $\tau_{wash-in}$. In contrast, saturation of RyR2 with CaM dramatically reduced $B_{max}$ for F-DPc10 and slowed DPc10 access to its binding site, as indicated by the large increase in $\tau_{wash-in}$ (FIG. 15C). We infer that CaM stabilizes the domain interaction between N-terminal and central domains in the zipped state and thereby may reduce DPc10 access to its binding site. To test for direct CaM-DPc10 interaction, we performed control FRET measurements between donor-labeled CaM and acceptor-labeled DPc10 in solution in the absence of RyR. The maximal FRET efficiency (<1%) ruled out direct CaM-DPc10 interaction.

Figure 16:
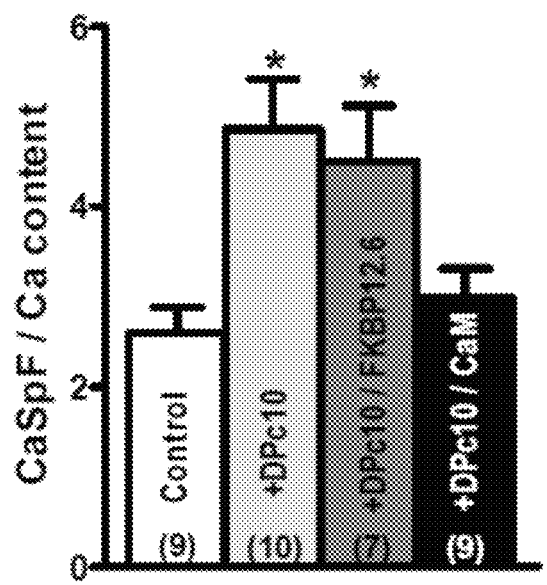
FIG. 16. Ca spark frequency normalized to the SR Ca content for myocytes after addition of DPc10 (5 µmol/L), DPc10 (5 µmol/L) plus FKBP12.6 (100 nmol/L), DPc10 (5 µmol/L) plus CaM (1 µmol/L). Data are reported as mean±SE (n values on bars).

Next, we asked whether RyR2 is activated by DPc10 and whether FKBP12.6 or CaM can prevent this. We assessed $Ca^{2+}$ sparks in permeabilized myocytes perfused with internal solution containing 50 nmol/L free $Ca^{2+}$ plus 1 µmol/L autocamtide-2-related inhibitory peptide (to inhibit CaMKII activity). Line-scan images were recorded after 3-hour incubations under control conditions and in the presence of 5 µmol/L DPc10, with or without 1 µmol/L CaM or 100 nmol/L FKBP12.6 (FIG. 14D). DPc10 robustly increased CaSpF vs control, an effect almost completely blocked by CaM (FIG. 14E). However, CaSpF activation by DPc10 was only slightly decreased by FKBP12.6 (FIG. 14E), and not decreased at all when normalized to SR (sarcoplasmic reticulum) $Ca^{2+}$ content (FIG. 16). In DPc10-treated permeabilized myocytes, $Ca^{2+}$ spark full width at half maximum and full duration at half maximum were significantly increased compared with control and decreased when pretreated with CaM (Table I).

TABLE I

Ca2+ spark characteristics in permeabilized cardiomyocytes.

|  | No. of Sparks | Peak (F/F$_0$) | FWHM (µm) | FDHM (ms) |
| --- | --- | --- | --- | --- |
| Control | 1761 | 0.499 ± 0.004 | 1.28 ± 0.01 | 55.7 ± 0.67 |
| +DPc10 | 1467 | 0.475 ± 0.004* | 1.34 ± 0.01* | 58.5 ± 1.00* |
| +FKBP12.6/DPc10 | 1921 | 0.439 ± 0.002* | 1.21 ± 0.01* | 60.5 ± 0.73* |
| +CaM/DPc10 | 2195 | 0.467 ± 0.003* | 1.23 ± 0.01* | 56.9 ± 0.74 |

Because CaSpF strongly depends on the SR $Ca^{2+}$ content, we also measured SR $Ca^{2+}$ content as the amplitude of caffeine-induced $Ca^{2+}$ release (FIG. 14E). In cells treated with DPc10 with or without FKBP12.6, the SR $Ca^{2+}$ was significantly lower than under control conditions. In contrast, treatment with CaM plus DPc10 resulted in no significant decrease in SR $Ca^{2+}$ content vs control. Thus, the increased CaSpF in the presence of FKBP12.6 plus DPc10 cannot be secondary to increased SR $Ca^{2+}$ content (which was in fact decreased). These results are consistent with a DPc10-induced increase in RyR2 channel activity resulting from defective interaction between N-terminal and central domains. This also agrees with the lack of FKBP12.6 effect on F-DPc10-binding kinetics (FIG. 14B) and the potent inhibition of DPc10 binding by CaM (which may promote the zipped state and inhibit DPc10 access).

Effect of DPc10 on FKBP12.6 and CaM Binding in Permeabilized Myocytes

Figure 17:
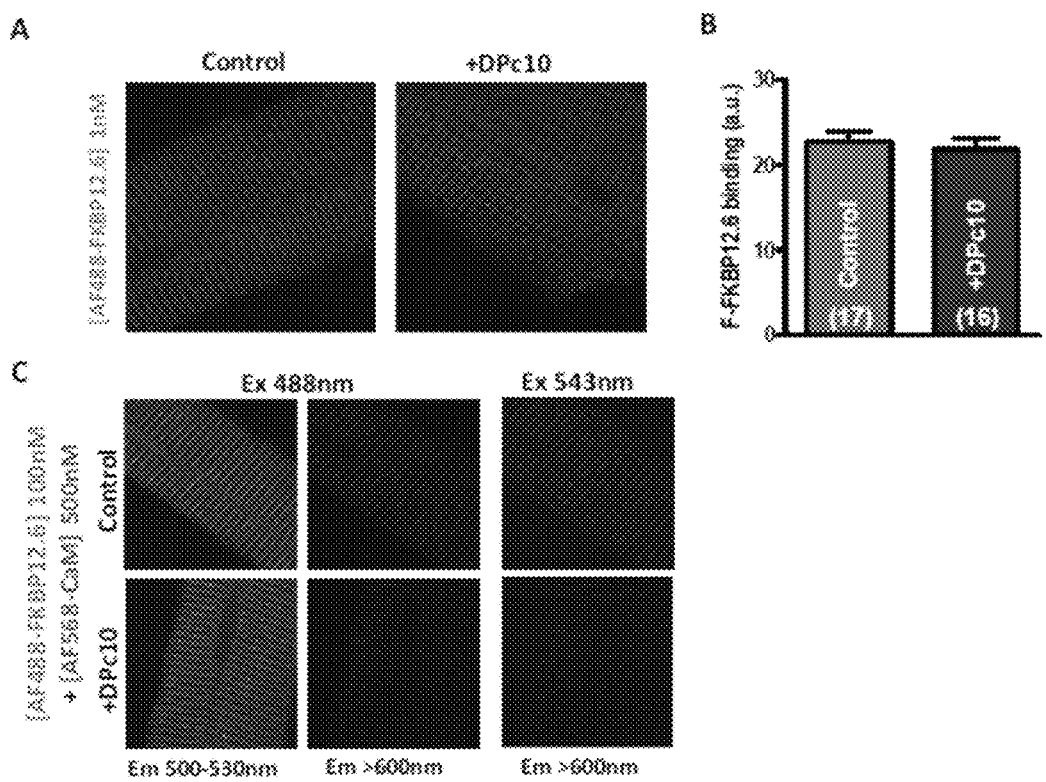
FIG. 17. A Confocal image of permeabilized myocytes after exposure to 1 nmol/L AF488-FKBP12.6 in the absence or presence of DPc10 5 µmol/L. B. Average data for AF488-FKBP12.6 binding to Z-lines with or without DPc10. C. Confocal FRET image between AF488-FKBP12.6 100 nmol/L and AF568-CaM 500 nmol/L to detect CaM at the RyR2 and total CaM at the Z-lines with or without DPc10.

To examine the converse influence that DPc10 may have on FKBP12.6 and CaM binding to RyR2 in situ, we used fluorescent FKBP12.6 and CaM variants labeled with ALEXA FLUOR™ 488 or 568 (AF488 and AF568, respectively). These fluorescent proteins were added to saponin-permeabilized myocytes with or without pre-equilibration with saturating DPc10 concentration. First, we found that AF488-FKBP12.6 at 1 nmol/L (near its $K_d$) (Guo et al., Circ Res, 2010; 106:1743-1752) forms a striated pattern that is not affected by preincubation with 5 µmon DPc10 (FIG. 17A and 17B). Thus, DPc10 does not influence FKBP12.6 binding to RyR2. To measure CaM that is specifically RyR2-bound, we measured FRET between AF488-FKBP12.6 (donor) and AF568-34-CaM (acceptor in the N-terminal domain) (Cornea et al., PNAS USA, 2009; 106:6128-6133) at a [CaM] near $K_d$ (20 nmol/L; FIG. 18Ai) (Guo et al., Biophys J, 2011;101:2170-2177; Song et al., J Blot Chem, 2008; 283:31531-31540; Yang et al., Biophys J (abstract), 2011; 100:413a-414a). Using direct excitation at 543 nm (emission at >600 nm), we detected total CaM at the Z-lines (FIG. 18AII). We also did this with high [CaM] (500 nmol/L) that saturates RyR2 with CaM under control conditions (without DPc10; FIG. 17C). FIG. 18B shows that pretreatment with DPc10 significantly reduced CaM binding (at 20 nmol/L CaM) both at the RyR2 and overall at the Z-line, and by similar proportions. Even at high AF568-34-CaM levels (500 nmol/L), DPc10-treated myocytes exhibited reduced CaM binding at the RyR2 (FRET) and at the Z-lines (total) vs control. Thus, once F-DPc10 binds to the RyR2 and decreases N-terminal-central domain interactions, it reduces the CaM affinity for RyR2. Taken together, these results show that DPc10 and CaM binding to RyR2 are mutually inhibitory. To test whether DPc10 and CaM bind at the same or nearby RyR2 sites, we measured FRET between CaM and DPc10.

FRET Between CaM and DPc10

We used a fluorescence donor probe (AF568) at the C-lobe of CaM (Cornea et al., PNAS USA, 2009; 106:6128-6133) (AF568-110-CaM) and HiLyte Fluor 647 (HF647) as the acceptor probe on the N terminus of DPc10 (HF647-DPc10). We used the acceptor photobleach approach with measurement of the resultant increase in donor (AF568-110-CaM) fluorescence in saponin-permeabilized myocytes (FIG. 18C). To use this approach quantitatively, all acceptor (DPc10) sites must be loaded so that all donors can participate in FRET.

Our results show that it is impractical to saturate RyR2 with both CaM and DPc10 (FIGS. 14B and 18B). To overcome this challenge, we pre-equilibrated the myocytes with saturating HF647-DPc10, thus loading all DPc10-binding sites on RyR2. Then, when we added AF568-110-CaM (500 nmol/L), ≈50% of RyR2s had donor but all had acceptor, allowing quantitative analysis of enhanced donor fluorescence on acceptor photobleach. FIG. 6C shows selective photobleach of HF647-DPc10 (at 635 nm) in only the central region of the myocyte, and donor fluorescence was enhanced only in that region (lower left), indicating that donors and acceptors are within FRET range.

To rule out the possibility that there is energy transfer between a donor and multiple acceptors, we measured the relationship between donor fluorescence enhancement and acceptor photobleach and found a linear relationship (FIG. 18D), which indicates a 1:1 stoichiometry for CaM-DPc10 FRET. We interpret this result as clear evidence that the FRET efficiency (E) between AF568-110-CaM and HF647-DPc10 reflects the proximity of 1 CaM to 1 DPc10. E and donor-acceptor distance calculations are described in the Methods.

FRET efficiency between AF568-110-CaM and HF647-DPc10 on 98.2%±0.2% acceptor photobleach was 0.89±0.01 (n=8). This corresponds to a distance of 53±1 Å (FIG. 18E) based on $R_0$=75 Å for the AF568-HF647 donor-acceptor pair. With an alternative donor probe (AF488), this time attached at the N-lobe of CaM, and the same acceptor (HF647) on DPc10, we measured E=0.27±0.02, which corresponds to an interprobe distance of 63±1 Å (FIG. 18E). Thus, this result shows that the donor probes on CaM are 53 to 63 Å from the acceptor on DPc10, suggesting that CaM and DPc10 can simultaneously bind at distinct, yet nearby, sites within the RyR2 structure. This again favors an allosteric rather than competitive basis for the mutual inhibition seen between CaM and DPc10 binding to the RyR2.

FRET Between FKBP12.6 and DPc10

To gain further information about the topology of the DPc10-binding site on RyR2, we used the location of FKBP12.6 as a reference point (Guo et al., *Biophys J*, 2011; 101:2170-2177; Samsó et al., *J Mol Biol*, 2006; 356:917-927; Cornea et al., *J Biol Chem*, 2010; 285:19219-19226). FKBP12.6 was labeled at position 14 (Cornea et al., *PNAS USA*, 2009; 106:6128-6133) with the fluorescent donor AF488 (AF488-FKBP12.6) or AF568 (AF568-FKBP12.6), whereas DPc10 was labeled with the acceptor HF647. We used the same 2 methods to measure FRET in permeabilized myocytes. FIG. 19A shows that when HF647-DPc10 (5 µmol/L) was added to myocytes equilibrated with donor (50 nmol/L AF568-FKBP12.6), there was strong reduction in donor emission (560-620 nm) and simultaneous appearance of FRET in the acceptor emission channel (655-755 nm). Next, we monitored the increase in donor fluorescence after acceptor photobleach when both donor (AF568-FKBP12.6) and acceptor (HF647-DPc10) were pre-equilibrated (FIG. 19B). FIG. 19B shows the increase in acceptor fluorescence before bleach and the increase in donor fluorescence after acceptor photobleach in only part of the myocyte, resulting in locally enhanced donor fluorescence. FRET between AF568-FKBP12.6 and HF647-DPc10 was almost complete (FIGS. 19A and 19B), indicating close proximity between the donor and acceptor probes. To better gauge the FKBP12.6-DPc10 distance, we used an alternative donor probe, AF488-FKBP12.6, and the same HF647 acceptor on DPc10 (to reduce $R_0$ for the FRET pair). Representative confocal images of donor quench and acceptor photobleach using AF488-FKBP12.6 as a donor are shown in FIGS. 20A and 20B.

To ensure that FRET between FKBP12.6 and DPc10 accurately reflects interprobe distance, we performed several controls. As shown in FIG. 20C, there was no significant difference in direct acceptor fluorescence intensity with or without equilibrated donors. FIG. 21D indicates that photobleach of the acceptor was essentially complete in both cases (AF488-FKBP12.6, 98.9%±0.3%; AF568-FKBP12.6, 99.4%±0.4%). We also checked the stoichiometry of donor and acceptor using the method shown in FIG. 18D. FIG. 19C shows that fluorescence of AF568-FKBP12.6 and AF488-FKBP12.6 depended linearly on HF647-DPc10 fluorescence during progressive bleach, indicating that each donor is coupled to a single acceptor.

The average FRET efficiency between AF568/488-FKBP12.6 and HF647-DPc10 was used to estimate the distance between FKBP12.6 and DPc10. The FRET efficiency between AF568-FKBP12.6 and HF647-DPc10 measured by the donor quench method was E=0.92±0.01 (n=31), whereas that measured by acceptor photobleach method was E=0.91±0.01 (n=19; FIG. 19D), corresponding to a distance of 50±1 and 51±1 Å. For the shorter $R_0$ pair (AF488-FKBP12.6 and HF647-DPc10) FRET, E by the donor quench was 0.52±0.03 (n=20), and E by acceptor photobleach was 0.51±0.01 (n=24; FIG. 19D), corresponding to distances of 53±1 and 54±1 Å, respectively. Thus, remarkably similar results were obtained with 2 different donor-acceptor pairs and 2 different methods for measuring FRET (FIG. 19E). According to our FRET results, bound DPc10 is near both FKBP and CaM, which implies that reciprocal inhibition of CaM and DPc10 binding to RyR2 occurs through an allosteric mechanism rather than competition for the same binding site. Combining information from CaM-DPc10 and FKBP12.6-DPc10 FRET allows triangulation of relative positions on the RyR2 (see Discussion).

Discussion

We used fluorescent DPc10, FKBP12.6, CaM, and confocal microscopy of permeabilized cardiomyocytes and found the following: (1) DPc10 access to its binding site is sterically hindered in resting (zipped) RyR2; (2) F-DPc10 wash-in kinetics provides a sensitive measure of the RyR2 unzipped state in permeabilized myocytes; (3) DPc10 and CaM binding to RyR2 are mutually inhibitory (via allosteric rather than competitive interaction); and (4) DPc10, CaM, and FKBP12.6 are physically 50 to 60 Å from each other as vertices of an approximately equilateral triangle on RyR2.

RyR2 is the Main Target of DPc10 Binding at Z-Lines

To assess DPc10 binding affinity and concentration at Z-lines, we used equilibrium and kinetic binding methods. Both methods (FIGS. 8C, 9C, and 10A) yielded similar $K_d$ values (≈500 nmol/L) and a $B_{max}$ value of 1.6 µmol/L, which agrees with the concentration of RyR2 monomers and FKBP12.6 at the Z-line in rat ventricular myocytes (Guo et al., *Circ Res*, 2010; 106:1743-1752; Bers et al., *Am J Physiol*, 1993; 264:C1587-C1593). This $B_{max}$ value is higher than our previous measurements of $B_{max}$ of FKBP12.6 (≈1 µmol/L), which binds very specifically (≈1 nmol/L $K_d$) to RyR2 (Guo et al., *Circ Res*, 2010; 106:1743-1752). The reason for this difference is that for DPc10 (vs FKBP12.6), the fluorescence between Z-lines is a higher fraction of that at the Z-line (FIG. 21), in part because of the much higher DPc10 concentration required to saturate RyR2. For this reason, we used the difference in Z-line vs M-line fluorescence ($F_Z$-$F_M$) to assess specific binding of F-DPc10 at the Z-lines. For FKBP12.6, we used cell average fluorescence (Guo et al., *Circ Res*, 2010; 106:1743-1752) to measure $B_{max}$ in myocytes. If we reanalyze fluorescent FKBP12.6 binding as we did for F-DPc10 (using $F_Z$-$F_M$), then the $B_{max}$ for FKBP12.6 was 1.3 µmol/L, consistent with the $B_{max}$ for F-DPc10. Furthermore, the kinetics and affinity of Z-line-associated DPc10 were almost the same as that of RyR2 specifically bound to DPc10 (FIGS. 8-10, 11, and 12). We conclude that RyR2 is the main specific Z-line target for F-DPc10.

Access of DPc10 to its RyR2-Binding Site is Restricted

We found that both the wash-in and washout kinetics of F-DPc10 binding ($k_{wash-in}$ and $k_{washout}$) are extremely slow (FIG. 10A). The calculated $k_{on}$ for F-DPc10 is ≈1800-fold slower than that we measured for FKBP12.6 under similar conditions (Guo et al., *Circ Res*, 2010; 106:1743-1752). This suggests either that DPc10 very slowly adopts a conformation that can bind RyR2 or that the DPc10-binding site on RyR2 becomes available only very slowly. The insensitivity of $k_{wash-in}$ to 10-fold higher [F-DPc10] (FIG. 10B) is most consistent with the latter interpretation, indicating that $k_{on}$ is limited by RyR2 properties that restrict the access of DPc10 to its binding site. Further supporting this hypothesis, pretreatment with NF-DPc10 (FIG. 13A) robustly increased in $k_{on}$ (≈320%). We infer that the bound NF-DPc10 shifted RyR2 to the unzipped state, allowing better access and exchange with F-DPc10. The simplest explanation for this is that the unzipped state relaxes back to the zipped state slowly with respect to F-DPc10 binding, so that when an NF-DPc10 dissociates it is more rapidly replaced by F-DPc10 (before rezipping and greater steric hindrance returns). A second related possibility is that 1 DPc10 molecule may bind at 2 sites to RyR2 (one with higher affinity than the other). When saturated by NF-DPc10 in the unzipped state, F-DPc10 may gain access and compete with NF-DPc10 at the low-affinity site. Then, when NF-DPc10 slowly dissociates from the high-affinity site, F-DPc10 is already local and can reach steady-state more rapidly (as observed). These are not mutually exclusive or unique possibilities.

We also found that enhancing RyR2 open state (by caffeine plus ryanodine) hastened the F-DPc10 association (FIG. 13B). However, these effects on F-DPc10 $k_{wash-in}$ were small compared with that of prebinding NF-DPc10, despite the very much stronger RyR2 channel opening expected. This agrees with Liu et al, (Liu et al., *J Cell Sci*, 2010; 123:1775-1784) who reported that DPc10 more strongly unzips the N-terminal and central domains than did ryanodine plus caffeine. Thus, we suggest that the unzipped and open states differ, although unzipping may increase RyR2 opening and that the open state may enhance the unzipping transition and DPc10 access (FIG. 22A).

Relationship Between FKBP12.6 and DPc10 Binding to RyR2

FKBP12.6 has been found to quiet RyR2 channel opening (Prestle et al., *Circ Res*, 2001; 88:188-194), but this is an intensely controversial issue (Bers, *Circ Res*, 2012; 110:796-799; Xiao et al., *J Biol Chem*, 2007; 282:34828-34838), and FKBP12.6 may only inhibit pathologically leaky RyRs (Oda et al., *Circulation*, 2005; 111:3400-3410). Because >80% of the RyRs in the cardiomyocytes have no natively bound FKBP12.6 (Guo et al., *Circ Res*, 2010; 106:1743-1752), adding saturating concentrations of exogenous FKBP12.6 should decrease $Ca^{2+}$ leak caused by DPc10-induced unzipping. Here, we found that FKBP12.6 has no effect on either DPc10 binding ($B_{max}$ or $\tau_{wash-in}$) or vice versa (FIGS. 14A and 14B), and it does not quiet the activating effect of DPc10 on the CaSpF (FIG. 14E). This is similar to our previous myocyte studies, in which FKBP12.6 had very minor effects on $Ca^{2+}$ sparks (Guo et al., *Circ Res*, 2010; 106:1743-1752). Taken together, these results suggest that DPc10 and FKBP12.6 act through independent mechanisms to modulate RyR2 function.

Relationship Between CaM and DPc10 Binding to RyR2

In myocytes containing a CPVT-linked RyR2 mutation, β-adrenergic stimulation decreases CaM binding at the Z-lines, and this effect is mimicked in healthy myocytes by treatment with DPc10 (Xu et al., *Biochem Biophys Res Commun*, 2010; 394:660-666). Here, we used methods designed to monitor CaM and DPc10 binding specifically at the RyR2 in myocytes, aiming to understand the structural basis of the inhibition of CaM-RyR2 binding by DPc10. One important finding in the present study is that saturating CaM binding at the RyR2 dramatically reduced F-DPc10 binding and $Ca^{2+}$ spark activation (FIG. 14), presumably by stabilizing the zipped RyR2 state.

Our novel FRET-based method allows direct assessment of CaM-RyR2 binding in the native cardiac myocyte environment (using FKBP12.6-CaM FRET) (Guo et al., *Biophys J*, 2011; 101:2170-2177). Using this method, we found that unzipping the RyR2 by treatment with saturating [DPc10] reciprocally inhibits CaM binding to RyR2 (FIG. 18B). There are 2 possible explanations for this reciprocal binding inhibition: (1) DPc10 and CaM compete to bind at overlapping sites (orthosteric mechanism) or (2) the DPc10-binding and CaM-binding sites are separate but coupled in a mutually inhibitory interaction (allosteric mechanism).

To discern between these possibilities, we assessed whether CaM and DPc10 can coexist on RyR2. In FIG. 18C, we show strong FRET between donor-labeled CaM and acceptor-labeled DPc10 at Z-lines, indicating that CaM-binding and DPc10-binding sites in neighboring regions are simultaneously occupied. This conclusion is further supported by FRET measurements using 2 different donor-acceptor pairs and 2 different labeling sites on CaM, which indicate distances of 63±1 and 53±1 Å between DPc10 and the N-lobes and C-lobes of CaM, respectively (FIG. 18E). Furthermore, FRET between FKBP12.6 and DPc10 indicates a distance of 53±3 Å between the probes, which can be compared with the 67±5-Å distance between a donor at position 14 of FKBP12.6 and an acceptor at position 34 of CaM that we previously reported (Guo et al., *Biophys J*, 2011; 101:2170-2177; Cornea et al., *J Biol Chem*, 2010; 285:19219-19226). Taken together, these results strongly support the conclusion that DPc10 and CaM bind at separate sites on RyR2, and these interact through an allosteric mutually inhibitory mechanism.

Our working hypothesis (FIG. 22A) is as follows. The resting zipped RyR2 does not readily allow DPc10 access to its site (FIG. 22Ai) and CaM binding at a different site may stabilize this zipped state (FIG. 22Aiii). We suppose that the RyR2 can transition spontaneously between the zipped and the unzipped states (FIG. 22A i-ii) but that the low probability at rest causes the slow but eventual access of DPc10 to its site. This transition may be favored when the channel is open (caffeine plus ryanodine) and also in pathological conditions (eg, HF). Once the central domain—mimicking DPc10 gains access and binds, it stabilizes the unzipped state (FIG. 22Aii) that reciprocally facilitates channel opening and inhibits CaM binding (FIG. 22Aiv).

Topology of the DPc10-Binding Site on RyR2

Although our aim here was not a detailed mapping of the DPc10-binding site within the cryo-EM 3-dimensional structure of RyR2, our FRET measurements help narrow the range of possible locations. The location of FKBP12.6 and CaM on the RyR2 structure is known from cryo-EM structural analysis, and their relative positions agree with our previous FKBP-CaM FRET studies. (Cornea et al., *PNAS USA*, 2009; 106:6128-6133; Guo et al., *Biophys J*, 2011; 101:2170-2177; Samsó et al., *J Mol Biol*, 2006; 356:917-927; Cornea et al., *J Biol Chem*, 2010; 285:19219-19226). These are represented by the centers of the blue and red spheres in FIG. 8B. Our FRET data between DPc10 and both CaM and FKBP12.6 (FIGS. 18 and 19) allow us to initially triangulate the likely location of DPc10 in the RyR2 3-dimensional structure, where the edges of the blue and red spheres intersect. The green arrows in FIG. 8B suggest a DPc10 location in the handle domain between FKBP and CaM. The clamp domain location previously proposed seems quite far from the most probable location suggested by the FRET results (Wang et al., *J Biol Chem*, 2007; 282:17785-17793). DPc10 is expected to bind the RyR2 within a 150-kDa N-terminal segment (Yamamoto et al., *Biochemistry*, 2002; 41:1492-1501), containing the first 600 residues that form a hot spot of pathogenic mutations (Priori et al., *Circ Res*, 2011; 108:871-883). The high-resolution structure of domain 1 to 559 has been reported and authoritatively docked into cryo-EM densities forming a vestibule in the cytoplasmic headpiece of RyR (see dashed black circles in FIG. 22B) (Tung et al., *Nature*, 2010; 468:585-588). A different view in FIG. 23 shows that our triangulation puts DPc10 close to, but not exactly at, that location. More detailed FRET analysis to triangulate the F-DPc10 marker is expected to more precisely locate the interdomain contact site.

We represent the FKBP12.6, CaM, and DPc10 sites all on the same face of the RyR2 tetramer. We previously showed that this is true for the FKBP-CaM FRET pair, (Cornea et al., *PNAS USA*, 2009; 106:6128-6133; Guo et al., *Biophys J*, 2011; 101:2170-2177) but we also tested whether the potential DPc10 site could be between CaM and FKBP sites on adjacent RyR2 faces. FIG. 24 shows that this possibility is implausible based on our FRET measurements.

Relevance to Heart Failure

Until now, methods to monitor local conformational changes occurring in the interacting regulatory domains of RyR have relied on a large fluorescence quencher (used in isolated SR vesicles) (Oda et al., *Circulation*, 2005; 111: 3400-3410; Tateishi et al., *Cardiovasc Res*. 2009; 81:536-545) or on FRET between a yellow fluorescent protein inserted into the N-terminal region and a cyan fluorescent protein inserted into the central region of RyR2 (in HEK293 cells) (Liu et al., *J Cell Sci*, 2010; 123:1775-1784). In this study, we show how the F-DPc10 wash-in kinetics can be used in the more native environment of permeabilized cardiomyocytes to evaluate domain interaction between the N-terminal and central domains of RyR2. This could serve as a powerful and versatile investigative tool in preclinical and clinical studies with respect to the domain unzipping hypothesis. For example, the time course of F-DPc10 wash-in can be monitored in myocytes from failing hearts in which unzipping has already occurred (Oda et al., *Circulation*, 2005; 111:3400-3410; Ono et al., *Cardiovasc Res*, 2010; 87:609-617) or can be monitored to gauge RyR function under pathological conditions (eg, oxidative stress, phosphorylation state) and in the evaluation (or validation) of drug candidates that act to stabilize the RyR2 zipped state (Oda et al., *Circulation*, 2005; 111:3400-3410; Kobayashi et al., *J Am Coll Cardiol*, 2009; 53:1993-2005).

EXAMPLE 2

This example investigates directly in cardiac myocytes how oxidation alters RyR2 conformation, as detected by measuring the fluorescently labeled DPc10 (F-DPc10) binding kinetics, and the binding affinity of fluorescent CaM and FKBP12.6. Also assessed is how dantrolene affects RyR2 conformation change and the binding affinity of CaM-RyR2, and FKBP12.6-RyR2, and DPc-10.

Materials and Methods

Cardiac Myocytes Isolation

Rat ventricular myocytes were isolated and permeabilized as previously described (Li et al., *Circ Res*. 2002; 90:309-316). Briefly, after euthanasia, the heart was quickly removed and perfused with 95% $O_2$/5% $CO_2$ gassed with 0.8 mg/ml collagenase B (Boehringer Mannheim) containing minimal essential medium (MEM, GIBCO Life Technologies). Left ventricle was minced with scissors, filtered, suspended, rinsed to prepare the rod-shaped cardiomyocytes. Isolated cardiomyocytes were placed in a laminin-coated glass culture dishes with normal Tyrode's (NT) solution. Experiments were done at room temperature.

Domain Peptide

DPc10 peptide was labeled with HiLyte Fluor™647 at AnaSpec (Fremont, Calif.). The DPc10 sequence is: 2460-GFCPDHKAAMVLFLDRVYGIEVQDFLLHLLEVGFLP-2495 (SEQ ID NO:1).

Fluorescent FKBP12.6 and CaM Probes

Single-cysteine variants of FKBP12.6 and CaM were labeled with ALEXA FLUOR™ 488 (Invitrogen), as described previously (Cornea et al., Proc Natl Acad Sci USA. 2009;106:6128-6133; Cornea et al., J Bio Chem. 2010;285:19219-19226).

Cell Permeabilization

Isolated myocytes were superfused with a relaxing solution containing (mM): EGTA 0.1, HEPES 10, K-aspartate 120, free $MgCl_2$ 1, ATP 5, phosphocreatine di-Tris 5 at pH 7.4. After myocytes were permeabilized by saponin (50 µg/ml), myocytes were placed in an internal solution containing (mM): EGTA 0.5, HEPES 10, K-aspartate 120, free $MgCl_2$ 1, ATP 5, phosphocreatine di-Tris 5, creatine phosphokinase 5 U/ml, phosphocreatine 10, dextran (MW: 40,000) 4% at pH 7.2, and $CaCl_2$, added to obtain 50 nM free $[Ca^{2+}]$ (calculated by MaxChelator).

Monitoring of $Ca^{2+}$ Sparks, SR $Ca^{2+}$ Content and Spontaneous $Ca^{2+}$ Waves Intact cardiomyocytes were loaded with Fluo-4 AM (5 µmol/L, Molecular Probes) for 15 min in NT solution (in mM): NaCl 140, KCl 4, $MgCl_2$ 1, $CaCl_2$ 2, glucose 10, HEPES 5, pH 7.4. Fluo-4 AM was excited at 488 nm and emission was recorded using a 500-530 nm bandpass filter. $Ca^{2+}$sparks were recorded after field stimulation at 1 Hz, and caffeine (10mmol/L) was rapidly perfused for assessing the SR $Ca^{2+}$content. Both $Ca^{2+}$sparks and SR $Ca^{2+}$content were recorded by using a laser scanning confocal microscope (RADIANCE2000™ MP, Bio-Rad, UK). Data were analyzed using SparkMaster, an automated analysis program that allows rapid and reliable spark analysis (Picht et al., J. Am J Physiol Cell Physiol. 2007;293:C1073-C1081). Spontaneous $Ca^{2+}$waves were recorded using a BZ9000 fluorescence digital microscope (Keyence, Japan), after 10 sec from field electric stimulation at 1,2,3,4 and 5 Hz, as described previously (Fukuda et al., Biochem Biophys Res Commun. 2014;448:1-7).

Intracellular ROS and Oxidation of RyR2

Intracellular reactive oxygen species (ROS) formation was measured in rat cardiac myocytes using a fluorescent probe, 5-(and -6)-chloromethyl-2',7'-dichlorodihydrofluoroscein diacetate ($H_2$DCFDA, 10 µmol/L) (Terentyev et al., *Circ Res*. 2008; 103:1466-1472). This assay is widely used as a reliable method for the measurement of intracellular ROS such as hydrogen peroxide, hydroxyl radicals, and hydroperoxide. The $H_2$DCFDA dye was excited with the 488 nm and emission was collected at 500-530 nm. The content of free thiols in RyR2 was determined based on the monobromobimane (mBB, Calbiochem) fluorescence intensity, as previously described (Terentyev et al., *Circ Res*. 2008; 103:1466-1472; Ho et al., *J Physiol*. 2011; 19:4697-4708). In brief, myocytes were incubated with mBB for 1 hr. Myocytes were then lysed in lysis buffer and loaded on 6% SDS-PAGE gels. The fluorescence emission intensity of the RyR2-bound mBB was measured at 482 nm by exciting at 382 nm. mBB fluorescence was normalized to the RyR2 amount, which was determined using quantitative densitometry of Coomassie Blue-stained gels.

FRET Measurements Between FKBP12.6 and DPc10

The FRET pair we used in this consisted of ALEXA FLUOR™ 488 (donor) covalently attached to FKBP12.6 (F-FKBP) and HiLyte Fluor™647 (acceptor) covalently attached to DPc10 (F-DPc10).[8] To detect F-DPc10 specifically bound to RyR2, we measured donor fluorescence intensities through a 500-530 nm bandpass filter before and after equilibration with acceptor (donor quenching method). The FRET efficiency (E) was calculated according to:

$$E = 1 - F_{DA}/F_D,$$

Where $F_D$ and $F_{DA}$ are the fluorescence intensities of the donor-only and donor-plus-acceptor samples, respectively (Oda et al., Circ Res. 2013;112:487-497).

Statistics

Data are expressed as mean±SEM, with significance assessed using student's t-test or one-way ANOVA. A p-value <0.05 was considered statistically significant.

Results
Activated RyR2 Function by Oxidation in Myocytes

Oxidation induced by hydrogen peroxide ($H_2O_2$) is expected to activate SR $Ca^{2+}$ leak through RyR2 at diastolic $[Ca]_i$ (Wagner et al., Circ Res. 2011; 108:555-65; Yan et al., Cardiovasc Res. 2008; 77:432-41). We used line-scan images to measure the effects of 50 μM/L $H_2O_2$ on $Ca^{2+}$ spark frequency (CaSpF) and SR $Ca^{2+}$ content (evaluated via rapid caffeine application) in intact cardiomyocytes after 1 Hz electric field stimulation (FIG. 25). $H_2O_2$ treatment can also inhibit SR $Ca^{2+}$-ATPase (SERCA) activity (Qin et al., J Am Heart Assoc. 2013; 2:e000184; Greensmith et al., Cell Calcium. 2010; 48:341-51). Under our conditions neither $H_2O_2$ nor dantrolene significantly altered $Ca^{2+}$ transient amplitude or time constant of $[Ca^{2+}]_i$ decline (Table 2). This indicates that the effect of $H_2O_2$ on SERCA function here was negligible. FIGS. 25A-B, and Table 3 show that $H_2O_2$ significantly increased the CaSpF and $Ca^{2+}$ spark full duration at half maximum compared with control. Thus $H_2O_2$ may enhance diastolic RyR2 channel opening. CaSpF depends on SERCA-dependent SR $Ca^{2+}$ content (Zima et al., J Physiol. 2010; 588:4743-57), but $H_2O_2$ did not significantly alter SR $Ca^{2+}$ content. So CaSpF normalized to SR $Ca^{2+}$ content, was significant increase by $H_2O_2$ treatment of myocytes (FIG. 25C).

TABLE 2

$Ca^{2+}$ transient characteristics in rat intact cardiomyocytes

|  | No. of cells | Δ $[Ca]_i$ twitch (ΔF/$F_0$) | Tau $[Ca]_i$ decline (s) |
| --- | --- | --- | --- |
| Control | 16 | 2.38 ± 0.13 | 0.32 ± 0.01 |
| +DAN | 17 | 2.35 ± 0.16 | 0.31 ± 0.01 |
| +$H_2O_2$ | 10 | 2.56 ± 0.19 | 0.32 ± 0.01 |
| +$H_2O_2$ + DAN | 7 | 2.32 ± 0.23 | 0.32 ± 0.03 |

TABLE 3

$Ca^{2+}$ spark characteristics in rat intact cardiomyocytes

|  | No. of sparks | Amplitude (ΔF/$F_0$) | FWHM (μm) | FDHM (ms) |
| --- | --- | --- | --- | --- |
| Control | 108 | 0.53 ± 0.01 | 1.86 ± 0.08 | 55.56 ± 2.56# |
| +DAN | 125 | 0.55 ± 0.01 | 1.93 ± 0.09 | 61.98 ± 3.35 |
| +$H_2O_2$ | 200 | 0.57 ± 0.01 | 2.04 ± 0.07 | 67.05 ± 3.25* |
| +$H_2O_2$ + DAN | 53 | 0.53 ± 0.02 | 1.87 ± 0.11 | 54.56 ± 3.12 |

FWHM: full width at half maximum, FDHM: full duration at half maximum.
*$p < 0.05$ vs. Control,
$P < 0.05$ vs $H_2O_2$ We also tested whether $H_2O_2$ enhanced the propensity for arrhythmogenic DADs, as measured by spontaneous $Ca^{2+}$ waves (SCW) in intact cardiac myocytes. FIG. 26A-26B shows that $H_2O_2$ treatment significantly increased the occurrence of SCW vs. control when the pacing rate increased from 1 to 5 Hz.

Dantrolene Quiets Oxidation-Induced RyR2 Activation

Dantrolene can prevent abnormal $Ca^{2+}$ leak in CPVT KI and HF models (Uchinoumi et al., Circ Res. 2010; 106: 1413-1424; Kobayashi et al., J Am Coll Cardiol. 2009; 53:1993-2005; Kobayashi et al., Circ J. 2010; 74:2579-84 Maxwell et al., Am J Physiol Heart Circ Physiol. 2012; 302:H953-63). To test whether dantrolene could prevent $H_2O_2$-induced increase in CaSpF, dantrolene was added to myocytes before $H_2O_2$ treatment. Dantrolene pretreatment had no effect on control myocytes, but suppressed the $H_2O_2$-induced increase in frequency of $Ca^{2+}$ sparks and SCW (FIGS. 25 and 26). To test whether dantrolene prevented these $H_2O_2$ effects on RyR2 by reducing the oxidative level in myocytes, we assessed oxidation levels in myocytes.

$H_2O_2$-Induced Intracellular and RyR2 Redox Modification

To monitor intracellular ROS level, we used $H_2$DCFDA (10 μmol/L). FIG. 27A shows confocal fluorescence images after applying $H_2$DCFDA to control or $H_2O_2$-treated myocytes with or without dantrolene. As shown in FIGS. 27B and 27C. The intracellular ROS level was similarly increased after addition of 50 μmol/L $H_2O_2$, with or without dantrolene pretreatment. Thus, dantrolene does not alter intracellular oxidative level. To assess whether dantrolene can attenuate the extent of RyR2 thiol modification in $H_2O_2$-treated myocytes, we used a monobromobimane (mBB) fluorescence labeling assay. FIG. 27C shows that $H_2O_2$ treatment significantly decreased the content of free thiols on RyR2 regardless of dantrolene pretreatment. Taken together, these results indicate that dantrolene did not attenuate intracellular ROS or RyR2 oxidation levels.

Effect of $H_2O_2$ on FKBP12.6 Binding to Z-Line in Permeabilized Myocytes

We assessed the molecular mechanism by which RyR2 activities were increased by $H_2O_2$-induced oxidative stress. FKBP12.6 can bind to and stabilize RyR2 channel gating, but details are controversial (Bers et al., Circ Res. 2012; 110:796-799). We measured the effect of $H_2O_2$ on FKBP12.6-RyR2 binding affinity in saponin-permeabilized myocytes using F-FKBP (Yang et al., Circ Res. 2014; 114:295-306; Cornea et al., Proc Natl Acad Sci USA. 2009; 106:6128-6133; Guo et al., Circ Res. 2010; 106:1743-1752; Guo et al., Biophys J. 2011; 101:2170-2177; Cornea et al., J Biol Chem. 2010; 285:19219-19226). FIG. 28A shows confocal images of F-FKBP with or without $H_2O_2$, and also with 1 μmol/L of the specific $Ca^{2+}$/CaM-dependent kinase II (CaMKII) inhibitor autocamtide-2-related inhibitory peptide (AIP) or 1 μmol/L dantrolene. We used 1 nmol/L F-FKBP (the its $K_d$) (Guo et al., Circ Res. 2010; 106:1743-1752), because at half-saturation it would be very sensitive to either an increase or decrease in RyR2 binding. $H_2O_2$ failed to alter F-FKBP binding to the RyR2 in permeabilized myocytes, with or without AIP or dantrolene (FIG. 28B). Thus $H_2O_2$ did not alter FKBP12.6-RyR2 affinity.

Effect of $H_2O_2$ on CaM Binding to Z-Line in Permeabilized Myocytes

CaM also binds to RyR2 and reduces RyR2 open probability, and works as a regulatory protein for RyR2 channel gating (Yamaguchi et al., J Biol Chem. 2003; 278:23480-23486; Balshaw et al., J Biol Chem. 2001; 276:20144-20153; Yang et al., Circ Res. 2014; 114:295-306); Yamaguchi et al., J Clin Invest. 2007; 117:1344-1353). We measured the effect of $H_2O_2$ on CaM-RyR2 binding affinity using F-CaM as in our previous reports (Yang et al., Circ Res. 2014; 114:295-306; Cornea et al., Proc Natl Acad Sci USA. 2009; 106:6128-6133). Both 10 and 50 μmol/L $H_2O_2$ pretreatment of myocytes reduced the F-CaM binding at the Z-line significantly (using [F-CaM]=20 nmol/L, near its $K_d$ (Yang et al., Circ Res. 2014; 114:295-306)), suggesting a decreased affinity of F-CaM/RyR2 binding (FIG. 29A-29B). However, because $H_2O_2$ was not removed before CaM addition, this effect might be due to oxidation of either RyR2 or CaM, particularly because methionines on CaM can be oxidized and cause reduced binding to RyR2 (Yamaguchi et al., J Clin Invest. 2007; 117:1344-1353).

To test whether CaM oxidation is likely to explain the reduced RyR2 binding of $H_2O_2$-treated myocytes, we first incubated [F-CaM] (50 µmol/L) in media containing 50 µmol/L $H_2O_2$ (the same concentration used in myocyte pre-incubation experiments). This allowed F-CaM oxidation (and call this F-CaM$^{Ox}$). This was then diluted 2500-fold to 20 nmol/L F-CaM$^{Ox}$ and no $H_2O_2$ was present in the myocyte bath. As shown in FIG. 29C and FIG. 30, F-CaM$^{Ox}$ displays a significant reduction in RyR2 association, but this 20% reduction is smaller than the 50% seen when F-CaM applied to myocytes pre-treated with 50 µmol/L $H_2O_2$ (FIG. 29A-29B). This suggests that both CaM and RyR2 oxidation contribute to the reduced CaM binding. It also suggest that CaM was not fully oxidized, even by our in vitro pre-exposure to 50 µmol/L $H_2O_2$ (Balog used 1000 times higher $H_2O_2$ concentration for 24 hr; Balog et al., *Am J Physiol Heart Circ Physiol*. 2006; 290:H794-H799).

As a further test of whether RyR2 oxidation alone inhibits subsequent CaM affinity, we removed $H_2O_2$ from the myocytes by repeated washing, prior to the addition of F-CaM. FIG. 31A shows confocal images of F-CaM binding at the Z-line. Myocyte oxidation (by 50 µmol/L $H_2O_2$) dramatically reduced F-CaM binding at the Z-line by 32%. That is consistent with data in FIG. 29, and that ~60% of the reduced CaM binding in FIG. 29B was due to $H_2O_2$-induced changes at RyR2, with the remainder due to effects on CaM. Dantrolene (1 µmol/L), but not the CaMKII inhibitor AIP, was able to partially restore F-CaM binding in $H_2O_2$-treated myocytes (FIG. 31B). These results indicate that $H_2O_2$-induced loss of CaM binding can be restored by dantrolene. The lack of AIP effect suggests that any CaMKII activation by $H_2O_2$ in this protocol does not contribute to the acute loss of CaM-RyR2 binding. Neither AIP nor dantrolene alter the CaM-RyR2 affinity under control conditions (FIGS. 31C and 32).

Since CaM binding to RyR2 in myocytes is known to suppress $Ca^{2+}$ sparks (Yang et al., *Circ Res*. 2014; 114:295-306; Guo et al., *Circ Res*. 2006; 99: 398-406) the $H_2O_2$-induced increase in SR $Ca^{2+}$ leak (measured as $Ca^{2+}$ sparks in FIG. 25) might be mediated mainly by the oxidation of RyR2 and CaM and reduced CaM binding to the RyR2. The restoration of CaM binding (and normal Ca sparks) by dantrolene raised a connection to our recent work (Oda et al., *Circ Res*. 2013; 112:487-497). We had shown that RyR2 CaM binding exhibits negative allosteric coupling with the accessibility of the unzipping peptide DPc10 (unzipping by DPc10 inhibits CaM binding, and CaM binding inhibits DPc10 access; Oda et al., *Circ Res*. 2013; 112:487-497). Dantrolene may also shift this balance toward the more normal state (Kobayashi et al., *J Am Coll Cardiol*. 2009; 53:1993-2005; Kobayashi et al., *Circ J*. 2010; 74:2579-84) by reducing DPc10 accessibility (zipping) and also increasing CaM affinity. We tested whether $H_2O_2$ treatment enhances DPc10 access and whether that was sensitive to dantrolene (as shown above for CaSpF and CaM binding).

Effects of Dantrolene or $H_2O_2$ on Wash-In Kinetics of HF647-DPc10

We previously reported that the wash-in kinetics of DPc10 labeled with HYLITE FLUOR™ 647 (HF647-DPc10) were greatly slowed when CaM was bound to the RyR2, which also prevented RyR2 activation by DPc10 exposure (Oda et al., Circ Res. 2013;112:487-497). Our working model was that DPc10 access to its binding site was sterically blocked when CaM was bound. Here, we first tested whether dantrolene has the same effect as CaM in preventing DPc10 access.

FIG. 33A shows confocal images of HF647-DPc10 binding after 200 min of incubation. FIG. 33B shows the time course of HF647-DPc10 wash-in with or without 1 µmol/L dantrolene. Dantrolene reduced maximal HF647-DPc10 binding ($B_{max}$) by 74%, consistent with the idea that dantrolene keeps RyR2 conformationally closed with respect to access of DPc10. However, these results could also result from competition between HF647-DPc10 and dantrolene to a site on RyR2. To test this hypothesis, we measured the HF647-DPc10 wash-out kinetics, with or without dantrolene. FIG. 34A-B shows that non-fluorescent DPc10 (NF-DPc10) can accelerate the wash-out kinetics of HF647-DPc10. This is consistent with our previous report that HF647-DPc10 and NF-DPc10 bind at the same binding site (Oda et al., *Circ Res*. 2013; 112:487-497). However, dantrolene had no effect on HF647-DPc10 wash-out kinetics, indicating that HF647-DPc10 and dantrolene binding sites are separate (FIG. 34C-D). This also suggests that the slow binding of HF647-DPc10 (and effect of dantrolene thereon) is due to on-rate effects, consistent with a conformation that strongly limits access of DPc10 to its site on RyR2.

Next we tested whether RyR2 oxidation would increase HF647-DPc10 access. Here, we used FRET between F-FKBP as a donor and HF647-DPc10 as an acceptor, to detect DPc10 that specifically binds at RyR2 (Oda et al., *Circ Res*. 2013; 112:487-497). Note that AF488-FKBP12.6 binds specifically at RyR2 with 1 nM affinity, and its binding is not influenced by CaM, $H_2O_2$ or dantrolene (Guo et al., *Circ Res*. 2010; 106:1743-1752 and FIG. 28 FRET was assessed as the decrease in F-FKBP donor fluorescence intensity by binding of HF647-DPc10 acceptor in its proximity, i.e. donor quench, as in our previous report (Oda et al., *Circ Res*. 2013; 112:487-497). $H_2O_2$ pre-incubation significantly accelerated the rate of HF647-DPc10 binding compared with control (FIG. 35A-B). This indicates that RyR2 oxidation enhances DPc10 access (e.g. by causing domain unzipping). Furthermore, pre-equilibration with dantrolene in $H_2O_2$-treated myocytes reversed the $H_2O_2$-induced acceleration of access (FIG. 35B) and reduced the maximal extent of quench (FIG. 35C), which reflects a decrease in $B_{max}$ of HF647-DPc10. Taken together, these findings showed, for the first time in situ, that $H_2O_2$ leads to defective RyR2 domain unzipping and dantrolene can correct this domain unzipping.

Discussion

Novel findings of this study are the following: In the relatively intact ventricular myocyte environment, (1) $H_2O_2$ treatment increases both CaSpF and the occurrence of SCW, but dantrolene prevents this elevated $Ca^{2+}$ leak; (2) RyR2 oxidation by $H_2O_2$ decreases its binding affinity for CaM, but does not alter its FKBP12.6 affinity; (3) RyR2 oxidation leads to domain unzipping; and (4) dantrolene corrects domain unzipping, restores the CaM-RyR2 binding affinity, and inhibits pathological RyR2 channel gating. Our working model is that modest $H_2O_2$ (or ROS) levels causes a similar pathological change in RyR2 conformation as seen in HF, in which CaM affinity is reduced, DPc10 access is increased and SR Ca leak is elevated.

RyR2 Function is Activated by $H_2O_2$

Increased ROS production has been associated with pathological states, such as HF (McMurray et al., *Eur Heart J*. 1993; 14:1493-1498), and RyR2 activity in pathological states is increased by thiol oxidation (Boraso et al., *Am J Physiol*. 1994; 267:H1010-H1016; Donoso et al., *J Mol Cell Cardiol*. 2014; 68:38-46). $H_2O_2$ can activate RyR2 function, but it also alters function of other important $Ca^{2+}$-handing proteins, including SERCA and $Na^+$—$Ca^{2+}$ exchange (NCX). Yan et al. (Yan et al., *Cardiovasc Res*. 2008; 77:432-41) showed that CaSpF increased during 10 min of treatment with 50 µmol/L $H_2O_2$ in intact myocytes. On the other hand, higher [$H_2O_2$] (200 µmol/L) can reduce $Ca^{2+}$ transient amplitude, CaSpF, and SR $Ca^{2+}$ content, consistent with $H_2O_2$-dependent inhibition of SERCA activity (Greensmith et al., *Cell Calcium*. 2010; 48:341-51). To assess whether $H_2O_2$ activates the RyR2 function, we measured CaSpF under conditions where both amplitude and the rate of $Ca^{2+}$ transient decline (reflecting SERCA activity), and the decay of caffeine-induced $Ca^{2+}$ transient (reflecting NCX activity), were similar. This indicates that both SERCA and NCX function were not appreciably altered under our conditions. Thus, RyR2 function may be more sensitive to $H_2O_2$-induced modulation than are SERCA or NCX. We also found a significant increase in the occurrence of arrhythmogenic SCW in $H_2O_2$-treated myocytes, when pacing rate increased from 1 to 5 Hz, indicating that hyperactivity of RyR2 by oxidation may contribute to triggering lethal arrhythmias.

Dantrolene Restores $H_2O_2$-Induced RyR2 Activation without Altering Cellular and RyR2 Oxidation Dantrolene has been shown to bind to amino acids 601-620 of RyR2 (Paul-Pletzer et al., *Biochem J*. 2005; 387:905-909) and stabilize the RyR2 channel gating in pathological states, such as HF (Maxwell et al., *Am J Physiol Heart Circ Physiol*. 2012; 302:H953-63) or CPVT (Jung et al., *EMBO Mol Med*. 2012; 4:180-191). However, dantrolene has no effect on $Ca^{2+}$ signaling under control condition (Maxwell et al., *Am J Physiol Heart Circ Physiol*. 2012; 302:H953-63; Diaz-Sylvester et al., *Am J Physiol Cell Physiol*. 2008; 294:C1103-C1112). These are consistent with our observation that dantrolene significantly reduced the CaSpF and prevented potentially deleterious spontaneous arrhythmogenic $Ca^{2+}$ waves in $H_2O_2$-treated myocytes, but did not alter the frequency of $Ca^{2+}$ sparks and SCW under control condition. To exclude the possibility that dantrolene attenuated the oxidation level to achieve this effect, we measured intracellular ROS production and RyR2 free thiol content in dantrolene-treated myocytes. Dantrolene influenced neither cellular nor RyR2 oxidation level, suggesting that dantrolene directly stabilized RyR2, possibly by inhibiting domain unzipping (Krause et al., Anaesthesia. 2004; 59:364-373).

$H_2O_2$ Reduced CaM, but not FKBP12.6 Binding to RyR2

There are two main possible explanations for $H_2O_2$-induced defective CaM binding to RyR2: (1) Oxidation of CaM inhibits the productive association of CaM with RyR2 or (2) Oxidation of RyR2 prevents the CaM binding to its binding site. Balog et al. (Balog et al., *Am J Physiol Heart Circ Physiol*. 2006; 290:H794-H799) reported that extensive in vitro oxidation of CaM abolishes the functional interaction between CaM and RyR2. That is consistent with our in situ observation that our much milder exposure to $H_2O_2$ caused some CaM oxidation and reduction of binding to RyR2 (FIG. 29C). On the other hand, it has been previously proposed (Balshaw et al., *J Biol Chem*. 2001; 276:20144-20153) that oxidation of RyR2 enhances RyR2 activity by decreasing CaM binding affinity. This also agrees with our myocyte result that RyR2 oxidation reduced subsequent CaM binding (FIG. 31). Taken together, these results strongly support the conclusion that oxidation of both CaM and RyR2 cause reduced CaM-RyR2 binding and this combined mechanism contributes to RyR2 dysfunction during oxidative stress. One of the interesting findings here is that dantrolene restores the CaM-RyR2 binding in $H_2O_2$-treated myocytes, resulting in lower resting RyR2 leak, as has been seen for dantrolene in HF or CPVT models (Kobayashi et al., *Circ J*. 2010; 74:2579-84; Ono et al., *Cardiovasc Res*. 2010; 87:609-617), without changing intracellular and RyR2 oxidative level (FIG. 27).

FKBP12.6 binds to RyR2 with high affinity and can also influence RyR2 gating (Guo et al., *Circ Res*. 2010; 106: 1743-1752; Prestle et al., *Circ Res*. 2001; 88:188-194; Marx et al., *Circ Res*. 2001; 88:1151-1158) and has been proposed to play an important role in stabilizing RyR2 function (Prestle et al., *Circ Res*. 2001; 88:188-194; Marx et al., *Circ Res*. 2001; 88:1151-1158; Shan et al., J Cin Invest. 2010; 120:4375-4387), although this issue is controversial (Guo et al., *Circ Res*. 2010; 106:1743-1752; Greensmith et al., *Cell Calcium*. 2010; 48:341-51; Stange et al., *J Biol Chem*. 2003; 278:51693-51702; Houser et al., *Circ Res*. 2014 11;114: 1320-1327). Shan et al. reported (Shan et al., J Cin Invest. 2010; 120:4375-4387) that 1 mmol/L $H_2O_2$ combined with phosphorylation of Ser2808 by PKA could reduce FKBP12.6 binding to RyR2 by ~70%. In contrast, we find that neither PKA-dependent phosphorylation (Guo et al., *Circ Res*. 2010; 106:1743-1752), DPc10-induced unzipping (Oda et al., *Circ Res*. 2013; 112:487-497) nor the more moderate levels of $H_2O_2$ used here had any effect on FKBP12.6 binding to RyR2 in myocytes (FIG. 28). In our hands CaM has much stronger effects on RyR2 function than does FKBP12.6, with more pronounced changes during pathophysiological conditions such as HF (Yang et al., *Circ Res*. 2014; 114:295-306), oxidation or DPc10-induced unzipping.

Dantrolene Corrects RyR2 Conformation Caused by Either $H_2O_2$ or DPc10

We previously demonstrated that monitoring F-DPc10 binding kinetics is a powerful tool to evaluate functionally important RyR2 conformational changes, likely related to an interaction between the N-terminal and central domains of RyR2. Using this method, we now show that $H_2O_2$ significantly accelerates F-DPc10 association rate in situ, indicating that $H_2O_2$ causes domain unzipping (FIG. 35). We also found that dantrolene reduces access of F-DPc10 in either $H_2O_2$- or DPc10-treated myocytes, which suggests that $H_2O_2$ and DPc10 may induce similar structural changes that are both corrected by dantrolene (FIGS. 33 and 36). These findings are consistent with previous in vitro reports that oxidative stress of RyR2 in SR vesicles weakens domain interactions (Yano et al., *Circulation*. 2005; 112:3633-3643) and that dantrolene improves RyR2 function via correcting domain unzipping (Kobayashi et al., *J Am Coll Cardiol*. 2009; 53:1993-2005). The $B_{max}$ for F-DPc10 is lower in dantrolene-treated myocytes. That could have been a result of DPc10 and dantrolene competing at the same site. But we have ruled out that possibility. First, we measured the wash-out kinetics of F-DPc10 with or without NF-DPc10 in wash-out solution. Since F-DPc10 wash-out rate was faster with NF-DPc10 (FIG. 34A-B), we infer that F-DPc10 and NF-DPc10 bind to RyR2 at the same site. Second, dantrolene did not alter the wash-out kinetics of F-DPc10. Thus, dantrolene seems to prevent access (drastically reducing on-rate), but does not alter F-DPc10 dissociation (off-rate) (FIG. 34C-D). This observation supports the conclusions that F-DPc10 and dantrolene bind at separate sites on RyR2, and that dantrolene influences DPc10 access by an allosteric mechanism.

CaMKII can also be activated by oxidation at methionine 281/282 (Erickson et al., *Cell*. 2008; 133:462-474) and can also phosphorylate and activate RyR2 (Guo et al., *Circ Res*. 2006; 99: 398-406; Erickson et al., *Cell*. 2008; 133:462-474) and this CaMKII pathway would be expected to exacerbate the direct RyR2 and CaM effects on RyR2 gating that has been the focus here. Moreover, here we used the CaMKII inhibitors AIP (CaM binding experiments) and KN-93 (SCW experiments) specifically to assess CaMKII-independent effects of $H_2O_2$ on $Ca^{2+}$ waves, CaM binding to RyR2. Wagner et al. (Wagner et al., *Circ Res*. 2011; 108:555-65) have shown that the increase in CaSpF and SR Ca leak observed with 200 μmol/L $H_2O_2$ was not prevented by KN-93, consistent with a CaMKII-independent effect of $H_2O_2$ on RyR2 dysfunction.

These results indicate that abnormal oxidative modification of RyR2 by $H_2O_2$ causes reduced CaM affinity of RyR2 (by oxidation of sites on both CaM and RyR2) and RyR2 conformation changes (domain unzipping) that lead to untimely and potentially arrhythmogenic RyR2 channel opening. Dantrolene restores normal CaM binding, conformational state and quiets pathological RyR2 channel gating. This $H_2O_2$-induced structural unzipping, reduced CaM binding and more active RyR2 may represent a functionally integrated common pathological RyR2 state that is relevant for HF, oxidative stress and even CPVT-linked genetic mutations.

EXAMPLE 3

Using the method illustrated in FIGS. 3 and 4, a preliminary screen of NIH Clinical Collection 1 (NCC1, 446 compounds) was conducted. The concentrations of A-CaM and D-FKBP were near their $K_d$. FLT detection showed excellent precision (CV=0.2%) similar to our previous GFP/RFP-SERCA assays (FIG. 2C). In FIG. 36, we represented the effect of compounds on FRET as E(compound)/E(control) ($E/E_0$). Values outside the 3SD threshold (dotted line) are considered hits. Increased FRET ($E/E_0>1$) indicates increased FKBP and/or CaM binding; decreased FRET ($E/E_0<1$) indicates decreased FKBP and/or CaM binding. The immunosuppressant Tacrolimus (a.k.a. FK506) was among the hits, suggesting this method functions to identify molecules that reduce binding of FKBP and/or CaM. FK506 is known to prevent FKBP/RyR binding (hence the reduced FRET), and may serve as a positive control in future HTS campaigns. Some hits (Pravastatin, Cladribine, Linopirdine, Ebselen, and Nicotinamide) are known to perturb intracellular $Ca^{2+}$ cycling and will be further tested in dose-response FRET assays (ranging 0-100 μM compound), to determine their affinity for the RyR complex. $^3$H-ryanodine binding assays will be carried out to determine their effect on RyR1 channel function. Hits that inhibit RyR at resting $Ca^{2+}$ (and have no significant effect under activating $Ca^{2+}$) will be considered for use as positive controls in subsequent HTS campaigns.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method for identifying a compound that modulates a ryanodine receptor (RyR) homotetrameric calcium channel comprising:
   providing a complex comprising an RyR homotetrameric calcium channel (RyR molecule), an FK-binding protein (FKBP), and a modulatory protein, wherein the FKBP comprises a covalently attached donor probe, and wherein the modulatory protein comprises a covalently attached acceptor probe, and wherein the donor probe and the acceptor probe can be used for energy transfer;
   contacting the complex with a test compound to form a mixture;
   measuring the fluorescence lifetime or intensity of the donor probe, wherein measuring fluorescence lifetime comprises direct waveform recording detection.

2. The method of claim 1 wherein the molar concentration of the FKBP is at, or within one order of magnitude, of the dissociation constant ($K_d$) of the FKBP for the RyR molecule, and the molar concentration of the modulatory protein is at, or within one order of magnitude, of the $K_d$ of the modulatory protein for the RyR molecule.

3. The method of claim 1 wherein the modulatory protein is calmodulin, S100A1, or sorcin.

4. The method of claim 1 wherein the fluorescence lifetime or intensity of the donor probe is changed in the presence of the test compound.

5. The method of claim 4 wherein the change between the fluorescence lifetime in the presence of the test compound and the fluorescence lifetime in the absence of the test compound is a ΔE of greater than 3 times the ΔE standard deviation of a control.

6. The method of claim 1 wherein the measuring comprises high throughput screening.

7. The method of claim 1 wherein the RyR molecule is an RyR1 molecule or an RyR2 molecule.

8. The method of claim 1 wherein the complex is present in a permeabilized cell.

9. The method of claim 1 wherein the complex is present in a purified membrane.

10. The method of claim 1 wherein the mixture comprises a compound selected from $H_2O_2$ and oxidized glutathione.

11. The method of claim 1 wherein the complex further comprises a domain peptide.

12. The method of claim 11 wherein the domain peptide is DPc-10.

13. The method of claim 11 wherein the concentration of the domain peptide is at, or within one order of magnitude, of the $K_d$ of the domain peptide for the RyR molecule.

14. The method of claim 11 wherein the concentration of the FKBP is a saturating concentration, the concentration of the domain peptide is a saturating concentration, or the combination thereof.

15. The method of claim 1 wherein the FKBP is FKBP12 or FKBP12.6.

* * * * *